(12) United States Patent
Damha et al.

(10) Patent No.: US 9,719,091 B2
(45) Date of Patent: *Aug. 1, 2017

(54) OLIGONUCLEOTIDE DUPLEXES COMPRISING DNA-LIKE AND RNA-LIKE NUCLEOTIDES AND USES THEREOF

(71) Applicant: PALADIN LABS INC., Montreal (CA)

(72) Inventors: Masad J. Damha, St. Hubert (CA); Jonathan K. Watts, Dallas, TX (US); Glen Deleavey, Montreal (CA)

(73) Assignee: Paladin Labs, Inc., Montréal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/810,148

(22) Filed: Jul. 27, 2015

(65) Prior Publication Data

US 2016/0145613 A1    May 26, 2016

Related U.S. Application Data

(63) Continuation of application No. 12/996,362, filed as application No. PCT/CA2009/000789 on Jun. 5, 2009, now Pat. No. 9,090,649.

(60) Provisional application No. 61/059,186, filed on Jun. 5, 2008.

(30) Foreign Application Priority Data

Jun. 17, 2008 (CA) .................................. 2635187
Jun. 17, 2008 (WO) ................ PCT/CA2008/002259

(51) Int. Cl.
C07H 21/04    (2006.01)
C07H 21/00    (2006.01)
C07H 21/02    (2006.01)
C12N 15/11    (2006.01)
C12N 15/113   (2010.01)

(52) U.S. Cl.
CPC .......... *C12N 15/113* (2013.01); *C07H 21/00* (2013.01); *C07H 21/02* (2013.01); *C12N 15/111* (2013.01); *C12N 2310/14* (2013.01); *C12N 2310/322* (2013.01); *C12N 2310/323* (2013.01); *C12N 2320/30* (2013.01); *C12N 2320/51* (2013.01); *C12N 2320/53* (2013.01)

(58) Field of Classification Search
None
See application file for complete search history.

(56) References Cited

U.S. PATENT DOCUMENTS

| | | | |
|---|---|---|---|
| 5,539,082 A | 7/1996 | Nielsen et al. | |
| 5,580,859 A | 12/1996 | Felgner et al. | |
| 5,589,466 A | 12/1996 | Felgner et al. | |
| 5,593,972 A | 1/1997 | Weiner et al. | |
| 6,083,482 A | 7/2000 | Wang | |
| 6,338,859 B1 | 1/2002 | Leroux et al. | |
| 6,639,059 B1 | 10/2003 | Kochkine et al. | |
| 6,734,291 B2 | 5/2004 | Kochkine et al. | |
| 6,780,324 B2 | 8/2004 | Le Garrec et al. | |
| 6,780,428 B2 | 8/2004 | Ranger et al. | |
| 6,939,564 B2 | 9/2005 | Ranger et al. | |
| 7,018,655 B2 | 3/2006 | Lele et al. | |
| 7,053,207 B2 | 5/2006 | Wengel | |
| 7,084,125 B2 | 8/2006 | Wengel | |
| 7,094,810 B2 | 8/2006 | Sant et al. | |
| 7,262,253 B2 | 8/2007 | Luo et al. | |
| 7,510,731 B2 | 3/2009 | Ranger et al. | |
| 7,838,600 B2 | 11/2010 | Luo et al. | |
| 9,090,649 B2 | 7/2015 | Damha et al. | |
| 2002/0132788 A1 | 9/2002 | Lewis et al. | |
| 2002/0173478 A1 | 11/2002 | Gewirtz | |
| 2003/0143732 A1 | 7/2003 | Fosnaugh et al. | |
| 2004/0180351 A1 | 9/2004 | Giese et al. | |
| 2005/0196787 A1 | 9/2005 | Bhanot et al. | |
| 2006/0198891 A1 | 9/2006 | Ravenelle et al. | |
| 2009/0258071 A1 | 10/2009 | Lessard et al. | |

FOREIGN PATENT DOCUMENTS

| | | |
|---|---|---|
| WO | WO-2004083430 A2 | 9/2004 |
| WO | WO-2007031877 A2 | 3/2007 |
| WO | WO-2007048244 A2 | 5/2007 |
| WO | WO-2007068113 A1 | 6/2007 |
| WO | WO-2008011431 A2 | 1/2008 |

OTHER PUBLICATIONS

U.S. Appl. No. 12/996,362, filed Dec. 3, 2010, Oligonucleotide Duplexes Comprising DNA-Like and RNA-Like Nucleotides and Uses Thereof.
Allerson et al., "Fully 2'-Modified Oligonucleotide Duplexes with Improved in Vitro Potency and Stability Compared to Unmodified Small Interfering RNA," J. Med. Chem., 48: 901-904, 2005.
Berger, I. et al. (1998) "Crystal structures of B-DNA with incorporated 2'-deoxy-2'-fluoro-arabino-furanosyl thymines: implications of conformational preorganization for duplex stability," Nucleic Acids Res. 26 (10): pp. 2473-2480.
Blidner, R. et al., (2007) "Fully 2'-Deoxy-2'-Fluoro Substituted Nucleic Acids Induce RNA Interference in Mammalian Cell Culture," Chem. Biol. Drug Des. 70: 113-122.

(Continued)

Primary Examiner — Jennifer McDonald
(74) Attorney, Agent, or Firm — Goodwin Procter LLP

(57) ABSTRACT

Novel oligonucleotide pairs which can form a duplex comprising one or more DNA-like nucleotides (e.g., 2'-substituted arabinonucleotides (ANA)); in combination with one or more RNA-like nucleotides (e.g., 2'-substituted ribonucleotides (RNA) and/or locked nucleic acid nucleotides (LNA)), are disclosed. The use of such oligonucleotide duplexes, such as for silencing the expression of a nucleic acid or gene of interest using small interfering RNA (siRNA) technologies, is also disclosed.

20 Claims, 10 Drawing Sheets

(56) References Cited

OTHER PUBLICATIONS

Bocchetta, M., et al. (2004) "Epidemiology and molecular pathology at crossroads to establish causation: molecular mechanisms of malignant transformation," Oncogene, v.23:6484-91.
Braasch et al., "Novel Antisense and Peptide Nucleic Acid Strategies for Controlling Gene Expression," Biochemistry, 41(14): 4503-4510, 2002.
Brummelkamp et al., "A System for Stable Expression of Short Interfering RNAs in Mammalian Cells," Science, 296: 550-553, 2002.
Corey, D. (2007) "Chemical modification: the key to clinical application of RNA interference?" *J. Clin. Invest.* 117: 3615-3622.
Damha, M. et al. (2006) "Arabinose-modified siRNAs ('siANA & siFANA')," Am. Chem Soc. 231: p. 8 (Abstract from National Meeting).
Damha, Masad J., PowerPoint slide presentation entitled "Arabinose-modified Oligonucleotides" presented at the 231st ACS National Meeting, Atlanta, GA, on Mar. 26, 2006, (47 pages).
Deleavey, Glen F. et al. (2010) "Synergistic effects between analogs of DNA and RNA improve the potency of siRNA-mediated gene silencing," *Nucleic Acids Res.* 38 (13): pp. 4547-4557.
Denisov, A. et al. (2001) "Solution structure of an arabinonucleic acid (ANA)/RNA duplex in a chimeric hairpin: comparison with 2'-fluoro-ANA/RNA and DNA/RNA hybrids," Nucleic Acids Res. 29 (21): pp. 4284-4293.
Dorsett et al., "siRNAs: Applications in Functional Genomics and Potential as Therapeutics," Nat. Rev. Drug Discov., 3: 318-329, 2004.
Dowler et al., "Inprovements in siRNA properties mediated by 2'-deoxy-2'fluoro-.beta.- D-arabinonucleic acid (FANA)," Nucleic Acids Research, 34(6): 1669-1675, 2006.
Elbashir et al., "Duplexes of 21-nucleotide RNAs mediate RNA interference in cultured mammalian cells," Nature, 411: 494-498, 2001.
Elmén, J. et al. (2005) "Locked nucleic acid (LNA) mediated improvements in siRNA stability and functionality," *Nucleic Acids Res.* 33 (1): pp. 439-447.
Ferrari, N. et al. (2006) "Characterization of antisense oligonucleotides comprising 2'-deoxy-2'fluoro-.beta.-D-arabinonucleic acid (FANA): specificity, potency, and duration of activity," Annals of the New York Academy of Sciences 1082: pp. 91-102.
Hoshika et al., "RNA interference induced by siRNA modified with 4'- thioribonucleosides in cultured mammalian cells," FEBS Letters, 579: 3115-3118, 2005.
Ikeda, H. et al. (1998) "The effect of two antipodal fluorine-induced sugar puckers on the conformation and stability of the Dickerson-Drew dodecamer duplex [d(CGCGAATTCGCG)]2," *Nucleic Acids Res.* 26 (9): pp. 2237-2244.
International Search Report and Written Opinion, PCT App. PCT/CA2009/000789, 16 pages (Sep. 21, 2009).
Kalota, A. et al. (2005) "2'-deoxy-2'-fluoro (2' F-ANA) ribose modification significantly enhances the duration, and efficiency, of nucleic acid mediated gene silencing," Database Biosis [Online] Biosciences Information Service, Database accessionNo. PREV200600185430 (Abstract).
Kalota, A. et al. (2006) "2'-Deoxy-2'-fluoro-beta-D-arabinonucleic acid (2'F-ANA) modified oligonucleotides (ON) effect highly efficient, and persistent gene silencing," Nucleic Acids Res. 34 (2): pp. 451-461.
Kim et al., "Synthetic dsRNA Dicer substrates enhance RNAi potency and efficacy," Nature Biotechnology, 23(2): 222-226, 2005.
Koller et al., "Competition for RISC binding predicts in vitro potency of siRNA," Nucleic Acids Research, 34(16): 4467-4476, 2006.
Layzer et al., "In vivo activity of nuclease-resistant siRNAs," RNA, 10: 766-771, 2004.
Lesnik, E. et al. (1993) "Oligodeoxynucleotides Containing 2'-O-Modified Adenosine: Synthesis and Effects on Stability of DNA:RNA Duplexes," *Biochemistry* 32: pp. 7832-7838.
Lewis, "Efficient delivery of siRNA for inhibition of gene expression in postnatal mice," Nature Genetics, 32: 107-108, 2002.
Nielsen et al., "Sequence-Selective Recognition of DNA by Strand Displacement with a Thymine-Substituted Polyamide," Science, 254(5037): 1497-1500, 1991.
Novac et al., "Inhibitors of protein synthesis identified by a high throughput multiplexed translation screen," Nucleic Acids Research, 32(3): 902-915, 2004.
Opalinska et al "Nucleic acid therapeutics for hematologic malignancies—theoretical considerations " Ann N Y Acad Sci. Oct. 2006;1082:124-36.
Opalinska et al., "Nucleic-Acid Therapeutics: Basic Principles and Recent Applications," Nature Reviews, 1: 503-514, 2002.
Pillai et al., "Inhibition of Translational Initiation by Let-7 MicroRNA in Human Cells," Science, 309: 1573-1576, 2005.
Ratmeyer et al., "Sequence Specific Thermodynamic and Structural Properties for DNA-RNA Duplexes," Biochemistry, 33: 5298-5304, 1994.
Shen et al., "Gene silencing by adenovirus-delivered siRNA," FEBS Letters, 539: 111-114, 2003.
Simeoni et al., "Insight into the mechanism of the peptide-based gene delivery system MPG: implications for delivery of siRNA into mammalian cells," Nucleic Acids Research, 31(11): 2717-2724, 2003.
Sorensen et al., "Gene Silencing by Systemic Delivery of Synthetic siRNAs in Adult Mice," J. Mol. Biol., 327: 761-766, 2003.
Supplementary European Search Report and Search Opinion for European Patent Application No. EP09757018, dated Nov. 19, 2012, 12 pages.
Uhlmann et al., "Antisense Oligonucleotides: A New Therapeutic Principle," Chemical Reviews, 90(4): 543-84, 1990.
Ui-Tei, K. et al. (2008) "Functional dissection of siRNA sequence by systematic DNA substitution: modified siRNA with a DNA seed arm is a powerful tool for mammalian gene silencing with significantly reduced off-target effect," *Nucleic Acid Res.* 36 (7): pp. 2136-2151.
Watts et al., "2'-Fluoro-4'-thioarabino-modified oligonucleotides: conformational switches linked to siRNA activity," Nucleic Acids Research, 35(5): 1441-1451, 2007.
Wilds, C. et al. (2000) "2'-Deoxy-2'-fluoro-beta-D-arabinonucleic acid (2'F-ANA): synthesis and physicochemical studies," Nucleic Acids Res. 28 (18): pp. 3625-3635.
Wu et al., "Properties of Cloned and Expressed Human RNase H1," The Journal of Biological Chemistry, 274(40): 28270-28278, 1999.
Xia et al., "siRNA-mediated gene silencing in vitro and in vivo," Nature Biotechnology, 20: 1006-1010, 2002.
Zhang, H. et al. (2006) "RNA Interference with Chemically Modified siRNA," *Curr. Top. Med. Chem.* 6(9): 893-900.

FIG. 2A
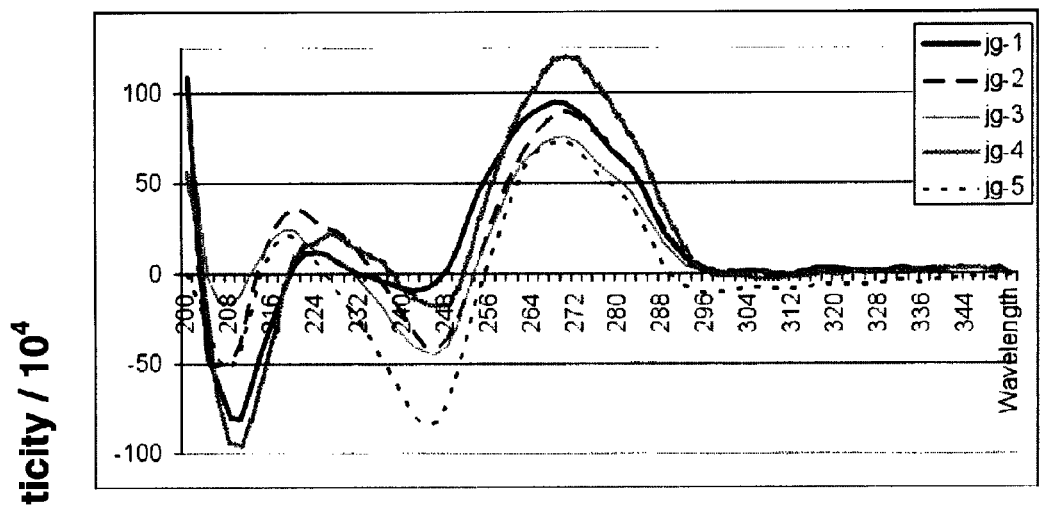
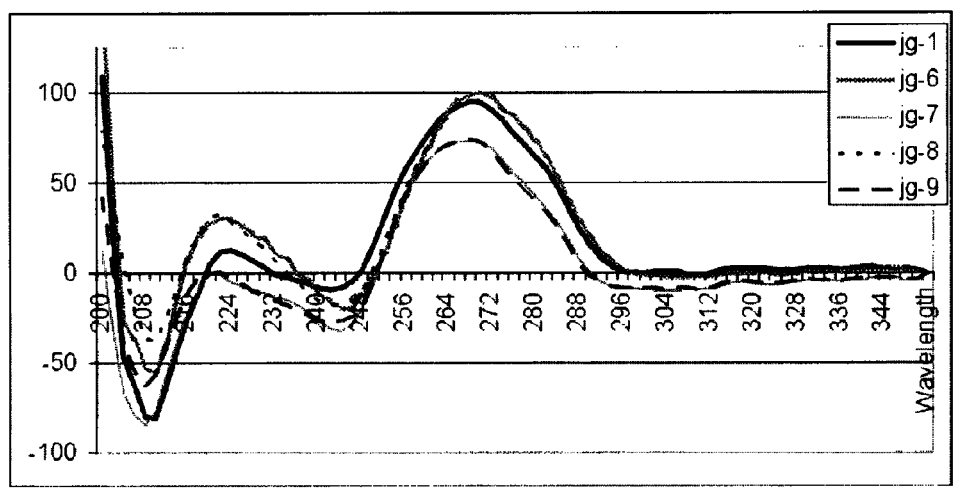
FIG. 2B

FIG. 2C
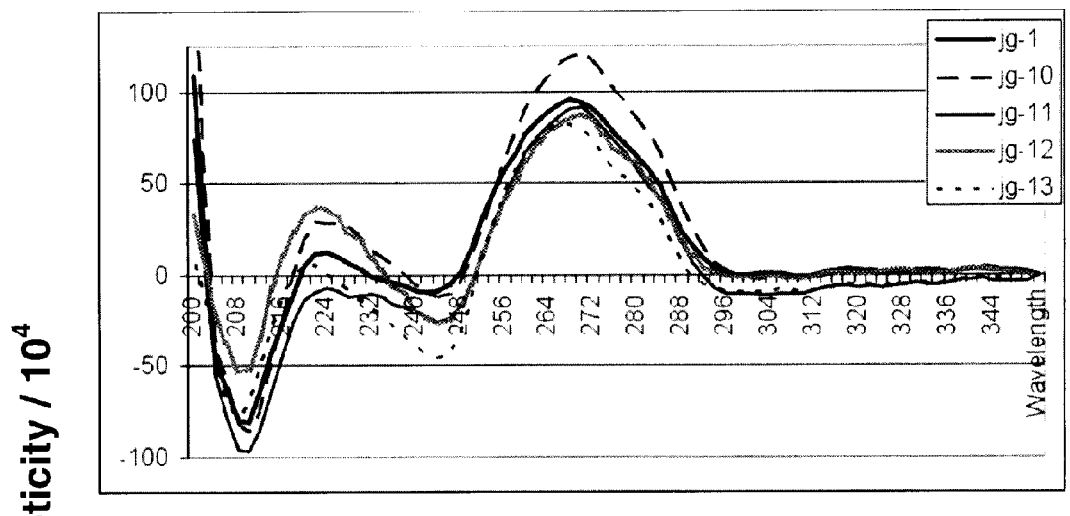
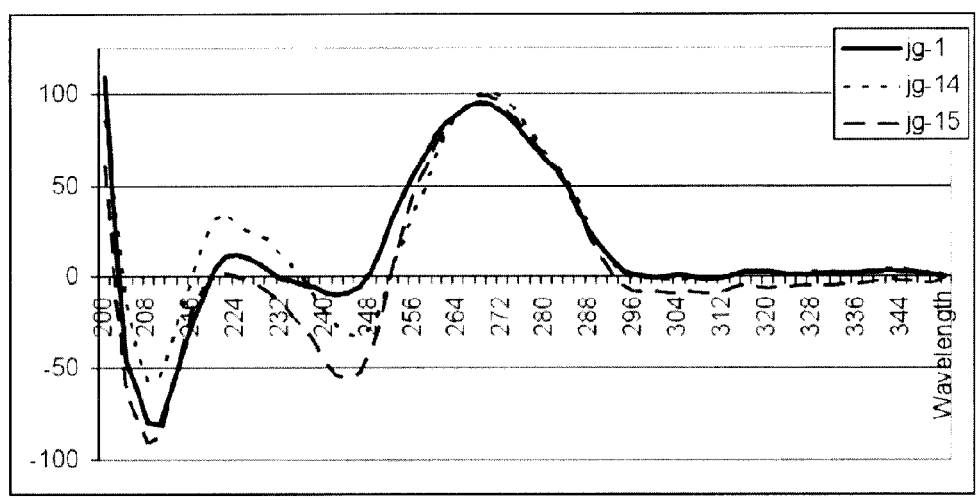
FIG. 2D

OLIGONUCLEOTIDE DUPLEXES COMPRISING DNA-LIKE AND RNA-LIKE NUCLEOTIDES AND USES THEREOF

CROSS REFERENCE TO RELATED APPLICATIONS

This application is a continuation of U.S. patent application Ser. No. 12/996,362 filed Dec. 3, 2010, which is a U.S. national phase application under 35 U.S.C. §371 of International Patent Application No. PCT/CA09/00789 filed on Jun. 5, 2009, which claims priority to and the benefit of U.S. Provisional Patent Application No. 61/059,186, filed on Jun. 5, 2008, of Canadian Patent Application No. 2,635,187, filed on Jun. 17, 2008, and of International Patent Application No. PCT/CA2008/002259, filed on Dec. 19, 2008. The contents of these applications are incorporated herein by reference in their entirety.

SEQUENCE LISTING

This application contains a Sequence Listing in computer readable form entitled "LAB-032C1_SL.txt" created Jul. 27, 2015, having a size of 44.0 KB, which is incorporated herein by reference in its entirety.

TECHNICAL FIELD

The invention relates to oligonucleotides, methods for their preparation and uses thereof, such as for decreasing the level of a target nucleic acid in a cell, and/or silencing the expression of a nucleic acid or gene of interest using small interfering RNA (siRNA) technologies.

BACKGROUND ART

Gene silencing, i.e., selectively blocking the expression of a gene of interest, may be effected via the introduction of an antisense oligonucleotide (AON) or small interfering RNA (siRNA) into an organism (Uhlmann, E. and Peyman, A. *Chem. Rev.* 1990, 90: 543-84; Braasch, D. A. and Corey, D. R. *Biochemistry* 2002, 41: 4503-4510; Opalinska, J. B. and Gewirtz, A. M. *Nat. Rev. Drug Discov.* 2002, 1: 503-14; Dorsett, Y. and Tuschl, T. *Nat. Rev. Drug Discov.* 2004, 3: 318-329). Unfortunately, as with other nucleic acid-based drugs, siRNAs have poor serum stability, poor cellular uptake, and can elicit off-target and immunostimulatory side effects. Efforts to remedy these shortcomings have focused on the development of delivery vehicles for siRNAs, and on the development of chemically modified oligonucleotides with improved drug profiles.

Much recent work has focussed on the chemical modification of siRNA. Dowler et al. (Dowler, T. et al. *Nucl. Acids Res.* 2006, 34: 1669-1675) were the first to show that 2'-deoxy-2'F-arabinonucleic acids (2'F-ANA) could be incorporated throughout the sense strand, including a fully-modified sense strand. Modification of the antisense-strand 3'-overhang with 2'F-ANA brought a significant increase in potency, and several of the 2'F-ANA-modified duplexes have been able to surpass the native siRNA in potency. Furthermore, siRNA duplexes with extensive 2'F-ANA modification were found to have a significantly longer serum half-life than unmodified siRNAs. Modified siRNA duplexes containing 2'-fluoro-4'-thioarabinonucleotide (4'S-FANA) units were able to enter the RNAi pathway (Watts, J. K. et al. *Nucl. Acids Res.* 2007, 35: 1441-1451). One or two inserts internally in either strand gave duplexes of potency comparable to that of the control. The 4'S-FANA modification was also able to work with good efficiency in a duplex with a modified 2'F-ANA-RNA sense strand, demonstrating that 2'F-ANA (with its preference for southern and eastern conformations) can achieve synergy with 4'S-2'F-ANA (with its preference for northern conformations), in RNAi gene silencing.

2'F-RNA is another siRNA modification, and partial 2'F-RNA modification is tolerated throughout both the sense and antisense strands, and some fully-modified 2'F-RNA siRNAs are also active. 2'F-RNA-modified siRNA duplexes have significantly increased serum stability (Layzer, J. M. et al. *RNA*, 2004, 10: 766-771). 2'F-RNA also increases the binding affinity of the duplex.

An example of an increase in potency was observed for a fully modified siRNA made of a combination of 2'-O-Me and 2'F-RNA modified nucleotides, which was 500 times more potent than unmodified RNA (Allerson, C. R. et al. *J. Med. Chem.* 2005, 48: 901-904; Koller, E. et al. *Nucl. Acids Res.* 2006 34: 4467-4476). However, such a high degree of improvement was not observed for other sequences.

These techniques present significant challenges, and there is a need for improvements in for example efficacy, in vivo stability and reduction of "off-target" effects (e.g., the silencing of a gene other than the intended target). There is therefore a continued need for improved oligonucleotide-based approaches.

The present description refers to a number of documents, the content of which is herein incorporated by reference in their entirety.

SUMMARY OF THE INVENTION

The invention relates to oligonucleotides, methods for their preparation and uses thereof, such as for decreasing the level of a target nucleic acid in a cell, and/or silencing the expression of a nucleic acid or gene of interest using small interfering RNA (siRNA) technologies.

In a first aspect, the present invention provides an oligonucleotide pair which can form a duplex, comprising:
  (a) a sense strand comprising (i) one or more DNA-like residues, (ii) one or more RNA-like residues, or (iii) both (i) and (ii); and
  (b) an antisense strand complementary to the sense strand, the antisense strand comprising (i) one or more DNA-like residues, (ii) one or more RNA-like residues, or (iii) both (i) and (ii).

In a further aspect, the present invention provides an oligonucleotide pair which can form a duplex, comprising a sense strand and an antisense strand complementary to the sense strand, wherein the oligonucleotide pair comprises: (a) one or more 2'-substituted arabinonucleotides (ANA); and (b) (i) one or more 2'-substituted ribonucleotides (RNA), (ii) one or more locked nucleic acid nucleotides (LNA), or (iii) a combination of (i) and (ii).

In an embodiment, the above-mentioned oligonucleotide pair comprises one or more 2'-substituted ANA and one or more 2'-substituted RNA. In another embodiment, the above-mentioned oligonucleotide pair comprises one or more 2'-substituted ANA and one or more LNA. In another embodiment, the above-mentioned oligonucleotide pair comprises one or more 2'-substituted ANA, one or more 2'-substituted RNA and one or more LNA.

In an embodiment, the above-mentioned 2'-substitutent is an halogen. In a further embodiment, the above-mentioned halogen is fluorine (F).

In an embodiment, the above-mentioned sense strand comprises: (i) 2'F-ANA only; (ii) 2'F-RNA only; (iii) a combination of 2'F-RNA and 2'F-ANA; (iv) RNA only; (v) a combination of 2'F-ANA and RNA; (vi) a combination of 2'F-ANA, RNA and LNA; or (vii) a combination of 2'F-ANA, 2'F-RNA and RNA.

In an embodiment, the above-mentioned antisense strand comprises: (i) 2'F-RNA only; (ii) RNA only; (iii) 2'F-ANA only; (iv) a combination of 2'F-RNA and 2'F-ANA; (v) a combination of 2'F-ANA and RNA; (vi) a combination of 2'F-ANA, RNA and LNA; or (vii) a combination of 2'F-ANA, 2'F-RNA and RNA.

In an embodiment, the above-mentioned sense strand and antisense strand have a length of 19 to 23 residues. In a further embodiment, the above-mentioned sense strand and antisense strand have a length of 21 residues.

In another embodiment, the above-mentioned sense strand, antisense strand, or both, comprises an overhang at the 3' end. In a further embodiment, the above-mentioned overhang is from 1 to 5 residues, in a further embodiment 2 residues.

In an embodiment, the above-mentioned overhang comprises deoxyribonucleotides (DNA), 2'F-ANA, or a combination thereof.

In an embodiment, the above-mentioned sense strand, antisense strand, or both, is/are phosphorylated at the 5' end. In a further embodiment, the above-mentioned antisense strand is phosphorylated at the 5' end.

In another aspect, the present invention provides a double-stranded siRNA-like molecule comprising the above-mentioned oligonucleotide pair.

In an embodiment, the above-mentioned sense and antisense strands are within an oligonucleotide of 15 to 80 nucleotides in length and such that the oligonucleotide or a portion thereof is capable of adopting an siRNA-like hairpin structure in which the sense and antisense strands form the stem of the hairpin structure.

In another aspect, the present invention provides a composition comprising the above-mentioned oligonucleotide pair or the above-mentioned double-stranded siRNA-like molecule, and a pharmaceutically acceptable carrier.

In another aspect, the present invention provides the above-mentioned oligonucleotide pair, the above-mentioned double-stranded siRNA-like molecule, or the above-mentioned composition, for decreasing the level of a target nucleic acid, or of a polypeptide encoded by said target nucleic acid, in a cell, wherein the sense strand of the oligonucleotide pair comprises a nucleobase sequence substantially identical to a nucleobase sequence of the target nucleic acid.

In another aspect, the present invention provides the above-mentioned oligonucleotide pair, the above-mentioned double-stranded siRNA-like molecule, or the above-mentioned composition, for preventing or treating a disease or condition associated with the expression of a target nucleic acid, or of a polypeptide encoded by said target nucleic acid, in a subject, wherein the sense strand of the oligonucleotide pair comprises a nucleobase sequence substantially identical to a nucleobase sequence of the target nucleic acid.

In another aspect, the present invention provides a method of degrading or decreasing the level of a target nucleic acid, or of decreasing the production or the level of a polypeptide encoded by said target nucleic acid, in a cell, the method comprising contacting the cell with the above-mentioned oligonucleotide pair, the above-mentioned double-stranded siRNA-like molecule, or the above-mentioned composition, wherein the sense strand of the oligonucleotide pair comprises a nucleobase sequence substantially identical to a nucleobase sequence of the target nucleic acid.

In another aspect, the present invention provides a method of preventing or treating a disease or condition associated with the expression of a target nucleic acid, or of a polypeptide encoded by said target nucleic acid, in a subject, the method comprising administering to the subject an effective amount of the above-mentioned oligonucleotide pair, the above-mentioned double-stranded siRNA-like molecule, or the above-mentioned composition, wherein the sense strand of the oligonucleotide pair comprises a nucleobase sequence substantially identical to a nucleobase sequence of the target nucleic acid.

In another aspect, the present invention provides a use of the above-mentioned oligonucleotide pair, the above-mentioned double-stranded siRNA-like molecule, or the above-mentioned composition, for degrading or decreasing the level of a target nucleic acid, or for decreasing the production or the level of a polypeptide encoded by said target nucleic acid, in a cell, wherein the sense strand of the oligonucleotide pair comprises a nucleobase sequence substantially identical to a nucleobase sequence of the target nucleic acid.

In another aspect, the present invention provides a use of the above-mentioned oligonucleotide pair, the above-mentioned double-stranded siRNA-like molecule, or the above-mentioned composition, for the preparation of a medicament, wherein the sense strand of the oligonucleotide pair comprises a nucleobase sequence substantially identical to a nucleobase sequence of the target nucleic acid.

In another aspect, the present invention provides a use of the above-mentioned oligonucleotide pair, the above-mentioned double-stranded siRNA-like molecule, or the above-mentioned composition, for preventing or treating a disease or condition associated with the expression of a target nucleic acid, or of a polypeptide encoded by said target nucleic acid, in a subject, wherein the sense strand of the oligonucleotide pair comprises a nucleobase sequence substantially identical to a nucleobase sequence of the target nucleic acid.

In another aspect, the present invention provides a use of the above-mentioned oligonucleotide pair, the above-mentioned double-stranded siRNA-like molecule, or the above-mentioned composition, for the preparation of a medicament for preventing or treating a disease or condition associated with the expression of a target nucleic acid, or of a polypeptide encoded by said target nucleic acid, in a subject, wherein the sense strand of the oligonucleotide pair comprises a nucleobase sequence substantially identical to a nucleobase sequence of the target nucleic acid.

In another aspect, the present invention provides a use of the above-mentioned oligonucleotide pair, the above-mentioned double-stranded siRNA-like molecule, or the above-mentioned composition, as a medicament.

In another aspect, the present invention provides a kit comprising the above-mentioned oligonucleotide pair, the above-mentioned double-stranded siRNA-like molecule, or the above-mentioned composition. In an embodiment, the above-mentioned kit further comprises instructions for inhibiting the expression of a target nucleic acid in a cell, degrading or decreasing the level of the target nucleic acid, or for decreasing the production or the level of a polypeptide encoded by the target nucleic acid.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

(FIG. 1A) Initial results (average of two transfections); (FIG. 1B) Confirmed activity of the most potent duplexes from (FIG. 1A), at lower concentrations (average of two transfections). In (FIG. 1A): black bars=2 nM, grey bars=10 nM and white bars=40 nM. In (FIG. 1B) black bars=0.4 nM, grey bars=2 nM and white bars=10 nM;

FIGS. 2A-2D show circular dichroism (CD) spectra of oligonucleotide duplexes jg1-jg15. (FIG. 2A) jg1-jg5, in which both strands have the same chemistry; (FIG. 2B) jg6-jg9, in which one of the two strands is a fully-modified chimeric strand; (FIG. 2C) jg10-jg13, in which one of the two strands is a fully-modified strand of a single chemistry; and (FIG. 2D) fully modified heteroduplexes jg14-jg15. The control duplex jg-1 (double-strand RNA) is included in all spectra for comparison. In (FIG. 2A) black line=jg-1, dashed line=jg-2, thin grey line=jg-3, thick grey line=jg-4, dotted line=jg-5. In (FIG. 2B) black line=jg-1, thick grey line=jg-6, thin grey line=jg-7, dotted line=jg-8, dashed line=jg-9. In (FIG. 2C) thick black line=jg-1, dashed line=jg-10, thin black line=jg-11, thick grey line=jg-12, dotted line=jg-13. In (FIG. 2D) black line=jg-1, dotted line=jg-14, dashed line=jg-15;

(FIG. 4A) siRNA transfections were performed in HEK293T cells using Lipofectamine Plus™ reagent on cells plated at 70-80% confluence in a 24-well plate. For each well, either 2.5 µl (1) or 5 µl of siRNA duplex (20 1-1M annealed duplex) was mixed with 50 µl of OPTI-MEM™ and 1 µl of Plus™ reagent and incubated for 5 min. at room temperature (RT). A mixture of 4 µl of Lipofectamine™ reagent and 50 µl of OPTI-MEM™ was then added to the precomplexed RNA mix and incubated for 20 min. at RT before adding to cells. Five hours later, the transfection medium was replaced by complete medium. Cells were harvested 48 hours after transfection and proteins were extracted for analysis by Western blotting using antibodies against 4E-BP1, 4E-BP2 or 13-actin.

(FIG. 9A) % gene expression relative to mock treatment following treatment with the indicated doses of various siRNA. (FIG. 9B) Survival rate of leukemia cells following siRNA treatment (y-axis represents number of leukemia cells still living after the indicated time periods after treatment with the indicated siRNA.

DISCLOSURE OF INVENTION

Figure 1A:
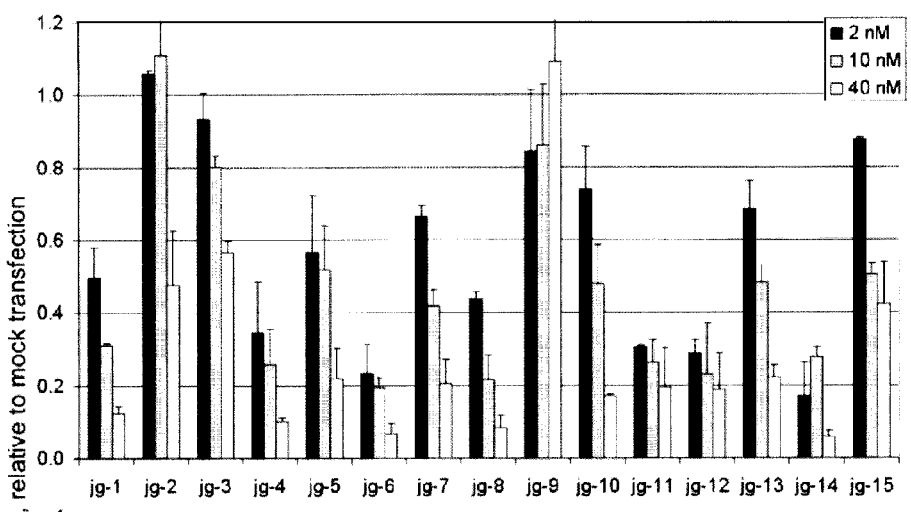
FIGS. 1A-1B shows siRNA activity of 2'-fluorinated duplexes targeting nucleotides 1818-1836 of firefly luciferase.

The invention relates to oligonucleotides and their uses, for example in various types of gene silencing approaches. In the studies described herein, the inventors have shown that chemically-modified siRNA, and more particularly oligonucleotide duplexes comprising one or more DNA-like and/or RNA-like nucleotides are able to mediate gene silencing.

Accordingly, in a first aspect, the present invention provides an oligonucleotide pair which can form a duplex, comprising:

(a) a sense strand comprising (i) one or more DNA-like residues, (ii) one or more RNA-like residues, or (iii) both (i) and (ii); and (b) an antisense strand complementary to the sense strand, the antisense strand comprising (i) one or more DNA-like residues, (ii) one or more RNA-like residues, or (iii) both (i) and (ii).

"DNA-like residue" as used herein in reference to conformation refers to a conformation of for example a modified nucleoside or nucleotide which is similar to the conformation of a corresponding unmodified DNA unit. DNA-like conformation may be expressed for example as having a southern or eastern pseudorotation (P) value. DNA-like nucleotides include for example 2'-deoxyribonucleotides, 2'-deoxy-2'-substituted arabinonucleotides such as 2'-deoxy-2'-fluoroarabinonucleotides (2'F-ANA or FANA), and corresponding phosphorothioate analogs. "RNA-like residue" as used herein in reference to conformation refers to a conformation of for example a modified nucleoside or nucleotide which is similar to the conformation of a corresponding unmodified RNA unit. RNA-like conformation may be expressed for example as having a northern P value. Further, RNA-like molecules tend to adopt an A-form helix while DNA-like molecules tend to adopt a 8-form helix. RNA-like nucleotides include for example RNA nucleotides, 2'-substituted-RNA nucleotides such as 2' Fluoro-RNA (2'F-RNA) nucleotides, locked nucleic acid (LNA) nucleotides (also defined as bridged nucleic acids or bicyclic nucleotides), 2'-fluoro-4'-thioarabinonucleotide (4'S-FANA nucleotides), 2'-O-alkyl-RNA and corresponding phosphorothioate analogs.

The structure of a representative DNA-like residue (2'F-ANA) is illustrated below:

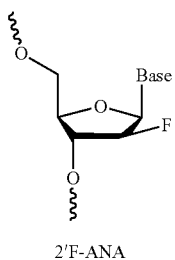

2'F-ANA

The structures of examples of RNA-like residues (RNA, LNA and 2'F-RNA) are illustrated below:

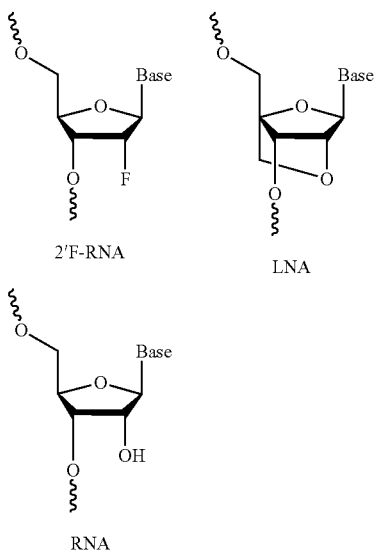

2'F-RNA

LNA

RNA

In a further aspect of the invention, an oligonucleotide pair is provided which can form a double-stranded duplex, for example:

Sense: DNA-like nucleotide(s), RNA-like nucleotide(s), or both
Antisense: DNA-like nucleotide(s), RNA-like nucleotide(s), or both Sense: DNA-like nucleotide(s), RNA-like nucleotide(s), or both
Antisense: RNA-like nucleotide(s)

Sense: DNA-like nucleotide(s)
Antisense: DNA-like nucleotide(s), RNA-like nucleotide(s), or both Sense: RNA-like nucleotide(s)
Antisense: DNA-like nucleotide(s), RNA-like nucleotide(s), or both Sense: DNA-like nucleotide(s)
Antisense: RNA-like nucleotide(s)

In another aspect, the present invention provides an oligonucleotide pair which can form a duplex comprising a sense (e.g., a first) strand and an antisense (e.g., a second) strand complementary to the sense (or first) strand, wherein the oligonucleotide duplex comprises:

(a) one or more 2'-substituted arabinonucleotides (ANA); and
(b) (i) one or more 2'-substituted ribonucleotides (RNA), (ii) one or more locked nucleic acid nucleotides (LNA), or (iii) a combination of (i) and (ii).

In an embodiment, the above-mentioned oligonucleotide duplex further comprises any combinations of DNA-like and/or RNA-like residues.

Oligonucleotides of the invention may include those which contain intersugar backbone linkages such as phosphotriesters, methyl phosphonates, short chain alkyl or cycloalkyl intersugar linkages or short chain heteroatomic or heterocyclic intersugar linkages, phosphorothioates and those with formacetal (O—CH$_2$—O), CH$_2$—NH—O—CH$_2$, CH$_2$—N(CH$_3$)—O—CH$_2$ (known as methylene(methylimino) or MMI backbone), CH$_2$—O—N(CH$_3$)—CH$_2$, CH$_2$—N(CH$_3$)—N(CH$_3$)—CH$_2$ and O—N(CH$_3$)—CH$_2$—CH$_2$ backbones (where phosphodiester is O—PO$_2$—O—CH$_2$). Oligonucleotides having morpholino backbone structures may also be used (U.S. Pat. No. 5,034,506). In alternative embodiments, antisense oligonucleotides may have a peptide nucleic acid (PNA, sometimes referred to as "protein nucleic acid") backbone, in which the phosphodiester backbone of the oligonucleotide may be replaced with a polyamide backbone wherein nucleosidic bases are bound directly or indirectly to aza nitrogen atoms or methylene groups in the polyamide backbone (Nielsen et al., *Science* 1991 254(5037): 1497-1500 and U.S. Pat. No. 5,539,082). The phosphodiester bonds may be substituted with structures which are chiral and enantiomerically specific. Persons of ordinary skill in the art will be able to select other linkages for use in practice of the invention.

"Nucleoside" refers to a base-sugar combination, the base being attached to the sugar via an N-glycosidic linkage. "Nucleotide" refers to a nucleoside that additionally comprises a phosphate group attached to the sugar portion of the nucleoside. "Base", "nucleic acid base" or "nucleobase" refer to a heterocyclic base moiety, which within a nucleoside or nucleotide is attached to the sugar portion thereof, generally at the 1' position of the sugar moiety, also known as the anomeric position. This term includes both naturally-occurring and modified bases. The two most common classes of naturally-occurring bases are purines and pyrimidines, and comprise for example guanine, cytosine, thymine, adenine and uracil. A number of other naturally-occurring bases, as well as modified bases, are known in the art, for example, inosine, 5-methylcytosine, 2-thiothymine, 4-thiothymine, 7-deazaadenine, 9-deazaadenine, 3-deazaadenine, 7-deazaguanine, 9-deazaguanine, 6-thioguanine, isoguanine, 2,6-diaminopurine, hypoxanthine, and 6-thiohypoxanthine.

Oligonucleotides of the invention may also include species which include at least one modified nucleotide base. Thus, purines and pyrimidines other than those normally found in nature may be used. Similarly, modifications on the pentofuranosyl portion of the nucleotide subunits may also be effected. Examples of such modifications includes 2'-substitution/modification, such as 2'-O-alkyl- and 2'-halogen-substituted nucleotides. Some specific examples of modifications at the 2' position of sugar moieties which are useful in the present invention are OH, SH, SCH$_3$, F, OCN, O(CH$_2$)$_n$ NH$_2$ or O(CH$_2$)$_n$ CH$_3$ where n is from 1 to about 10; C$_1$ to C$_{10}$ lower alkyl, substituted lower alkyl, alkaryl or aralkyl; Cl; Br; CN; CF$_3$; OCF$_3$; O-, S-, or N-alkyl; O-, S-, or N-alkenyl; SOCH$_3$; SO$_2$ CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by an acyclic sugar, by a sugar mimic such as cyclobutyl or by another moiety which takes the place of the sugar such as the six carbon hexose, or the seven carbon oxapane.

LNA generally refers to bicyclonucleotides and includes, for example, β-D, and α-L bicyclo nucleotides, bicyclo nucleotides such as xylo-locked nucleic acids (U.S. Pat. No. 7,084,125), L-ribo-locked nucleic acids (U.S. Pat. No. 7,053,207), 1'-2' locked nucleic acids (U.S. Pat. Nos. 6,734,291 and 6,639,059), 3'-5' locked nucleic acids (U.S. Pat. No. 6,083,482) as well as 2'-4' locked nucleic acids.

In some embodiments, the oligonucleotides in accordance with this invention may comprise from about 4 to about 100 nucleotide units, in further embodiments from about 10 to about 100, from about 4 to about 30, from about 10 to about 30, from about 18 to about 27, from about 19 to about 27, from about 18 to about 25, from about 19 to about 25, or from about 19 to about 23 nucleotide units, such as 19, 21 or 23 nucleotide units. As will be appreciated, a nucleotide unit is a base-sugar combination (or a combination of analogous structures) suitably bound to an adjacent nucleotide unit through phosphodiester or other bonds forming a backbone structure.

The heterocyclic base moiety of any nucleotides described herein may be one of the canonical bases of DNA or RNA, for example, adenine, cytosine, guanine, thymine or uracil. In other embodiments of the invention, some of the heterocyclic base moieties may be made up of modified or non-canonical bases, for example, inosine, 5-methylcytosine, 2-thiothymine, 4-thiothymine, 7-deazaadenine, 9-deazaadenine, 3-deazaadenine, 7-deazaguanine, 9-deazaguanine, 6-thioguanine, isoguanine, 2,6-diaminopurine, hypoxanthine, and 6-thiohypoxanthine.

In other embodiments of the invention, the oligonucleotide comprises one or more of the following internucleotide linkages: a) phosphodiester linkages; b) phosphotriester linkages; c) phosphorothioate linkages; d) methylphosphonate linkages; e) boranophosphate linkages; or f) 2',5'-phosphodiester linkages. In embodiments, the internucleotide linkages are phosphodiester linkages, phosphorothioate linkages or a combination thereof.

In an embodiment, the above-mentioned oligonucleotide pair or duplex comprises one or more 2'-substituted ANA and one or more 2'-substituted RNA (in one or both strands).

In another embodiment, the above-mentioned oligonucleotide pair or duplex comprises one or more 2'-substituted ANA and one or more LNA (in one or both strands).

In another embodiment, the above-mentioned oligonucleotide pair or duplex comprises one or more 2'-substituted ANA, one or more 2'-substituted RNA and one or more LNA (in one or both strands).

In embodiments, the DNA-like and RNA-like residues are in alternating segments within a strand, such as in an irregular fashion (whereby there may be differences in the number of residues per segment) or a regular fashion (whereby each segment has the same number of residues), or combinations thereof. In an embodiment, each alternating segment comprises one residue (referred to as 1-1 altimer design or configuration). In another embodiment, each alternating segment comprises two residues (referred to as 2-2 altimer design). In another embodiment, each alternating segment comprises three residues (referred to as 3-3 altimer design). In yet another embodiment, the above-mentioned alternating segments are in the sense strand.

In an embodiment, the above-mentioned oligonucleotide duplex comprises (in one or both strands) at least one 2'F-RNA residue. In a further embodiment, the above-mentioned 2'F-RNA residue is a 2'F-RNA pyrimidine. In another embodiment, the above-mentioned at least one 2'F-RNA residue is in the antisense strand.

In a further embodiment, the above-mentioned oligonucleotide pair or duplex is fully modified with one or more 2'F-RNA and 2'F-ANA residues. In another embodiment, the above-mentioned oligonucleotide duplex comprises (on one or both strands) a combination of one or more 2'F-RNA pyrimidines and 2'F-ANA purines. In another embodiment, the above-mentioned oligonucleotide duplex comprises (on one or both strands) one or more alternating segments of 2'F-RNA residues and 2'F-ANA residues (altimers), in a regular or irregular fashion. In a further embodiment, each segment comprises 1 to 5 residues. In a further embodiment, each segment comprises one residue (1-1 altimer design). In another embodiment, each segment comprises three residues (3-3 altimer design). In another embodiment, the above-mentioned oligonucleotide duplex comprises a mixture of 1-1 and 3-3 altimer designs. In another embodiment, the above-mentioned alternating segments of 2'F-RNA residues and 2'F-ANA residues (altimers) are on the sense strand.

In another embodiment, the above-mentioned oligonucleotide pair or duplex is fully modified with one or more 2'F-RNA residues, 2'F-ANA residues and LNA residues. In an embodiment, the one or more LNA residues are on both the sense strand and the antisense strand. In another embodiment, the one or more LNA residues are on the antisense strand. In another embodiment, the one or more LNA residues are on the sense strand.

In an embodiment, the above-mentioned sense strand comprises (i) 2'F-ANA; (ii) 2'F-RNA; (iii) RNA; (iv) LNA; (v) DNA; or (vi) any combination of (i) to (v).

In an embodiment, the above-mentioned antisense strand comprises (i) 2'F-ANA; (ii) 2'F-RNA; (iii) RNA; (iv) LNA; (v) DNA; or (vi) any combination of (i) to (v).

In an embodiment, the above-mentioned sense strand comprises:
 (i) 2'F-ANA only;
 (ii) 2'F-RNA only;
 (iii) a combination of 2'F-RNA and 2'F-ANA;
 (iv) RNA only;
 (v) a combination of 2'F-ANA and RNA;
 (vi) a combination of 2'F-ANA, 2'F-RNA, and RNA;
 (vii) a combination of 2'F-ANA, RNA and LNA.

In a further embodiment, the above-mentioned sense strand consists of:
 (i) 2'F-ANA only;
 (ii) 2'F-RNA only;
 (iii) a combination of 2'F-RNA and 2'F-ANA;
 (iv) RNA only;
 (v) a combination of 2'F-ANA and RNA;
 (vi) a combination of 2'F-ANA, 2'F-RNA, and RNA; or
 (vii) a combination of 2'F-ANA, RNA and LNA.

In another embodiment, the above-mentioned antisense strand comprises:
 (i) 2'F-RNA only;
 (ii) RNA only;
 (iii) 2'F-ANA only;
 (iv) a combination of 2'F-RNA and 2'F-ANA;
 (v) a combination of RNA and LNA; or
 (vi) a combination of 2'F-ANA, RNA and LNA.

In a further embodiment, the above-mentioned antisense strand consists of:
(i) 2'F-RNA only;
(ii) RNA only;
(iii) 2'F-ANA only;
(iv) a combination of 2'F-RNA and 2'F-ANA;
(v) a combination of RNA and LNA; or
(vi) a combination of 2'F-ANA, RNA and LNA.

In another embodiment, the above-mentioned oligonucleotide pair or duplex comprises:
(a) Sense: a combination of 2'F-RNA and 2'F-ANA
   Antisense: RNA only;
(b) Sense: a combination of 2'F-RNA pyrimidines and 2'F-ANA purines
   Antisense: RNA only;
(c) Sense: a combination of 2'F-RNA and 2'F-ANA in a 1-1 altimer design
   Antisense: RNA only;
(d) Sense: 2'F-ANA only
   Antisense: 2'F-RNA only;
(e) Sense: a combination of 2'F-RNA and 2'F-ANA in a 3-3 altimer design
   Antisense: RNA only;
(f) Sense: a combination of 2'F-RNA+2'F-ANA in 3-3 and 1-1 altimer designs
   Antisense: RNA only;
(g) Sense: a combination of 2'F-ANA and RNA
   Antisense: 2'F-RNA only;
(h) Sense: a combination of 2'F-RNA and 2'F-ANA in a 3-3 altimer design
   Antisense: 2'F-RNA only;
(i) Sense: a combination of 2'F-RNA and 2'F-ANA in 3-3 and 1-1 altimer designs
   Antisense: 2'F-RNA only;
(j) Sense: a combination of 2'F-RNA and 2'F-ANA in a 1-1 altimer design
   Antisense: 2'F-RNA only;
(k) Sense: 2'F-ANA only
   Antisense: a combination of RNA and LNA;
(l) Sense: a combination of 2'F-ANA and RNA
   Antisense: a combination of RNA and LNA;
(m) Sense: a combination of 2'F-ANA, RNA and LNA
   Antisense: RNA only;
(n) Sense: a combination of 2'F-ANA, RNA and LNA
   Antisense: a combination of RNA and LNA; or
(o) Sense: a combination of 2'F-ANA, RNA and LNA
   Antisense: 2'F-RNA only.

In a further embodiment, in the case of a sense strand comprising a 19 residue core (with or without an additional overhang), the sense strand comprises LNA residues at positions 3, 11, 16 and/or 17. In a further embodiment, in the case of an antisense strand comprising a 19 residue core (with or without an additional overhang), the antisense strand comprises LNA residues at position 19 (as read from 5' to 3').

In a further embodiment, the above-mentioned oligonucleotide pair or duplex comprises:
(a) Sense: $(2'F\text{-RNA pyrimidines})_x$ $(2'F\text{-ANA purines})_y$
   Antisense: $(RNA)_z$
      wherein x is the number of pyrimidines and y is the number of purines in the sense strand, and wherein x+y=z. In an embodiment z=19.
(b) Sense: $[(2'F\text{-ANA})(2'F\text{-RNA})]_9$ (2'F-ANA)
   Antisense: $(RNA)_{19}$
(c) Sense: $(2'F\text{-ANA})_{19}$
   Antisense: $(2'F\text{-RNA})_{19}$
(d) Sense: $[(2'F\text{-ANA})_3(2'F\text{-RNA})_3]_3$ (2'F-ANA)
   Antisense: $(RNA)_{19}$
(e) Sense: $[(2'F\text{-ANA})_3(2'F\text{-RNA})_3]_2$ $[(2'F\text{-ANA})(2'F\text{-RNA})]_3$ (2'F-ANA)
   Antisense: $(RNA)_{19}$
(f) Sense: $(2'F\text{-ANA})_{14}$ $(RNA)_5$
   Antisense: $(2'F\text{-RNA})_{19}$
(g) Sense: $[(2'F\text{-ANA})_3(2'F\text{-RNA})_3]_3$ (2'F-ANA)
   Antisense: $(2'F\text{-RNA})_{19}$
(h) Sense: $[(2'F\text{-ANA})_3(2'F\text{-RNA})_3]_2$ $[(2'F\text{-ANA})(2'F\text{-RNA})]_3$ (2'F-ANA)
   Antisense: $(2'F\text{-RNA})_{19}$
(i) Sense: $[(2'F\text{-ANA})(2'F\text{-RNA})]_9$ (2'F-ANA)
   Antisense: $(2'F\text{-RNA})_{19}$
(j) Sense: $(2'F\text{-ANA})_{19}$
   Antisense: (LNA) $(RNA)_{18}$
(k) Sense: $(2'F\text{-ANA})_{19}$
   Antisense: (LNA) (RNA) (LNA) $(RNA)_{16}$
(l) Sense: $(2'F\text{-ANA})_{19}$
   Antisense: $(RNA)_{11}$ $(LNA)_2$ $(RNA)_6$
(m) Sense: $(2'F\text{-ANA})(RNA)(LNA)(RNA)(2'F\text{-ANA})_4$ $(RNA)_2(LNA)(RNA)_2(2'F\text{-ANA})_2(LNA)(RNA)(2'F\text{-ANA})_2$
   Antisense: $(RNA)_{19}$
(n) Sense: $(2'F\text{-ANA})(RNA)(LNA)(RNA)(2'F\text{-ANA})_4$ $(RNA)_2(LNA)(RNA)_2(2'F\text{-ANA})(RNA)(2'F\text{-ANA})(LNA)(2'F\text{-ANA})(RNA)$
   Antisense: $(RNA)_{19}$
(o) Sense: $(2'F\text{-ANA})(RNA)(LNA)(RNA)(2'F\text{-ANA})_4$ $(RNA)_2(LNA)(RNA)_2(2'F\text{-ANA})(RNA)_5$
   Antisense: $(RNA)_{19}$
(p) Sense: $(2'F\text{-ANA})(RNA)(LNA)(RNA)(2'F\text{-ANA})_4$ $(RNA)_2(LNA)(RNA)_2(2'F\text{-ANA})_2(LNA)(RNA)(2'F\text{-ANA})_2$
   Antisense: $(LNA)(RNA)_{18}$
(q) Sense: $(2'F\text{-ANA})(RNA)(LNA)(RNA)(2'F\text{-ANA})_4$ $(RNA)_2(LNA)(RNA)_2(2'F\text{-ANA})(RNA)(2'F\text{-ANA})(LNA)(2'F\text{-ANA})(RNA)$
   Antisense: $(LNA)(RNA)_{18}$
(r) Sense: $(2'F\text{-ANA})(RNA)(LNA)(RNA)(2'F\text{-ANA})_4$ $(RNA)_2(LNA)(RNA)_2(2'F\text{-ANA})_2(RNA)_2(2'F\text{-ANA})_2$
   Antisense: $(LNA)(RNA)_{18}$
(s) Sense: $(2'F\text{-ANA})(RNA)(LNA)(RNA)(2'F\text{-ANA})_4$ $(RNA)_2(LNA)(RNA)_2(2'F\text{-ANA})(RNA)(2'F\text{-ANA})(RNA)(2'F\text{-ANA})(RNA)$
   Antisense: $(LNA)(RNA)_{18}$
(t) Sense: $(2'F\text{-ANA})(RNA)(LNA)(RNA)(2'F\text{-ANA})_4$ $(RNA)_2(LNA)(RNA)_2(2'F\text{-ANA})_2(RNA)_5$
   Antisense: $(LNA)(RNA)_{18}$
(u) Sense: $(2'F\text{-ANA})(RNA)(LNA)(RNA)(2'F\text{-ANA})_4$ $(RNA)_2(LNA)(RNA)_2(2'F\text{-ANA})_2(LNA)(RNA)(2'F\text{-ANA})_2$
   Antisense: $(2'F\text{-RNA})_{19}$
(v) Sense: $(2'F\text{-ANA})(RNA)(LNA)(RNA)(2'F\text{-ANA})_4$ $(RNA)_2(LNA)(RNA)_2(2'F\text{-ANA})(RNA)(2'F\text{-ANA})(LNA)(2'F\text{-ANA})(RNA)$
   Antisense: $(2'F\text{-RNA})_{19}$
(w) Sense: $(2'F\text{-ANA})(RNA)(LNA)(RNA)(2'F\text{-ANA})_4$ $(RNA)_2(LNA)(RNA)_2(2'F\text{-ANA})_2(RNA)_2(2'F\text{-ANA})_2$
   Antisense: $(2'F\text{-RNA})_{19}$
(x) Sense: $(2'F\text{-ANA})(RNA)(LNA)(RNA)(2'F\text{-ANA})_4$ $(RNA)_2(LNA)(RNA)_2(2'F\text{-ANA})(RNA)(2'F\text{-ANA})(RNA)(2'F\text{-ANA})(RNA)$
   Antisense: $(2'F\text{-RNA})_{19}$ or
(y) Sense: $(2'F\text{-ANA})(RNA)(LNA)(RNA)(2'F\text{-ANA})_4$ $(RNA)_2(LNA)(RNA)_2(2'F\text{-ANA})(RNA)_5$
   Antisense: $(2'F\text{-RNA})_{19}$.

In an embodiment, the above-mentioned oligonucleotide duplex comprises an overhang (e.g., a 5' and/or 3' overhang, on one strand or on both strands). In a further embodiment, the above-mentioned overhang is a 1 to 5 residues (e.g., nucleotides or modified nucleotides) overhang. In a further embodiment, the above-mentioned overhang is a 2 residues (e.g., nucleotides or modified nucleotides) overhang. For example, a 19 residue sense and/or antisense strand may comprise an overhang of an additional 1 to 5 residues. In such an example, a 2 residue overhang in both strands would result in sense and antisense strands of 21 residues each, 19 of which participate in base-pairing to form the duplex (the remaining 2 residues in each case representing the overhangs).

In another embodiment, the above-mentioned overhang comprises DNA, 2'F-ANA and/or 2'F-RNA residues. In a further embodiment, the above-mentioned overhang comprises two 2'F-ANA residues. In a further embodiment, the above-mentioned overhang comprising two 2'F-ANA residues is on the sense strand.

In another embodiment, the above-mentioned overhang comprises two 2'F-RNA residues. In a further embodiment, the above-mentioned overhang comprising two 2'F-RNA residues is on the antisense strand.

In another embodiment, the above-mentioned overhang is a 3' overhang.

In another embodiment, the above-mentioned oligonucleotide pair or duplex is 5' phosphorylated on one or both strands. In a further embodiment, the above-mentioned oligonucleotide pair or duplex is 5' phosphorylated on the antisense strand.

In embodiments, the sequence (e.g., nucleobase) complementarity between the sense strand and the antisense strand, or the sequence (e.g., nucleobase) identity between the sense strand and a target nucleic acid (e.g., mRNA), or a portion thereof, may be "perfect" or "complete" (100% complementarity or identity).

In embodiments, the complementarity between the sense strand and the antisense strand, or the identity between the sense strand and a target nucleic acid (e.g., mRNA), or a portion thereof), is substantial, for example greater than about 70%. For example, for a duplex region consisting of 19 base pairs, one mismatch results in 94.7% complementarity, two mismatches results in about 89.5% complementarity, 3 mismatches results in about 84.2% complementarity, 4 mismatches results in about 79% complementarity and 5 mismatches results in about 74% complementarity. Accordingly, as used herein, "complementary" refers to both perfect complementarity and substantial complementarity between two sequences, for example to complementarity of greater than about 70% between the sequences. In an embodiment, the sense strand has an identity of at least 12 nucleotides, in a further embodiment of at least 12 contiguous nucleotides, to at least a portion of a target nucleic acid (e.g., mRNA). In an embodiment, the sense strand has an identity of at least 13 nucleotides, in further embodiments of at least 14, 15, 16, 17 or 18 nucleotides (contiguous or not), to at least a portion of a target nucleic acid. In another embodiment, the sense strand has complete identity to a portion of a target mRNA, with the exception of overhanging nucleotides (3' overhang).

Also, complementarity and identity as used herein refers to complementarity and identity of the nucleobase moieties (e.g., A, C, G, T or U), commonly referred to as "base pairing", and is independent of for example modifications of the sugar moiety, such as those described herein. For example, a guanine nucleoside residue having any sugar moiety (i.e., modified or not) may base pair with a cytosine nucleoside residue similarly having any sugar moiety.

"Identity" refers to sequence similarity between two peptides or two nucleic acid molecules. Identity can be determined by comparing each position in the aligned sequences. A degree of identity between nucleic acid or between amino acid sequences is a function of the number of identical or matching nucleotides or amino acids at positions shared by the sequences. As the term is used herein, a nucleic acid sequence is "substantially identical" to another sequence if the functional activity of the sequences is conserved. Two nucleic acid sequences are considered substantially identical if, when optimally aligned (with gaps permitted), they share at least about 70% sequence similarity or identity, or if the sequences share defined functional motifs. In alternative embodiments, sequence similarity in optimally aligned substantially identical sequences may be at least 75%, 80%, 85%, 90% or 95%. An "unrelated" sequence shares less than 40% identity, though preferably less than about 25% identity, with a given reference sequence (e.g., a target nucleic acid).

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, or at least 95%. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215: 403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology, Vol. 1*, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

The sense strand and the antisense strand may be linked by a loop structure, which may be comprised of a non-nucleic acid polymer such as, inter alia, polyethylene glycol. Alternatively, the loop structure may be comprised of a nucleic acid, including modified and non-modified ribonucleotides and modified and non-modified deoxyribonucleotides.

In an embodiments, the 5'-terminus of the sense strand of the oligonucleotide duplex may be linked to the 3'-terminus of the antisense strand, or the 3'-terminus of the sense strand may be linked to the 5'-terminus of the sense strand, said linkage being via a nucleic acid linker typically having a length between 2 to 100 nucleotides (or modified nucleotides), preferably about 2 to about 30 nucleobases.

In an embodiment, the above-mentioned oligonucleotide duplex is a hairpin duplex, that is a single strand comprising the sense and antisense strands which is self-complementary and folds back onto itself.

The invention further provides a salt, such as a pharmaceutically acceptable salt, of any of the above-mentioned compounds (e.g., oligonucleotide, oligonucleotide duplex, siRNA or siRNA-like molecule) where applicable.

The present invention also relates to compounds which down-regulate expression of various genes, i.e., decrease production of an encoded polypeptide. The invention provides oligonucleotides/oligonucleotide duplexes of the invention and uses thereof in siRNA/RNAi applications, whereby expression of a nucleic acid encoding a polypeptide of interest, or a fragment thereof, may be inhibited or prevented using RNA interference (RNAi) technology, a type of post-transcriptional gene silencing. RNAi may be used to create a pseudo "knockout", i.e., a system in which the expression of the product encoded by a gene or coding region of interest is reduced, resulting in an overall reduction of the activity of the encoded product in a system. As such, RNAi may be performed to target a nucleic acid of interest or fragment or variant thereof, to in turn reduce its expression and the level of activity of the product which it encodes. Such a system may be used for functional studies of the product, as well as to treat disorders related to the activity of such a product. RNAi is described in for example U.S. patent publications Nos. 2002/0173478 (Gewirtz; published Nov. 21, 2002) and 2002/0132788 (Lewis et al.; published Nov. 7, 2002). Reagents and kits for performing RNAi are available commercially from for example Ambion Inc. (Austin, Tex., USA), New England Biolabs Inc. (Beverly, Mass., USA) and Invitrogen (Carlsbad, Calif., USA).

The initial agent for RNAi in some systems is thought to be dsRNA or modified dsRNA molecules corresponding to a target nucleic acid. The dsRNA is then thought to be cleaved into short interfering RNAs (siRNAs) which are for example 21-23 nucleotides in length (19-21 bp duplexes, each with 2 nucleotide 3' overhangs). The enzyme thought to effect this first cleavage step (the Drosophila version is referred to as "Dicer") is categorized as a member of the RNase III family of dsRNA-specific ribonucleases. Alternatively, RNAi may be effected via directly introducing into the cell, or generating within the cell by introducing into the cell an siRNA or siRNA-like molecule or a suitable precursor (e.g., vector encoding precursor(s), etc.) thereof. An siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced.

RNAi may be effected by the introduction of suitable in vitro synthesized siRNA or siRNA-like molecules into cells. RNAi may for example be performed using chemically-synthesized RNA or modified RNA molecules. Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g., using *E. coli* RNase III) in vitro to a size conducive to RNAi. The sense and antisense transcripts are combined to form an RNA duplex which is introduced into a target cell of interest. Other vectors may be used, which express small hairpin RNAs (shRNAs) which can be processed into siRNA-like molecules. Various vector-based methods have been described (see, e.g., Brummelkamp et al. [2002] Science 296: 550). Various methods for introducing such vectors into cells, either in vitro or in vivo (e.g. gene therapy) are known in the art.

Accordingly, in an embodiment of the invention, a nucleic acid, either a non-coding RNA (ncRNA) as well as an RNA encoding a polypeptide of interest (e.g. an mRNA), or a fragment thereof, may be inhibited by introducing into or generating within a cell an siRNA or siRNA-like molecule based on an oligonucleotide of the invention, corresponding to a nucleic acid of interest, or a fragment thereof, or to an nucleic acid homologous thereto (sometimes collectively referred to herein as a "target nucleic acid"). "Target nucleic acid" as used herein refers to a nucleic acid encoding a polypeptide (e.g., a coding RNA such as a mRNA), as well as to a non-coding nucleic acid, such as a non-coding RNA (ncRNA), i.e., an RNA that is not translated to a protein and which are involved in various cell functions including post-transcriptional modifications, gene regulation and propagation (virus). Examples of ncRNA include transfer RNA (tRNA), ribosomal RNA (rRNA) and small nuclear RNA (snRNA). As such, degradation and a decrease in level of the target nucleic acid may be effected, and in the case of a target nucleic which encodes a polypeptide, a decrease in the production or level of the polypeptide may be effected.

"siRNA-like molecule" refers to a nucleic acid molecule similar to an siRNA (e.g., in size and structure) and capable of eliciting siRNA activity, i.e., to effect the RNAi-mediated inhibition of production of the polypeptide. In various embodiments such a method may entail the direct administration of the siRNA or siRNA-like molecule into a cell. In an embodiment, the siRNA or siRNA-like molecule is less than about 30 nucleotides in length. In a further embodiment, the siRNA or siRNA-like molecule is about 19-23 nucleotides in length. In an embodiment, siRNA or siRNA-like molecule comprises a 19-21 bp duplex portion, each strand having a 2 nucleotide 3' overhang. In other embodiments, one or both strands may have blunt ends. In embodiments, the siRNA or siRNA-like molecule is substantially identical to a nucleic acid encoding a polypeptide of interest, or a fragment or variant (or a fragment of a variant) thereof. Such a variant is capable of encoding a protein having activity similar to the polypeptide of interest.

Accordingly, the present invention further provides a double-stranded siRNA or siRNA-like molecule (or modified siRNA) comprising an oligonucleotide duplex of the invention.

It is to be understood that, in the context of the present invention, any of the oligonucleotide duplexes or siRNA/siRNA-like molecules disclosed herein, or any long double-stranded RNA molecules (typically 25-500 nucleotides in length) which are processed by endogenous cellular complexes (such as Dicer or a counterpart thereof—see above) to form the siRNA molecules disclosed herein, or molecules which comprise the oligonucleotide duplexes or siRNA molecules disclosed herein, are within the scope of the present invention. For example, it is envisaged that a long oligonucleotide (e.g., of about 80 to 500 nucleotides in length) comprising one or more stem and loop structures, where stem regions comprise the oligonucleotides of the invention, may be delivered in a carrier, preferably a pharmaceutically acceptable carrier, and may be processed intracellularly by endogenous cellular complexes to produce one or more smaller double stranded oligonucleotides (siRNA/siRNA-like molecules) of the present invention. This oligonucleotide is typically referred to as a tandem shRNA construct.

In an embodiment, the above-mentioned siRNA is a 25 to 30 nucleotides, which may be substrates for the Dicer endonuclease (Kim D.-M. et al. *Nature Biotechnology*, vol. 23, pp. 222-226 (2005)).

The present invention also provides a composition (e.g., a pharmaceutical composition) comprising an oligonucleotide, oligonucleotide duplex or siRNA-like molecule of the invention, and an excipient or carrier, such as a biologically or pharmaceutically acceptable carrier or excipient. In one embodiment, such compositions include an oligonucleotide, oligonucleotide duplex or siRNA-like molecule of the invention in a therapeutically or prophylactically effective amount sufficient to treat a condition/disease associated with the expression (e.g., overexpression) of a target nucleic acid, and/or of a polypeptide encoded by a target nucleic acid. The therapeutic composition may be soluble in an aqueous solution at a physiologically acceptable pH.

As used herein "pharmaceutically acceptable carrier" or "excipient" includes any and all solvents, dispersion media, coatings, antibacterial and antifungal agents, isotonic and absorption delaying agents, and the like, that are physiologically compatible. In one embodiment, the carrier is suitable for parenteral administration. Alternatively, the carrier can be suitable for intravenous, intraperitoneal, intramuscular, topical, sublingual or oral administration, or for administration by inhalation. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, an oligonucleotide of the invention can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. an oligonucleotide, oligonucleotide duplex, siRNA, or siRNA-like molecule of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, an oligonucleotide of the invention may be formulated with one or more additional compounds that enhance its solubility.

Suitable methods for siRNA delivery to effect RNAi according to embodiments include any method by which a siRNA can be introduced into an organelle, a cell, a tissue or an organism, as described herein or as would be known to one of ordinary skill in the art. Such methods include, but are not limited to, direct delivery of siRNA such as by injection including microinjection, electroporation, calcium phosphate precipitation, using DEAE-dextran followed by polyethylene glycol, direct sonic loading, liposome-mediated transfection, microprojectile bombardment, agitation with silicon carbide fibers, Agrobacterium-mediated transformation, PEG-mediated transformation, desiccation/inhibition-mediated uptake, and the like. Through the use of techniques such as these, an organelle, cell, tissue or organism may be stably or transiently transformed. The oligonucleotide, double stranded molecule/duplex, siRNA molecule or composition of the invention may be delivered in liposome or lipofectin formulations and the like and are prepared by methods well known to those skilled in the art. Such methods are described, for example, in U.S. Pat. Nos. 5,593,972, 5,589,466, and 5,580,859.

Delivery systems aimed specifically at the enhanced and improved delivery of siRNA into mammalian cells have been developed (see, for example, Shen et al. *FEBS Let.* 2003, 539: 111-114; Xia et al., *Nat. Biotech.* 2002, 20: 1006-1010; Sorensen et al., *J. Mol. Biol.* 2003. 327: 761-766; Lewis et al., *Nat. Gen.* 2002, 32: 107-108 and Simeoni et al., *Nucleic Acids Research* 2003, 31(11): 2717-2724).

In accordance with another aspect of the invention, therapeutic compositions of the present invention, comprising an oligonucleotide duplex, siRNA, or siRNA-like molecule of the invention, may be provided in a kit or commercial package. The kit may further comprise instructions for the use of the oligonucleotide duplex, siRNA, or siRNA-like molecule for the inhibition of a target gene expression, and/or prevention and/or treatment of a disease/condition associated with expression (e.g., overexpression) of a target nucleic acid or gene. The kit may further comprise a validated positive control siRNA that targets a housekeeping gene and/or a validated negative control siRNA that is nontargeting. The kit may further comprise one or more reagents, such as reagents for introducing the oligonucleotide duplex, siRNA, or siRNA-like molecule of the invention into a cell (e.g., transfection/transformation reagents) and/or reagents for assessing knockdown of the intended target gene such as antibodies for monitoring knockdown at the protein level by immunofluorescence or Western analysis, reagents for assessing enzymatic activity or presence of a reporter protein, or reagents for assessing cell viability. RT-PCR primers and probes may be included for detection of target or reporter mRNA. The kit may further comprise a container (e.g., vial, test tube, flask, bottle, syringe or other packaging means) into which the oligonucleotide duplex, siRNA, or siRNA-like molecule may be placed/aliquoted, as well as devices for administering the oligonucleotide duplex, siRNA, or siRNA-like molecule to a subject (e.g., syringe).

The invention further provides a method of inhibiting the expression of a target gene/nucleic acid, or of degrading or decreasing the level of a target gene/nucleic acid, in a biological system (e.g., a cell, a tissue, an organ, a subject), e.g., to inhibit production of a polypeptide encoded by the target gene/nucleic acid, comprising introducing into the system the above-mentioned oligonucleotide duplex, siRNA or siRNA-like molecule.

According to another aspect of the invention, a method of inhibiting production of the product of a gene ("gene silencing"; e.g., of a deleterious gene) in a patient in need thereof is provided. "Gene silencing" as used herein refers to an inhibition or reduction of the expression of the protein encoded by a particular nucleic acid sequence or gene (e.g., a deleterious gene). The method comprises administering to the patient a therapeutically effective amount of oligonucleotide, a double stranded molecule/duplex, an siRNA molecule or a composition of the invention. In embodiments, the target gene or nucleic acid is a viral, bacterial or mammalian (e.g., human) gene.

The invention further provides a method of treating a condition associated with expression of a gene/nucleic acid in a subject, e.g., associated with the production of a polypeptide encoded by the target gene/nucleic acid, the method comprising administering the oligonucleotide duplex, siRNA or siRNA-like molecule to the subject (or to a cell, tissue, organ from the subject), wherein the siRNA or siRNA-like molecule is targeted to (or specific for) the gene/nucleic acid.

The invention further provides a use of the siRNA or siRNA-like molecule for the preparation of a medicament.

The invention further provides a use of the above-mentioned siRNA or siRNA-like molecule for a method selected from: (a) gene silencing; (b) inhibiting gene expression/polypeptide production in a biological system; (c) inhibiting gene expression/polypeptide production in a subject; (d) degrading or decreasing the level of a target gene/nucleic acid in a biological system or a subject; (d) treating a disease/condition associated with the production of a polypeptide encoded by a gene/nucleic acid in a subject; and (e) preparation of a medicament, for example a medicament for treating a disease or condition associated with expression (e.g., overexpression) of a nucleic acid/gene in a subject.

In various embodiments, an oligonucleotide pair, duplex, siRNA and/or siRNA-like molecule of the invention may be used prophylactically and/or therapeutically in formulations or medicaments to prevent or treat a disease/condition associated with the expression of a target nucleic acid or gene. The invention provides corresponding methods of medical treatment, in which a therapeutic dose of an oligonucleotide of the invention is administered in a pharmacologically acceptable formulation, e.g., to a patient or subject in need thereof.

A "therapeutically effective amount" refers to an amount effective, at dosages and for periods of time necessary, to achieve the desired therapeutic result, such as a reduction or reversal in progression of a disease associated with the production of a polypeptide encoded by a target nucleic acid or gene. A therapeutically effective amount of an oligonucleotide pair, duplex, siRNA and/or siRNA-like molecule of the invention may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or inhibiting the rate of onset or progression of a disease associated with the production of a polypeptide encoded by a target nucleic acid or gene. A prophylactically effective amount can be determined as described above for the therapeutically effective amount. For any particular subject, specific dosage regimens may be adjusted over time according to the individual need and the professional judgement of the person administering or supervising the administration of the compositions.

The invention further provides a use of an oligonucleotide, pair or duplex of the invention or the above-mentioned composition for degrading or decreasing the level of a target nucleic acid, or of decreasing the production or the level of a polypeptide encoded by a target nucleic acid or gene or for the prevention and/or treatment of a disease/condition associated with production of a polypeptide encoded by a target nucleic acid or gene. The invention further provides a use of an oligonucleotide of the invention for the preparation of a medicament. In an embodiment, the medicament is for prevention and/or treatment of a disease or condition associated with expression (e.g., overexpression) of a target nucleic acid or gene.

The target gene/nucleic acid can be a gene/nucleic acid derived from a cell, an endogenous gene, a transgene, or exogenous genes such as genes of a pathogen, for example, a virus, which is present in the cell after infection thereof. The cell having the target gene may be from the germ line or somatic, totipotent or pluripotent, dividing or non-dividing, parenchyma or epithelium, immortalized or transformed, or the like. The cell can be a gamete or an embryo; if an embryo, it can be a single cell embryo or a constituent cell or cells from a multicellular embryo. The term "embryo" thus encompasses fetal tissue. The cell having the target gene may be an undifferentiated cell, such as a stem cell, or a differentiated cell, such as from a cell of an organ or tissue, including fetal tissue, or any other cell present in an organism. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

The oligonucleotide pair, duplex, siRNA or siRNA-like molecule of the invention may be associated with, for example, a cell-targeting ligand. As used herein, a "cell targeting ligand" is a cell-directing molecule that has specificity for targeted sites such as cell surface receptors. This allows, for example, a more specific delivery of the oligonucleotide pair, duplex, siRNA or siRNA-like molecule to a particular cell/cell type, tissue or organ.

In another aspect, the present invention provides a method for increasing/improving the efficacy, potency and/or stability (e.g., in vivo stability) of an oligonucleotide duplex, comprising incorporating into said duplex (a) one or more 2'-substituted arabinonucleotides (ANA); and (b) (i) one or more 2'-substituted ribonucleotides (RNA), (ii) one or more locked nucleic acid nucleotides (LNA), or (iii) a combination of (i) and (ii).

In another aspect, the present invention provides a method for reducing off-target effects of an oligonucleotide duplex, comprising incorporating into said duplex (a) one or more 2'-substituted arabinonucleotides (ANA); and (b) (i) one or more 2'-substituted ribonucleotides (RNA), (ii) one or more locked nucleic acid nucleotides (LNA), or (iii) a combination of (i) and (ii).

The invention further provides a method of synthesizing an oligonucleotide of the invention, the method comprising: (a) 5'-deblocking; (b) coupling; (c) capping; and (d) oxidation; wherein (a), (b), (c) and (d) are repeated under conditions suitable for the synthesis of the oligonucleotide, wherein the synthesis is carried out in the presence of a suitable nucleotide monomer described herein (e.g., RNA, DNA, 2'F-ANA, 2'F-RNA, LNA).

The invention further provides a method to prepare an oligonucleotide duplex of the invention comprising combining a first (e.g., sense) strand comprising an oligonucleotide of the invention and a second (e.g., antisense) strand substantially complementary to the first strand under conditions permitting formation of a duplex via base-pairing between the first and second strands.

In embodiments, the synthesis is carried out on a solid phase, such as on a solid support selected from the group consisting of controlled pore glass, polystyrene, polyethylene glycol, polyvinyl, silica gel, silicon-based chips, cellulose paper, polyamide/kieselgur and polacryloylmorpholide. In further embodiments, the monomers may be used for solution phase synthesis or ionic-liquid based synthesis of oligonucleotides.

"5'-Deblocking" as used herein refers to a step in oligonucleotide synthesis wherein a protecting group is removed from a previously added nucleoside (or a chemical group linked to a solid support), to produce a reactive hydroxyl which is capable of reacting with a nucleoside molecule, such as a nucleoside phosphoramidite or H-phosphonate.

"Protecting group" as used herein refers to a moiety that is temporarily attached to a reactive chemical group to prevent the synthesis of undesired products during one or more stages of synthesis. Such a protecting group may then be removed to allow for step of the desired synthesis to proceed, or to generate the desired synthetic product. Examples of protecting groups are trityl (e.g., monomethoxytrityl, dimethoxytrityl), silyl, levulinyl and acetyl groups.

"Coupling" as used herein refers to a step in oligonucleotide synthesis wherein a nucleoside is covalently attached to the terminal nucleoside residue of the oligonucleotide (or to the solid support via for example a suitable linker), for example via nucleophilic attack of an activated nucleoside phosphoramidite, H-phosphonate, phosphotriester, pyrophosphate, or phosphate in solution by a terminal 5'-hydroxyl group of a nucleotide or oligonucleotide bound to a support. Such activation may be effected by an activating reagent such as tetrazole, 5-ethylthio-tetrazole, 4,5-dicyanoimidazole (DCI), and/or pivaloyl chloride.

"Capping" as used herein refers to a step in oligonucleotide synthesis wherein a chemical moiety is covalently attached to any free or unreacted hydroxyl groups on the support bound nucleic acid or oligonucleotide (or on a chemical linker attached to the support). Such capping is used to prevent the formation of for example sequences of shorter length than the desired sequence (e.g., containing deletions). An example of a reagent which may be used for such capping is acetic anhydride. Further, the capping step may be performed either before or after the oxidation (see below) of the phosphite bond.

"Oxidation" as used herein refers to a step in oligonucleotide synthesis wherein the newly synthesized phosphite triester or H-phosphonate diester bond is converted into pentavalent phosphate triester or diester bond. In the case where a phosphorothioate internucleotide linkage is desired, "oxidation" also refers to the addition of a sulfur atom to generate a phosphorothioate linkage.

The following examples are illustrative of various aspects of the invention, and do not limit the broad aspects of the invention as disclosed herein.

MODE(S) FOR CARRYING OUT THE INVENTION

The present invention is illustrated in further details by the following non-limiting examples.

Example 1: Materials and Methods

Oligonucleotide synthesis. Standard conditions for solid-phase oligonucleotide synthesis were used for the synthesis of all oligonucleotides, at a 0.8 to 1.0 μmol scale. 4,5-Dicyanoimidazole (0.50 M in acetonitrile) or 5-ethylthiotetrazole (0.25 M in acetonitrile) were used as activators, and 0.10 M iodine in 1:2:10 pyridine:water:THF was used as oxidant (wait time during the oxidation step was 24 seconds). Phosphoramidites were prepared as 0.15 M solutions (RNA amidites) or 0.08-0.10 M solutions (DNA, 2'-fluoro amidites). Coupling times were extended to 10-30 minutes for modified nucleotides. The oligonucleotides were treated with 3:1 ammonium hydroxide:ethanol for 16 h at 55° C. to cleave them from the solid support and deprotect the phosphates and bases. Sequences containing ribonucleotides were concentrated and desilylated with $Et_3N.3HF$ (100 μL) for 48 h at room temperature. Sequence purification was accomplished by anion exchange HPLC using 0-0.2 M $LiClO_4$ solution as eluent, or by preparative denaturing PAGE. Desalting was effected on Sephadex G-25 or NAP-25 columns. Sequence purity was verified using denaturing PAGE.

5'-phosphorylation of oligonucleotides was generally accomplished on the CPG solid support, by treating the newly-synthesized oligonucleotide with bis(2-cyanoethyl)-diisopropylaminophosphoramidite and ethylthiotetrazole, followed by normal deprotection conditions. ESI-MS was used to confirm the success of the phosphorylation reaction.

Thermal Denaturation and CD Studies.

Equimolar amounts of complementary sequences were combined, dried and rediluted in pH 7.2 buffer containing 140 mM KCl, 1 mM $MgCl_2$ and 5 mM $NaHPO_4$ (1 mL). After heating to 90° C., the samples were slowly cooled to room temperature and refrigerated overnight. They were then transferred into cold cuvettes in a Cary™ 300 UV spectrophotometer. The change in absorbance at 260 nm was then monitored upon heating from 15° C. to 90° C. Melting temperatures were determined as the maxima of the first derivatives or using the baseline method, as implemented in the Varian™ software.

CD spectra were obtained on a Jasco™ J-720 spectropolarimeter at 20° C. using samples annealed in the same buffer and under the same conditions as for the thermal denaturation studies. Spectra were baseline-corrected with respect to a blank containing the buffer but no duplex. Smoothing and adjustment for duplex concentration were effected using the Spectra-Manager program (Jasco).

siRNA Assays (Luciferase Inhibition).

HeLa X1/5 cells that stably express firefly luciferase were grown as previously described (Wu, H. et al. *J. Biol. Chem.* 1999, 274: 28270-28278). The day prior to transfection, $0.5 \times 10^5$ cells were plated in each well of a 24-well plate. The next day, the cells were incubated with increasing amounts of siRNAs premixed with lipofectamine-Plus™ reagent (Invitrogen) using 1 μL of lipofectamine and 4 μL of the plus reagent per 20 pmol of siRNA (for the highest concentration tested). For the siRNA titrations, each siRNA was diluted into dilution buffer (30 mM HEPES-KOH, pH 7.4, 100 mM KOAc, 2 mM $MgOAc_2$) and the amount of lipofectamine-plus reagent used relative to the siRNAs remained constant. 24 hours after transfection, the cells were lysed in hypotonic lysis buffer (15 mM $K_3PO_4$, 1 mM EDTA, 1% Triton, 2 mM NaF, 1 mg/ml BSA, 1 mM DTT, 100 mM NaCl, 4 μg/mL aprotinin, 2 μg/mL leupeptin and 2 μg/mL pepstatin) and the firefly light units were determined using a Fluostar Optima 96-well plate bioluminescence reader (BMG Labtech) using firefly substrate as described (Novac, O. et al. *J. Nucl. Acids Res.* 2004, 32: 902-915). The luciferase counts were normalized to the protein concentration of the cell lysate as determined by the DC protein assay (BioRad). Error bars represent the standard deviation of at least four transfections. Cotransfecting the siRNAs and the plasmid pCI-hRL-con expressing the *Renilla* luciferase mRNA (Pillai, R. S. et al. *Science* 2005, 309: 1573-1576) in the same cell line showed no difference in expression of this reporter, demonstrating the specificity of the RNAi effects.

Assessment of IFN Production Using the HEK-Blue™ IFN Detection Assay.

48 hours after siRNA transfection, cells were left untreated or treated with 1 ug/ml of poly(I:C) for 24 hours. The amount of IFN in the supernatant was measured according to the manufacturer's instructions (InvivoGen). Briefly, supernatants were mixed with HEK-Blue™ cells that carry a reporter gene expressing a secreted alkaline phosphatase under the control of the interferon stimulated response element 9 (ISRE9) promoter. In response to IFN exposure, the HEK-Blue™ cells release soluble alkaline phosphatase that is quantified by mixing the supernatant with Quanti Blue™ (InvivoGen) reagent and measuring the absorbance at 650 nm.

Example 2: siRNA Duplexes Containing Combinations of 2'F-ANA and 2'F-RNA

A series of duplexes containing fully-modified 2'F-ANA and 2'F-RNA strands were made (Table I). These duplexes target positions 1818-1836 of the firefly luciferase gene (RefSeq accession number M15077). A series of chimeric strands containing both 2'-fluoro epimers was also designed. One chimera consisted of 2'F-RNA pyrimidines and 2'F-ANA purines. Another pair of strands was a "1-1 altimer" structure, with alternating 2'F-ANA and 2'F-RNA residues. For all of these 2'F-ANA/2'F-RNA chimeric strands, the 3'-overhang was always made of 2'F-ANA.

TABLE I

Sequences of the siRNAs targeting positions 1818-1836 of firefly luciferase containing mixtures of 2'F-ANA and 2'F-RNA.

| Name | Description | Sequence | $T_m$ | SEQ ID NO: |
|---|---|---|---|---|
| jg-1 | RNA | 5'-GCUUGAAGUCUUUAAUUAAtt-3' | 61.8 | 19 |
|  | RNA | 5'-UUAAUUAAAGACUUCAAGCgg-3' |  | 20 |

TABLE I-continued

Sequences of the siRNAs targeting positions
1818-1836 of firefly luciferase
containing mixtures of 2'F-ANA and 2'F-RNA.

| Name | Description | Sequence | $T_m$ | SEQ ID NO: |
|------|-------------|----------|-------|------------|
| jg-2 | pur/pyr | 5'-G*CTT*GAAG*TCTTT*AATT*AATT-3' | 65.6 | 21 |
|  | pur/pyr | 5'-*TT*AAT*T*AAAGACTT*CAAG***GG-3' |  | 22 |
| jg-3 | 1-1 altimer | 5'-G*C*TT*G*AAG*T*C*TT*T*AA*T*T***AATT-3' | 36.8 | 23 |
|  | 1-1 altimer | 5'-*T*T*AA*T*T*AA*A*G*A*C*T*T*C*AAG*C*GG-3 |  | 24 |
| jg-4 | 2'F-RNA | 5'-*GCTTGAAGTCTTTAATTAATT*-3' | >90 | 25 |
|  |  | 5'-p*TTAATTAAAGACTTCAAGCGG*-3' |  | 26 |
| j9-5 | 2'F-ANA | 5'-GCTTGAAGTCTTTAATTAATT-3' | 72.8 | 27 |
|  |  | 5'-pTTAATTAAAGACTTCAAGCGG-3' |  | 28 |
| jg-6 | pur/pyr | 5'-G*CTTGAAG*TCTTTAATTAATT-3' | 62.5 | 21 |
|  | RNA | 5'-UUAAUUAAAGACUUCAAGCgg-3' |  | 20 |
| jg-7 | RNA | 5'-GCUUGAAGUCUUUAAUUAAtt-3' | 56.7 | 19 |
|  | pur/pyr | 5'-*TT*AATT*AAAGACTT*CAAG*GG-3' |  | 22 |
| jg-8 | 1-1 altimer | 5'-G*C*TT*G*AA*G*T*C*TT*T*AA*T*T*AATT-3' | 48.2 | 23 |
|  | RNA | 5'-UUAAUUAAAGACUUCAAGCgg-3' |  | 20 |
| jg-9 | RNA | 5'-GCUUGAAGUCUUUAAUUAAtt-3' | 45.8 | 19 |
|  | 1-1 altimer | 5'-*T*T*AA*T*T*AA*A*G*A*C*T*T*C*AAG*C*GG-3 |  | 24 |
| jg-10 | 2'F-RNA | 5'-*GCTTGAAGTCTTTAATTAATT*-3' | 76.5 | 25 |
|  | RNA | 5'-UUAAUUAAAGACUUCAAGCgg-3' |  | 20 |
| jg-11 | RNA | 5'-GCUUGAAGUCUUUAAUUAAtt-3' | 76.2 | 19 |
|  | 2'F-RNA | 5'-p*TTAATTAAAGACTTCAAGCGG*-3' |  | 26 |
| jg-12 | 2'F-ANA | 5'-GCTTGAAGTCTTTAATTAATT-3' | 64.7 | 27 |
|  | RNA | 5'-UUAAUUAAAGACUUCAAGCgg-3' |  | 20 |
| jg-13 | RNA | 5'-GCUUGAAGUCUUUAAUUAAtt-3' | 62.8 | 19 |
|  | 2'F-ANA | 5'-pTTAATTAAAGACTTCAAGCGG-3' |  | 28 |
| jg-14 | 2'F-ANA | 5'-GCTTGAAGTCTTTAATTAATT-3' | 80.1 | 27 |
|  | 2'F-RNA | 5'-p*TTAATTAAAGACTTCAAGCGG*-3' |  | 26 |
| jg-15 | 2'F-RNA | 5'-*GCTTGAAGTCTTTAATTAATT*--3' | 77.5 | 25 |
|  | 2'F-ANA | 5'-pTTAATTAAAGACTTCAAGCGG-3' |  | 28 |

Uppercase = RNA
Lowercase = dna
Uppercase bold underline = 2'F-ANA (FANA)
Uppercase bold italic = 2'F-RNA
p = 5'-Phosphate The RNAi activity of all duplexes was tested under the same conditions described above. Results are shown in FIG. 1.

Four of the duplexes (jg-6, jg-8, jg-10 and jg-12) contained a modified sense strand paired with an RNA antisense strand. The best of these four duplexes is jg-6, containing a purine/pyrimidine chimeric sense strand. The second-best duplex is duplex jg-8, containing the 1-1 altimer configuration in the sense strand. Thus, combining the two 2'-F epimers in the sense strand yields better results than using either chemistry alone, and strikingly, with better results relative to the natural RNA (jg-1).

Comparison of the RNAi activity of duplexes jg-6-jg-13 allows to evaluate the appropriateness of each type of modified strand architecture (2'F-ANA, 2'F-RNA, purine/pyrimidine and 1-1 altimer) in the sense or antisense strands. Sense/antisense preferences are observed for all four types of modified strands. Duplexes jg-6, jg-8 and jg-12 are more active than jg-7, jg-9 and jg-13, respectively, revealing that both chimeric constructs and the 2'F-ANA strand are better-tolerated in the sense strand than the antisense strand. The difference is particularly striking between duplexes jg-8 and jg-9 containing one 1-1 altimer strand; jg-8 (1-1 altimer in the sense strand) was one of the most active duplexes tested, while jg-9 (1-1 altimer in the antisense strand) was inactive.

Figure 1B:
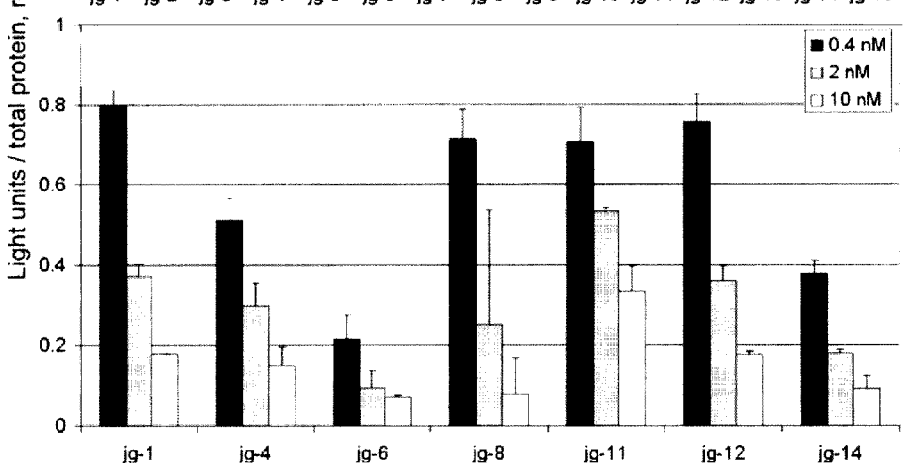

FIG. 1 shows that jg-11 is more active than jg-10, thus suggesting that 2'F-RNA is better-tolerated in the antisense than the sense strand. It is believed that this is the first time a fully-modified or heavily-modified strand has been observed to be better tolerated in the antisense than the sense strand.

A 2'F-ANA sense strand and a 2'F-RNA antisense strand formed a duplex that was found to be active as well. Indeed, synergy between these two modifications is observed in the case of duplex jg-14, which is more active than either of the duplexes jg-11 or jg-12 from which it is derived. On the other hand, reversing the sense/antisense combination gave jg-15, one of the least potent siRNAs tested in this study.

The thermal stabilities of the duplexes were tested by heating the annealed duplexes, in physiological buffer, and measuring the change in the absorbance at 260 nm ($A_{260}$). Binding affinities of the modified duplexes vary widely. There was no correlation between RNAi activity and binding affinity. For example, two of the most active duplexes we tested were jg-4 and jg-8, with $T_m$ values of >90° C. and 48.2° C., respectively. The most potent duplex, the fully fluorinated heteroduplex jg-14, had a $T_m$ about 20° C. higher than that that of native RNA duplex (80.1° C. vs 61.8° C.).

The CD spectra of the modified duplexes were examined, to explore possible connections between helical structure and siRNA activity. Results are presented in FIG. 2. The changes in the Cotton effects at 210-220 nm are noteworthy. Beginning with duplexes jg-2-jg-5, which have the same chemistry in both strands, it is noteworthy that for 2'F-RNA duplex jg-4, this band is of maximum intensity at 227 nm, which is slightly redshifted with respect to the control duplex jg-1 (224 nm). On the other hand, for the three duplexes containing 2'F-ANA, including the two chimeric architectures jg-2 and jg-3 and the all-2'F-ANA duplex jg-5, this band is blueshifted and reaches maximum intensity at about 220 nm. Furthermore, duplexes jg-1 and jg-4 feature a more strongly negative band at 210 nm. This is consistent with the degree of A-form helicity of the duplexes (Ratmeyer, L. et al. *Biochemistry* 1994, 33: 5298-5304). 2'F-RNA duplex jg-4 also has the highest intensity for its 270 nm band, followed by native RNA duplex jg-1, then the 2'F-ANA-containing strands. Fully-2'F-ANA duplex jg-5 is quite B-form in character, as evidenced by the fact that its 270 nm band is of the lowest intensity and contains a shoulder above 280 nm, and its 245 nm negative band is significantly more negative than the other duplexes (Ratmeyer, L. et al. 1994, supra).

For duplexes jg-6-jg-13, a modified sense strand corresponded to higher molar ellipticity at 220 nm than was observed for the native and antisense-modified duplexes. Thus, the intensity of the 220 nm band for the various sense antisense pairs jg-6/jg-7, jg-8/jg-9, jg-10/jg-11 and jg-12/jg-13 was always higher for the first member of each pair. Because sense modification led to higher potency for 3 of the 4 modified strand architectures, this higher intensity also corresponded with higher potency, with the exception of duplexes jg-10 and jg-11, for which the 2'F-RNA-modified strand was better-accepted in the antisense than the sense. It is also interesting that modifying the sense strand, but not the antisense strand, with 2'F-RNA, led to a notable increase in the intensity of the Cotton effects at 270 nm.

For duplexes jg-14 and jg-15, in which both strands were modified, the more potent duplex jg-14 featured higher intensity for its 220 nm band, and indeed, in the whole range from 205-250 nm. It is not clear why such a large difference is observed between these two duplexes at lower wavelengths. Duplex jg-15 should have more A-form character since it has more strongly negative peaks at 210 nm, but the higher $T_m$ of jg-14 implies that it has more A-form character than jg-15 (Ratmeyer, L. et al. 1994, supra).

To investigate whether the potency and synergy obtained for 2'F-ANA-2'F-RNA combinations was applicable to other siRNA sequences, other duplexes directed against the same gene and cell line, this time targeting positions 515-533 (Hoshika, S. et al. *FEBS Lett.* 2005, 579: 3115-3118; Elbashir, S. M. at al. *Nature* 2001, 411: 494-498). A series of fully or heavily 2'-fluorinated duplexes was designed, with the following principles in mind:

(a) The preference of 2'F-ANA and 2'F-ANA-2'F-RNA chimeras for the sense strand, and of 2'F-RNA for the antisense strand;
(b) The low binding affinity of 1-1 altimers of 2'F-ANA and 2'F-RNA (duplexes jg-8 and jg-9 had $T_m$ values 13-16° C. lower than the control sequence, see Table I;
(c) The activity of a fully-modified 2'F-ANA sense strand was compared with that of a "fr-type" 2'F-ANA sense strand, which includes five RNA inserts near its 3'-end, when paired with a 2'F-RNA antisense strand.

The resulting duplexes are presented in Table II. Each of two antisense strands (either RNA or 2'F-RNA) was paired with each of six modified sense strands (2'F-ANA or a 2'F-ANA-2'F-RNA chimera). The potency of these strands to induce RNAi was evaluated and the results are presented in FIG. 3.

TABLE II

Sequences of siRNAs targeting positions 515-533 of firefly luciferase with combinations of 2'F-ANA and 2'F-RNA.

| Name | Description | Sequence | SEQ ID NO: |
|---|---|---|---|
| kl-ctl | RNA | 5'-CGUACGCGGAAUACUUCGAtt-3' | 29 |
|  | RNA | 5'-UCGAAGUAUUCCGCGUACGtt-3' | 30 |
| kl-1 | 2'F-RNA | 5'-*CGUACGCGGAAUACUUCGAUU*-3' | 31 |
|  | RNA | 5'-UCGAAGUAUUCCGCGUACGtt-3' | 30 |
| kl-2 | 2'F-ANA | 5'-CGTACGCGGAATACTTCGATT-3' | 32 |
|  | RNA | 5'-UCGAAGUAUUCCGCGUACGtt-3' | 30 |
| kl-3 | "fr" type | 5'-CGTACGCGGAATACUUCGATT-3' | 33 |
|  | RNA | 5'-UCGAAGUAUUCCGCGUACGtt-3' | 30 |
| kl-4 | 3-3 altimer | 5'-CGTACGCGGAA*U*AC*T*UCGATT-3' | 34 |
|  | RNA | 5'-UCGAAGUAUUCCGCGUACGtt-3' | 30 |
| kl-5 | 3-3/1-1 alt | 5'-CGTACGCGGAAU*A*C*T*UCGATT-3' | 35 |
|  | RNA | 5'-UCGAAGUAUUCCGCGUACGtt-3' | 30 |
| kl-6 | 1-1 altimer | 5'-CGT*A*CGCGG*A*A*U*A*C*T*U*CGATT-3' | 36 |
|  | RNA | 5'-UCGAAGUAUUCCGCGUACGtt-3' | 30 |

TABLE II-continued

Sequences of siRNAs targeting positions
515-533 of firefly luciferase with
combinations of 2'F-ANA and 2'F-RNA.

| Name | Description | Sequence | SEQ ID NO: |
|---|---|---|---|
| kl-7 | 2'F-RNA | 5'-*CGUACGCGGAAUACUUCGAUU*--3' | 31 |
|  | 2'F-RNA | 5'-p*UCGAAGUAUUCCGCGUACGUU*-3' | 37 |
| kl-8 | 2'F-ANA | 5'-CGTACGCGGAATACTTCGATT-3' | 32 |
|  | 2'F-RNA | 5'-p*UCGAAGUAUUCCGCGUACGUU*-3' | 37 |
| kl-9 | "fr" type | 5'-CGTACGCGGAATACUUCGATT-3' | 33 |
|  | 2'F-RNA | 5'-p*UCGAAGUAUUCCGCGUACGUU*-3' | 37 |
| kl-10 | 3-3 altimer | 5'-CGTACGCGG*AAU*ACT*U*CGATT-3' | 34 |
|  | 2'F-RNA | 5'-p*UCGAAGUAUUCCGCGUACGUU*--3' | 37 |
| kl-11 | 3-3/1-1 alt | 5'-CGTACGCGGA*AU*AC*U*CGATT-3' | 35 |
|  | 2'F-RNA | 5'-p*UCGAAGUAUUCCCGCGUACGUU*-3' | 37 |
| kl-12 | 1-1 altimer | 5'-*CG*TAC*GC*GG*AAU*AC*U*CGATT-3' | 36 |
|  | 2'F-RNA | 5'-p*UCGAAGUAUUCCGCGUACGUU*-3' | 37 |

Figure 3:
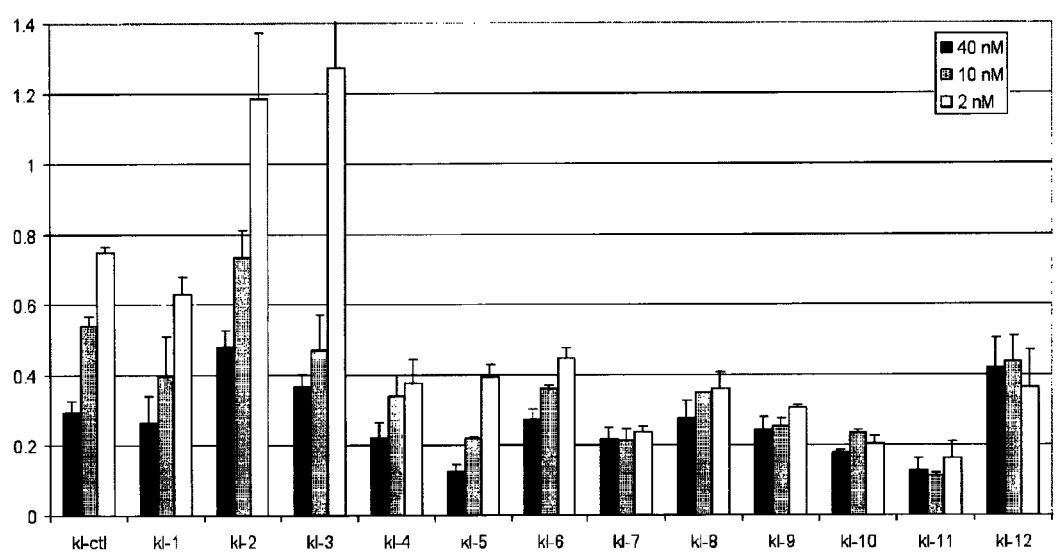
FIG. 3 shows siRNA activity of 2'-fluorinated duplexes targeting nucleotides 515 to 533 of firefly luciferase. Black bars=40 nM, grey bars=10 nM and white bars=2 nM.

Uppercase = RNA
Lowercase = dna
Uppercase bold underline = 2'F-ANA (FANA)
Uppercase bold italic = 2'F-RNA
p = 5'-Phosphate Several results are clear from this set of duplexes. As shown in FIG. 3, nearly all of the duplexes are more effective the control siRNA. Four fully-modified duplexes (kl-7, kl-9, kl-10, kl-11) and five other heavily-modified duplexes (kl-4, kl-5, kl-6, kl-8, kl-12) have greater potency than the control for this second sequence of the firefly luciferase.

Furthermore, synergy between 2'F-RNA and 2'F-ANA is again visible. These duplexes can be thought of as belonging to two sub-series, the first with an RNA antisense strand (kl-1 to kl-6) and the second with a 2'F-RNA antisense strand (kl-7 to kl-12). Comparing the corresponding members of each series (kl-1 to kl-7, kl-2 to kl-8, etc), it is clear that all of the modified sense strands show better potency when paired to a 2'F-RNA antisense strand than an RNA antisense strand.

Taking each sub-series separately, and ranking the duplexes in order of potency, a pattern can be observed: the sense strands follow the same order, with either antisense strand. Thus, the "worst" sense strand is all 2'F-ANA (kl-2 and kl-8), followed by the "fr-type" sense strand containing five RNA inserts (kl-3 and kl-9). It should be noted, however, that both kl-8 and kl-9 are nonetheless more potent than the control.

Use of the chimeric 2'F-ANA-2'F-RNA sense strands led to better potency, again irrespective of the antisense strand used. The best sense strand was the 3-3/1-1 altimer strand (kl-5 and kl-11), suggesting that rational design for controlling thermodynamic bias does indeed improve potency. Duplex kl-11 was unsurpassed in both potency and efficacy. It is not possible even to estimate an $IC_{50}$ value for this duplex, since at 2 nM, the lowest concentration used for these transfections, the silencing is still at its maximal level.

Finally, it is worth noting that both duplexes kl-7 and kl-11 seem to be silencing at their maximum efficacy, since the dose response is essentially flat. The chimeric sense strand of kl-11 thus allows higher efficacy silencing (relative luciferase level of 0.12-0.15 instead of 0.21-0.24).

As described herein, for example 2'F-ANA and 2'F-RNA can be combined in various ways in siRNA duplexes. For example, two types of combinations of these two modifications lead to increased potency: combining both chemistries in the sense strand, and combining an 2'F-RNA antisense strand with a 2'F-ANA or chimeric sense strand. Examples of both of these types of synergistic combinations led to increased potency.

Example 3: Knockdown of 4E-BP1/2 Using Specific siRNA Duplexes Containing Combinations of 2'F-ANA and 2'F-RNA and Effects on Type-I IFN Production The sequences of the siRNAs used in the 4E-BP inhibition studies described herein are provided in Table III.

TABLE III

Sequences of the siRNAs used in the 4E-BP
inhibition studies described herein

| Sequence | Oligo ID | siRNA duplex ID | SEQ ID NO: |
|---|---|---|---|
| 5' AACUCACCUGUGACCAAAAca | 4EBP-1 HS | Unmodified Control | 1 |
| 5' UUUUGGUCACAGGUGAGUUcc | 4EBP-1 HAS | 4EBP-1 Human | 2 |

TABLE III-continued

Sequences of the siRNAs used in the 4E-BP
inhibition studies described herein

| Sequence | Oligo ID | siRNA duplex ID | SEQ ID NO: |
|---|---|---|---|
| 5' AAGACUCCAAAGUAGAAGUaa | 4EBP-2 HS | Unmodified Control 4EBP- | 3 |
| 5' ACUUCUACUUUGGAGUCUUca | 4EBP-2 HAS | 2 Human and Murine | 4 |
| 5' AACUCACCUGUGGCCAAAACa | 4EBP-1 MS | Unmodified Control | 5 |
| 5' UUUUGGCCACAGGUGAGUUcc | 4EBP-1 MAS | 4EBP-1 Murine | 6 |
| 5' AACTCACCTGTGGCCAAAACA | 4EBP-1 MS_JG14 | 4EBP-1 Murine_14 | 7 |
| 5' *pUUUUGGCCACAGGUGAGUUCC* | 4EBP-1 MAS_JG14 | | 8 |
| 5' AACTCACCTGTGACCAAAACA | 4EBP-1 HS_JG14 | 4EBP-1 Human_14 | 9 |
| 5' *pUUUUGGUCACAGGUGAGUUCC* | 4EBP-1 HAS_JG14 | | 10 |
| 5' AAGACTCCAAAGTAGAAGTAA | 4EBP-2 MS_JG14 | 4EBP-2 Mouse_14 or | 11 |
| 5' *pACUUCUACUUUGGAGUCUUCA* | 4EBP-2 MAS_JG14 | 4EBP-2 Human_14 | 12 |
| 5' AA*CU*CACCT*GUGG*CC*A*AAACA | 4EBP-1 MS_611 | 4EBP1 Mouse_611 | 13 |
| 5' *pUUUUGGCCACAGGUGAGUUCC* | 4EBP-1 MAS_611 | | 14 |
| 5' AA*CU*CACCT*GUGA*CC*A*AAACA | 4EBP-1 HS_611 | 4EBP1 Human_611 | 15 |
| 5' *pUUUUGGUCACAGGUGAGUUCC* | 4EBP-1 HAS_611 | | 16 |
| 5' AAGA*CU*CCAAAG*UAGA*AGTAA | 4EBP-2 MS_611 | 4EBP2 Mouse_611 or | 17 |
| 5' *pACUUCUACUUUGGAGUCUUCA* | 4EBP-2 MAS_611 | 4EBP2 Human_611 | 18 |

Figure 4A:
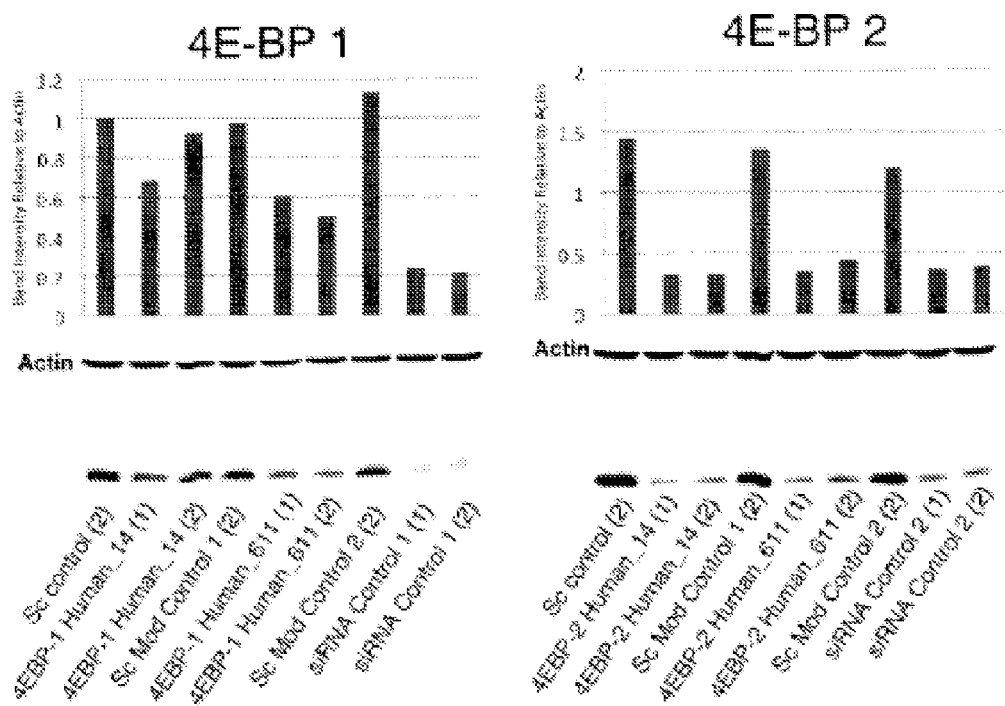
FIG. 4A shows the effect of small-interfering RNA (siRNA) transfections on eiF4E binding protein (4E-BP) 1 or 4E-BP2 expression.

Uppercase = RNA
Lowercase = dna
Uppercase bold underline = 2'F-ANA (FANA)
Uppercase bold italic = 2'F-RNA
p = 5'-Phosphate The results presented at FIG. 4A indicate that unmodified siRNAs targeting human 4E-BP1 and 4E-BP2 are eliciting potent gene silencing (far right lanes in the two gels). As well, none of the scrambled (non-targeting) siRNAs affect expression levels of 4E-BP1 or 4E-BP2. Because Scrambled modified control 1 and 2 are chemically modified with 2'F-ANA and 2'F-RNA, these data indicate that the chemical modifications alone are not responsible for changes in expression of 4E-BP1 or 2. Looking at the knockdown of 4E-BP1 and 2 with the _14 modification architecture (fully 2'F-ANA sense strand, fully 2'F-RNA antisense strand), it is shown that siRNAs comprising this modification are capable of silencing both 4E-BP1 and 2, although not as potently as the unmodified control after 24 hours, especially in the case of 4E-BP1. The _611 modification architecture (alternating 2'F-ANA/2'F-RNA sense strand, fully 2'F-RNA antisense strand) appears to be more potent than _14 in both cases, possibly even exceeding the potency of the unmodified control for 4E-BP2.

Figure 5:
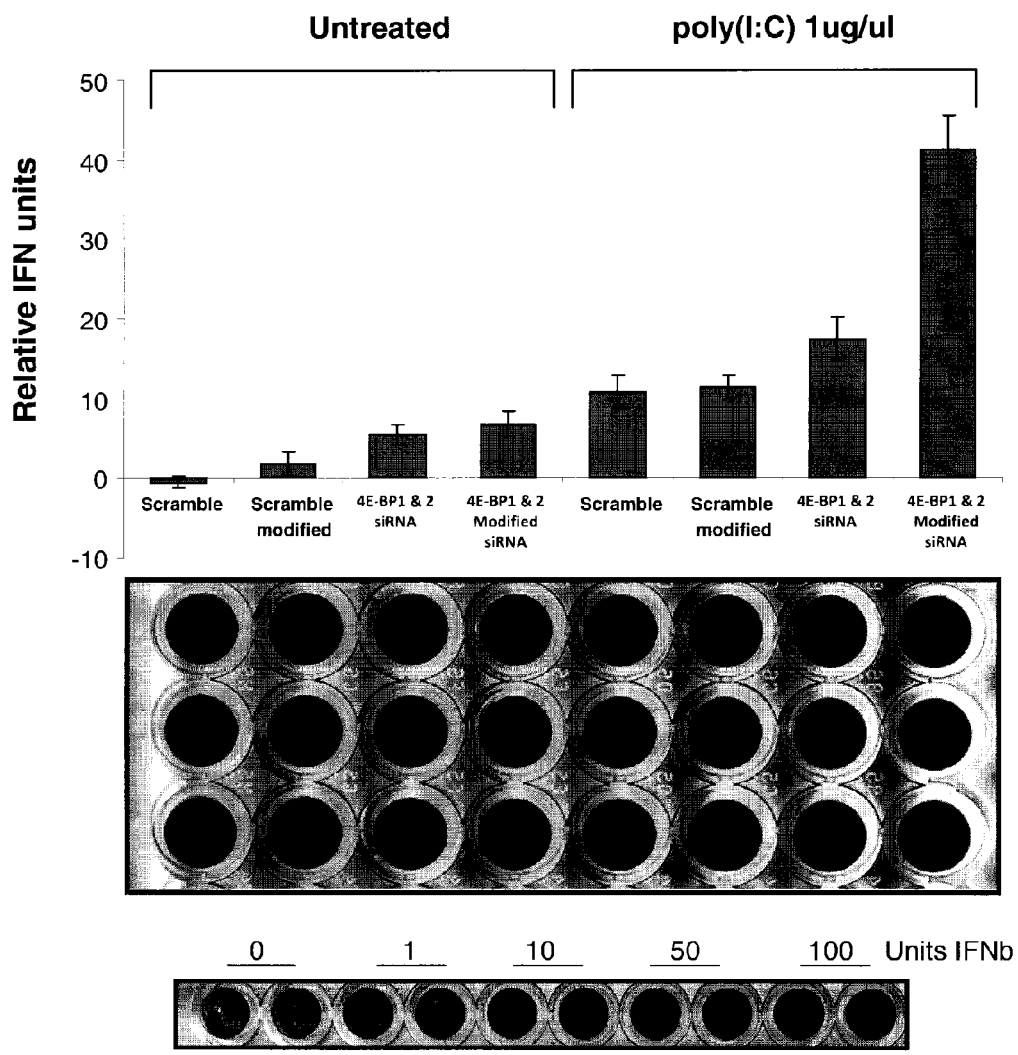
FIG. 5 shows the effect of siRNA transfections on IFN production by HEK293T cells following stimulation with poly(I:C). siRNA transfections were performed in HEK293T cells using Lipofectamine Plus™ reagent on cells plated at 70-80% confluence in a 24-well plate. For each well, 5 µl of both 4E-BP1 and 4E-BP2 siRNA duplexes (modified H-611 or unmodified) (20 1-1M annealed duplex) were mixed with 75 µl of OPTI-MEM™ and 1 µl of Plus™ reagent and incubated for 5 min. at room temperature (AT). A mixture of 5 µl of Lipofectamine™ reagent and 75 µl of OPTI-MEM™ was then added to the precomplexed RNA mix and incubated for 20 min. at AT before adding to cells. Five hours later, the transfection medium was replaced by complete medium. 48 hours after transfection, cells were either left untreated or treated with 1 µg/ml of poly(I:C) for 24 hours. Supernatants from untreated and treated cells were collected and the amount of IFN was quantified using the HEK-Blue™ IFN-α/β Cells (InvivoGen, San Diego, USA) according to the manufacturers protocol.

The ability of chemically modified siRNAs to reproduce the 4E-BP1/2 double knockout phenotype was next determined using the HEK-Blue™ system according to the manufacturer's protocol (InvivoGen). The results of experiments performed to monitor the relative levels of interferon 3 days post-siRNAs transfection and in the presence or absence of poly(I:C) are presented in FIG. 5. When cells are treated with modified scrambled siRNA and poly(I:C), the relative IFN levels are similar to that of cells treated with unmodified scrambled sequence, showing the modification does not trigger a significant immunostimulatory response. In the case of treatment of cells with unmodified siRNAs targeting both 4E-BP1 and 2 at the same time, the relative levels of IFN in the cells increase to around 5 units in the absence of poly(I:C). When the cells were treated with poly(I:C) (a trigger of IFN production via RIG-I and MDA5 receptors), relative IFN levels are around 18, versus about 11 in scrambled siRNA treated cells, demonstrating that silencing 4E-BP1 and 2 increases the IFN response, similar to our observations in 4E-BP1/2 knockout mice. Finally, treatment with fully modified siRNA (corresponding to the _611 architecture) against 4E-BP1 and 2 in the presence of poly(I:C) results in relative IFN levels of about 42 units, which is a 4-fold increase as compared to scrambled treated cells, and a 2-fold increase as compared to cells treated with regular unmodified 4E-BP1 and 2 siRNA.

Example 4: Luciferase Knockdown Using siRNA Duplexes Containing 2'F-ANA and LNA

It was next tested whether 2'F-ANA could act synergistically with another RNA analog adopting northern sugar pucker, namely locked nucleic acid (LNA). LNA is locked into a rigid northern sugar conformation by a methylene bridge.

The first series, referred to as "L-FL", were designed by combining 2'F-ANA sense strands with antisense strands containing 2'F-ANA overhangs and LNA inserts at positions previously observed to have RNAi activity. The sequences of the duplexes of the L-FL series are provided in Table IV.

TABLE IV

Sequences of the siRNAs of the L-FL series used in the experiments described herein

| Sequence | Strand label | siRNA label | SEQ ID NO: |
|---|---|---|---|
| 5'-GCTTGAAGTCTTTAATTAATT-3' | 303g | L-FL1 | 27 |
| 5'-pUUAAUUAAAGACUUCAAGcGG-3' | GD2 | | 38 |

TABLE IV-continued

Sequences of the siRNAs of the L-FL series used in the experiments described herein

| Sequence | Strand label | siRNA label | SEQ ID NO: |
|---|---|---|---|
| 5'-GCTTGAAGTCTTTAATTAATT-3'<br>5'-pUUAAUUAAAGACUUCAaGcGG-3' | 303g<br>GD3 | L-FL2 | 27<br>39 |
| 5'-GCTTGAAGTCTTTAATTAATT-3'<br>5'-pUUAAUUaaAAGACUUCAAGcGG-3' | 303g<br>GD4 | L-FL3 | 27<br>40 |
| 5'-GCTTGAAGTCTTTAATTAATT-3'<br>5'-pUUAAUUAAAGACUUCAAGCgg-3' | 303g | L-FL4 | 27<br>56 |
| 5'-GCTTGAAGTCTTTAATTAATT-3'<br>5'-pUUAAUUAAAGACUUCAAGCGG-3' | 303g<br>GD1 | L-FL5 | 27<br>42 |
| 5'-GCTTGAAGTCTTTAAUUAATT-3'<br>5'-pUUAAUUAAAGACUUCAAGcGG-3' | L-S-RF<br>GD2 | L-FL6 | 41<br>38 |
| 5'-GCTTGAAGTCTTTAAUUAATT-3'<br>5'-pUUAAUUAAAGACUUCAaGcGG-3' | L-S-RF<br>GD3 | L-FL7 | 41<br>39 |
| 5'-GCTTGAAGTCTTTAAUUAATT-3'<br>5'-pUUAAUUaaAAGACUUCAAGcGG-3' | L-S-RF<br>GD4 | L-FL8 | 41<br>40 |
| 5'-GCTTGAAGTCTTTAAUUAATT-3'<br>5'-pUUAAUUAAAGACUUCAAGCgg-3' | L-S-RF | L-FL9 | 41<br>56 |
| 5'-GCTTGAAGTCTTTAAUUAATT-3'<br>5'-pUUAAUUAAAGACUUCAAGCGG-3' | L-S-RF<br>GD1 | L-FL10 | 41<br>42 |
| 5'-GCUUGAAGUCUUUAAUUAAtt-3'<br>5'-pUUAAUUAAAGACUUCAAGCgg-3' | G1A | L-FL11 | 19<br>56 |
| 5'-GCUUGAAGUCUUUAAUUAAtt-3'<br>5'-pUUAAUUAAAGACUUCAAGCGG-3' | G1A<br>GD1 | L-FL12 | 19<br>42 |
| 5'-GCUUGAAGUCUUUAAUUAAtt-3'<br>5'-pUUAAUUaaAAGACUUCAAGcGG-3' | G1A<br>GD4 | L-FL13 | 19<br>40 |
| 5'-GCUUGAAGUCUUUAAUUAAtt-3'<br>5'-UUAAUUAAAGACUUCAAGCgg-3' | G1A<br>G1B | L-FL18 | 19<br>20 |
| 5'-GCUUGAUUUCUGAAAUUAAtt-3'<br>5'-UUAAUUUCAGAAAUCAAGCgg-3' | 178H<br>178I | Sc<br>Control | 54<br>55 |

Uppercase = RNA
Lowercase = dna
Lowercase underline = lna
Uppercase bold underline = 2'F-ANA (FANA)
Uppercase bold italic = 2'F-RNA
p = 5'-Phosphate The second series, referred to as "L-FL2", was designed based on 2'F-ANA/2'F-RNA architectures shown to have significant potency-improving synergy (see Examples 2 and 3 above). The sequences of the duplexes of the L-FL2 series are provided at Table V.

TABLE V

Sequences of the siRNAs of the L-FL2 series used in the studies described herein

| Strands | Strand Labels | siRNA labels | SEQ ID NO: |
|---|---|---|---|
| 5'-GCuUGAAGUCuUUAAuUAATT-3'<br>5'-UUAAUUAAAGACUUCAAGCgg-3' | GD-21<br>G1B | L-FL2-1 | 43<br>20 |
| 5'-GCuUGAAGUCuUUAATuAATT-3'<br>5'-UUAAUUAAAGACUUCAAGCgg-3' | GD-22<br>G1B | L-FL2-2 | 44<br>20 |
| 5'-GCuUGAAGUCuUUAAUUAATT-3'<br>5'-UUAAUUAAAGACUUCAAGCgg-3' | GD-23<br>G1B | L-FL2-3 | 45<br>20 |
| 5'-GCuUGAAGUCuUUAATUAATT-3'<br>5'-UUAAUUAAAGACUUCAAGCgg-3' | GD-24<br>G1B | L-FL2-4 | 46<br>20 |
| 5'-GCuUGAAGUCuUUAAUUAATT-3'<br>5'-UUAAUUAAAGACUUCAAGCgg-3' | GD-25<br>G1B | L-FL2-5 | 47<br>20 |
| 5'-GCuUGAAGUCuUUAAuUAATT-3'<br>5'-pUUAAUUAAAGACUUCAAGcGG-3' | GD-21<br>GD2 | L-FL2-6 | 43<br>38 |
| 5'-GCuUGAAGUCuUUAATuAATT-3'<br>5'-pUUAAUUAAAGACUUCAAGcGG-3' | GD-22<br>GD2 | L-FL2-7 | 44<br>38 |
| 5'-GCuUGAAGUCuUUAAUUAATT-3'<br>5'-pUUAAUUAAAGACUUCAAGcGG-3' | GD-23<br>GD2 | L-FL2-8 | 45<br>38 |
| 5'-GCuUGAAGUCuUUAATUAATT-3'<br>5'-pUUAAUUAAAGACUUCAAGcGG-3' | GD-24<br>GD2 | L-FL2-9 | 46<br>38 |
| 5'-GCuUGAAGUCuUUAAUUAATT-3'<br>5'-pUUAAUUAAAGACUUCAAGcGG-3' | GD-25<br>GD2 | L-FL2-10 | 47<br>38 |
| 5'-GCUUGAAGUCUUUAAUUAAtt-3'<br>5'-UUAAUUAAAGACUUCAAGCgg-3' | G1A<br>G1B | Control | 19<br>20 |
| 5'-GCUUGAUUUCUGAAAUUAAtt-3'<br>5'-UUAAUUUCAGAAAUCAAGCgg-3' | 178H<br>178I | Sc<br>Control | 54<br>55 |

Uppercase = RNA
Lowercase = dna
Lowercase underline = lna
Uppercase bold underline = 2'F-ANA (FANA)
Uppercase bold italic = 2'F-RNA
p = 5'-Phosphate The third series, referred to as "L-FL3", utilizes the same sense strands from L-FL2 annealed with all-2'F-RNA antisense strands. The sequences of the duplexes of the L-FL3 series are provided at Table VI.

TABLE VI

Sequences of the siRNAs of the L-FL3 series used in the studies described herein

| Sequence | Strand ID | siRNA ID | SEQ ID NO: |
|---|---|---|---|
| 5'-GCuUGAAGUCuUUAAuUAATT-3'<br>5'-p*TTAATTAAAGACTTCAAGCGG*-3' | GD-21<br>303f | L-FL3-1 | 43<br>26 |
| 5'-GCuUGAAGUCuUUAATuAATT-3'<br>5'-p*TTAATTAAAGACTTCAAGCGG*--3' | GD-22<br>303f | L-FL3-2 | 44<br>26 |
| 5'-GCuUGAAGUCuUUAAUUAATT-3'<br>5'-p*TTAATTAAAGACTTCAAGCGG*--3' | GD-23<br>303f | L-FL3-3 | 45<br>26 |
| 5'-GCuUGAAGUCuUUAATUAATT-3'<br>5'-p*TTAATTAAAGACTTCAAGCGG*-3' | GD-24<br>303f | L-FL3-4 | 46<br>26 |
| 5'-GCuUGAAGUCuUUAAUUAATT-3'<br>5'-p*TTAATTAAAGACTTCAAGCGG*-3' | GD-25<br>303f | L-FL3-5 | 47<br>26 |

Uppercase = RNA
Lowercase = dna
Lowercase underline = lna
Uppercase bold underline = 2'F-ANA (FANA)
Uppercase bold italic = 2'F-RNA
p = 5'-Phosphate Each oligonucleotide was characterized by ESI-TOF mass spectroscopy (Table VII) and for some of the oligonucleotides by analytical denaturing PAGE followed by stains-all treatment.

TABLE VII

Mass spectroscopy data for the oligonucleotides of the L-FL, L-FL2 and L-FL3 series

| Sequence | Expected Mass (M − H)+ | Experimental Mass |
|---|---|---|
| GD2 | 6814 | 6814.3 |
| GD3 | 6826 | 6826.7 |
| GD4 | 6814 | 6812.5 |
| L-S-RF | n.d. | n.d. |
| G1A | 6618 | 6616.5 |
| G1B | 6674 | 6672.2 |
| 178H | 6618 | 6616.4 |
| 178I | 6674 | 6671.9 |
| GD21 | 6707 | 6705.3 |
| GD22 | 6720 | 6718 |
| GD23 | 6696 | 6693 |
| GD24 | 6708 | 6705.8 |
| GD25 | 6690 | 6687.4 |
| 303g | 6804 | 6802 |
| 303f | 6911 | 6911 |

Figure 6:
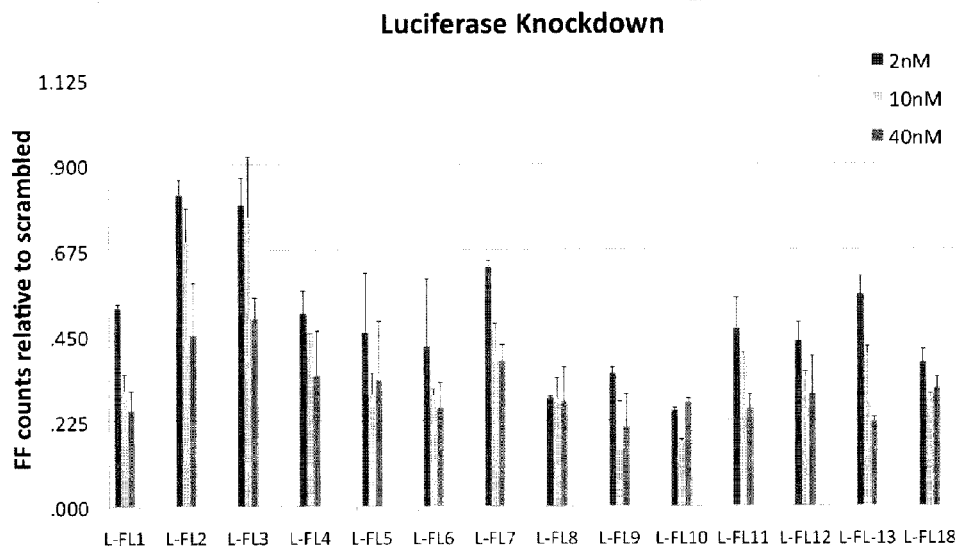
FIG. 6 shows luciferase knockdown experiments using oligonucleotide duplexes comprising a 2'F-ANA sense strands and antisense strands containing 2'F-ANA overhangs and LNA inserts.

Analysis of the data presented in FIG. 6 indicates that antisense strand GD2, containing two 3' FANA (2'F-ANA) overhangs followed by a single LNA residue is compatible with the RNAi machinery, and in some cases can improve siRNA potency relative to a regular RNA antisense strand (compare L-FL1 with L-FL4). Considering 3'-modified RNAs are generally more stable to nuclease degradation, this antisense architecture was chosen to move forward with in further studies, now focused on probing for intrastrand 2'F-ANA/LNA synergy in the sense strand.

As shown above (Examples 2 and 3), potent gene silencing may be achieved using 2'F-ANA/2'F-RNA chimera siRNAs. Chimeric 2'F-ANA/LNA siRNA architectures comprising the L-FL2 series of siRNAs were then designed and studied. Sense strands were designed with alternating regions of 2'F-ANA and LNA moving from 5' to 3'. LNA incorporation was kept to a minimum by surrounding strongly northern-puckered LNA inserts with RNA. Chemical modifications at the 3' ends of the sense strands were varied in attempts to capitalize on the observed thermodynamic bias of RISC for loading of the siRNA strand with the weakest binding affinity at the 5' end.7 Sense strands GD21-GD25 are identical until nucleotide 14, after which several patterns of chemical modification were employed. Strands GD21 and 22 feature alternating LNA-2'F-ANA regions designed to explore the effects of placing contrasting sugar puckers (northern vs. southeastern) side by side in a sense strand. GD23-25 feature various patterns of 2'F-ANA modification combined with unmodified RNA, including 1-1 altimer designs, 2-2 altimer designs, and fully RNA 3' regions followed by 2'F-ANA overhangs. The $T_m$ of the oligonucleotide duplexes of the L-FL2 series is provided in Table VIII below.

TABLE VIII $T_m$ of the oligonucleotide duplexes of the L-FL2 series

| siRNA | $T_m$ (° C.) |
|---|---|
| L-FL2-1 | 62.9 |
| L-FL2-2 | 59.2 |
| L-FL2-3 | 58.4 |
| L-FL2-4 | 55.0 |
| L-FL2-5 | 58.6 |
| L-FL2-6 | 65.7 |
| L-FL2-7 | 62.2 |
| L-FL2-8 | n.d. |
| L-FL2-9 | 60.5 |
| L-FL2-10 | 61.9 |
| Control | 60.5 |

According to the $T_m$ data obtained, the 3' chemical modifications did not create significant changes in duplex binding affinity, suggesting that strand bias for loading of the proper antisense strand was not introduced. However, the siRNA sequence has high A:U content at the 5' end of the antisense strand, favoring proper RISC loading, and perhaps further strand bias is unnecessary. To examine the gene silencing activity of these LNA/2'F-ANA sense strands, siRNAs were prepared by annealing GD21-GD25 with either a regular RNA antisense strand, or with GD2, the potent LNA/2'F-ANA antisense strand from the L-FL series. Indeed, despite the failure to introduce significant strand bias, several of these modified architectures were able to elicit potent gene silencing, comparable to or better than the native RISC substrate, dsRNA.

Figure 7:
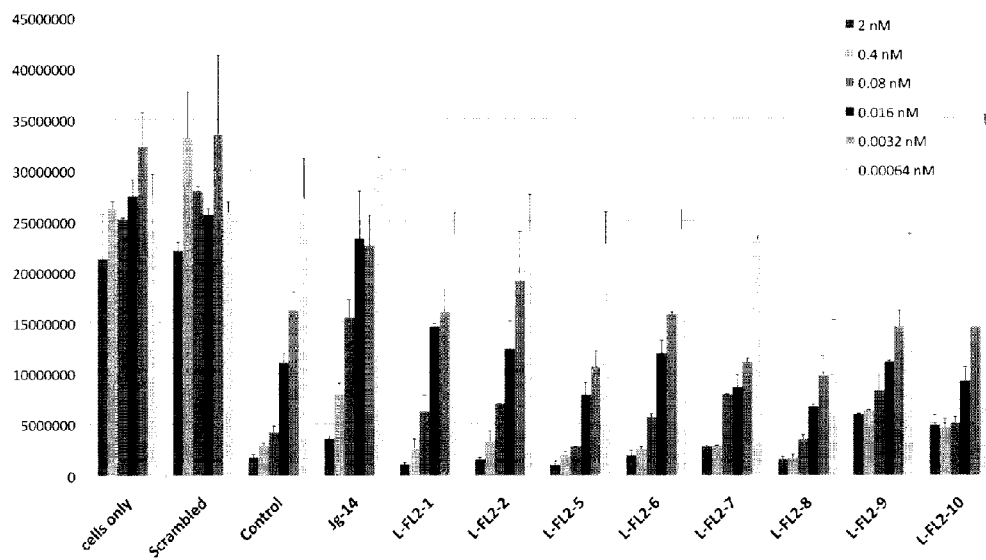
FIG. 7 shows luciferase knockdown experiments using oligonucleotide duplexes comprising a sense strand containing both 2'F-ANA and LNA.

Initial siRNA assays with the L-FL2 series indicated potency increases several fold better than unmodified controls. In fact, 70-90% knockdown was observed at subnanomolar ranges for L-FL2-9 and L-FL2-10, stronger knockdown than even 2 nM treatments with unmodified siRNA. Subsequent firefly luciferase knockdown assays indicate potent knockdown from the L-FL2 series. Shown in FIG. 7 are the knockdown results for the best siRNAs in the L-FL2 series. Several of the architectures are well tolerated by the RISC machinery. Some of the architectures tested here are much more potent gene silencers than unmodified siRNA, especially at lower doses. Additionally, the LNA-containing designs appear to be more potent than one of the potent 2'F-ANA/2'F-RNA siRNA designs described above (jg-14). These data thus show that heavily modified siRNA designs have seemingly no detrimental effects on gene silencing.

The L-FL2 series demonstrates sense stand modification plans that are highly compatible with gene knockdown. However, in these cases the antisense strand remains unmodified, or only 3'-modified. It was next tested whether it was possible to combine these potent sense strand architectures with antisense strand modifications compatible with RISC, such as 2'F-RNA antisense strands.

Figure 8:
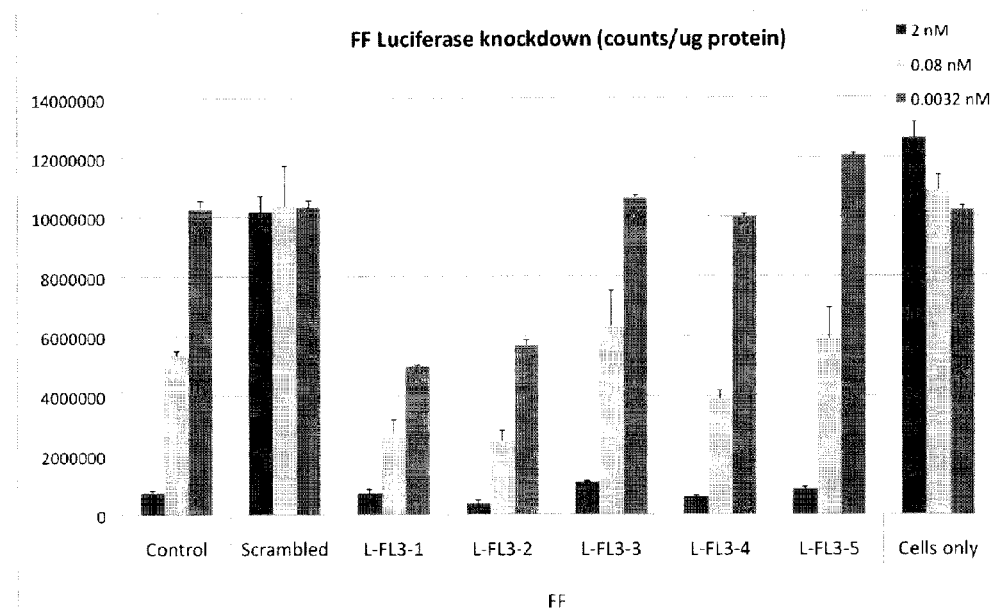
FIG. 8 shows luciferase knockdown experiments using oligonucleotide duplexes comprising a sense strand containing both 2'F-ANA and LNA annealed with a fully 2'F-RNA antisense strand.

Based on the efficacy of the LNA/2'F-ANA sense strands from the L-FL2 series, and on the observed efficacy of fully 2'F-RNA antisense strands, highly modified siRNAs containing only 7-11 RNA inserts were designed (L-FL3 series). These chemical modification architectures represent the combination of the designs shown herein to be compatible with siRNA-based silencing (Examples 2 and 3, L-FL1 and L-FL2 series). As shown in FIG. 8, these heavily modified siRNA-mimics show potent gene-silencing abilities. Some of these modified siRNAs are significantly more potent than control siRNA, even at the midrange 0.08 nM dose where the potency of the modified siRNAs of the L-FL2 series was about equal to that of the unmodified siRNA.

Example 5: C-Myb Knockdown Using siRNA Duplexes Based on the 2'F-ANA/2'F-RNA and 2'F-ANA/2'F-RNA/LNA Architectures C-myb is a protooncogene implicated in leukemia. It encodes proteins essential for hematopoetic cell proliferation. 2'F-ANA/2'F-RNA and 2'F-ANA/2'F-RNA/LNA architectures shown to have luciferase and/or 4E-BP gene silencing activities were tested against another target, namely c-myb. The sequences of the duplexes of the C-myb series are provided in Table IX.

TABLE IX

Sequences of the siRNAs of the C-myb series used in the studies described herein

| Strands | sIRNA labels | SEQ ID NO: |
|---|---|---|
| 5'-UGUUAUUGCCAAGCACUUAAA-3' | Cmyb-1 | 48 |
| 5'-UAAGUGCUUGGCAAUAACAGA-3' | | 49 |
| 5'-TGTUAUTGCCAAGCACTUAAA-3' | Cmyb-2 | 50 |
| 5'-p*UAAGUGCUUGGCAAUAACAGA*-3' | | 51 |
| 5'-TGuATTGCCaAGCAcUTAAA-3' | Cmyb-3 | 52 |
| 5'-p*UAAGUGCUUGGCAAUAACAGA*-3' | | 51 |
| 5'-TGTUAUTGCCAAGCACTUAAA-3' | Cmyb-4 | 50 |
| 5'-UAAGUGCUUGGCAAUAACAGAAGA-3' | | 49 |
| 5'-TGuATTGCCaAGCAcUTAAA-3' | Cmyb-5 | 52 |
| 5'-UAAGUGCUUGGCAAUAACAGA-3' | | 49 |
| 5'-UGUUAUUGCCAAGCACUUAAA-3' | Cmyb-6 | 48 |
| 5'-p*UAAGUGCUUGGCAAUAACAGA*-3' | | 51 |
| 5'-GCUUGAAGUCUUUAAUUAAtt-3' | Scrambled | 19 |
| 5'-UUAAUUAAAGACUUCAAGCgg-3' | | 20 |
| 5'-CGTACGCGGAAUACTU CGATT-3' | Scrambled Mod. 1 | 35 |
| 5'-p*UCGAAGUAUUCCGCGUACGUU*-3' | | 37 |

TABLE IX-continued

Sequences of the siRNAs of the C-myb series used in the studies described herein

| Strands | sIRNA labels | SEQ ID NO: |
|---|---|---|
| 5'-GCuUGAAGUCuUUAAuUAATT-3' | Scrambled Mod. 2 | 43 |
| 5'-p*TTAATTAAAGACTTCAAGCGG*-3' | | 26 |

Figure 9A:
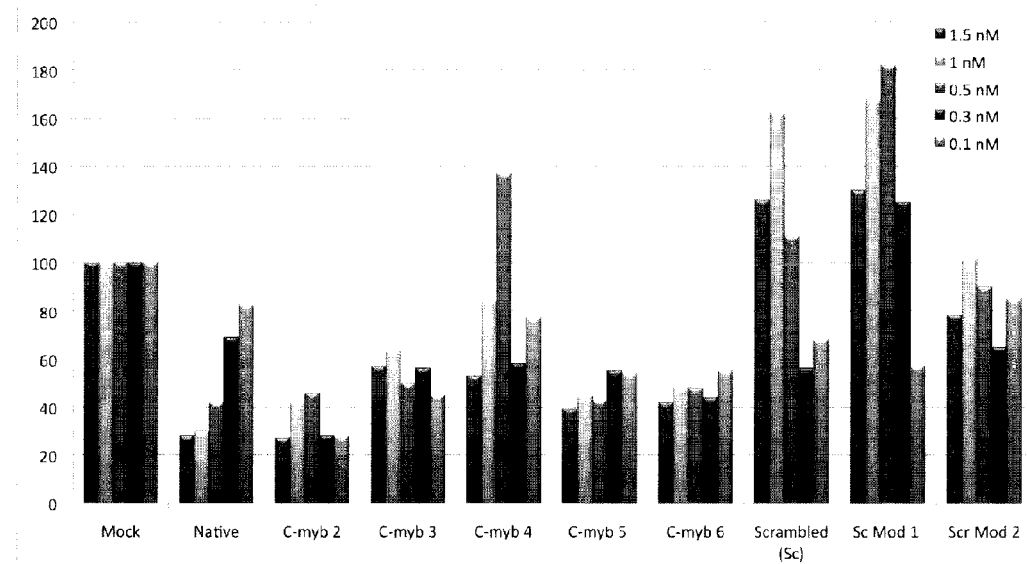
FIGS. 9A-9B show c-myb knockdown experiments using 2'F-ANA/2'F-RNA/LNA siRNAs.

Uppercase = RNA
Lowercase = dna
Lowercase underline = lna
Uppercase bold underline = 2'F-ANA (FANA)
Uppercase bold italic = 2'F-RNA
p = 5'-Phosphate As shown in FIG. 9A, 2'F-ANA/2'F-RNA and 2'F-ANA/2'F-RNA/LNA modified siRNA are capable of silencing gene expression in another target, and are better at silencing c-myb than unmodified siRNA at the lower dosages. The 2'F-ANA/2'F-RNA architecture appears to be more potent under the experimental conditions tested.

Figure 9B:
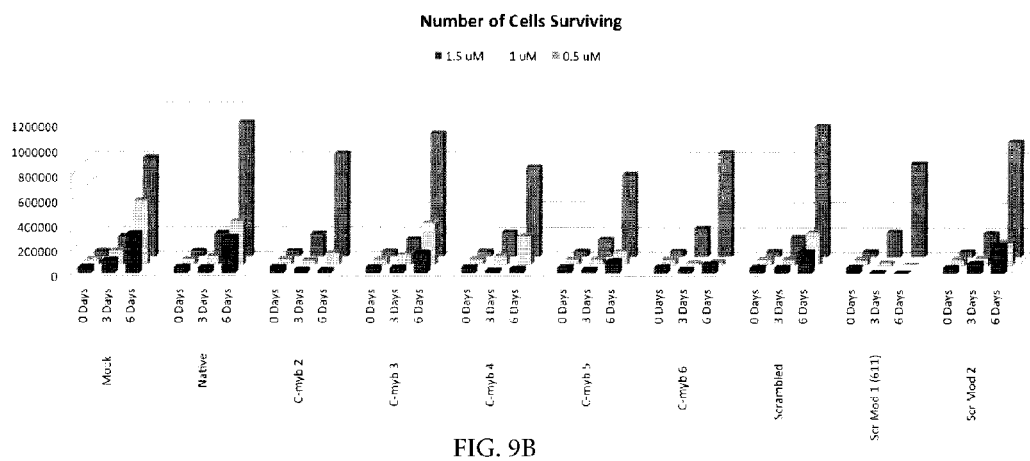

FIG. 9B shows the survival rate (y-axis represents number of leukemia cells still living after the indicated time periods after treatment with siRNA designed to target c-myb and prevent leukemia cell proliferation) following siRNA treatment. Interestingly, unmodified siRNA-treated leukemia cells rebound 6 days after treatment and start proliferating again, whereas several of the modified siRNAs still prevent proliferation after 6 days. This suggests that modified siRNAs are not degraded as much as unmodified siRNAs after these time periods.

The novel chimeric siRNA architectures reported herein represent previously unexplored siRNA-mimics capable of equivalent or improved potencies compared to unmodified siRNA.

TABLE X

Summary of siRNAs used in the studies described herein

| Sequence | siRNA duplex ID | SEQ ID NO: |
|---|---|---|
| siRNAs of Table III | | |
| 5' AACUCACCUGUGACCAAAAca | Unmodified Control | 1 |
| 5' UUUUGGUCACAGGUGAGUUcc | 4EBP-1 Human | 2 |
| 5' AAGACUCCAAAGUAGAAGUaa | Unmodified Control 4EBP- | 3 |
| 5' ACUUCUACUUUGGAGUCUUca | 2 Human and Murine | 4 |
| 5' AACUCACCUGUGGCCAAAAca | Unmodified Control | 5 |
| 5' UUUUGGCCACAGGUGAGUUcc | 4EBP-1 Murine | 6 |
| 5' AACTCACCTGTGGCCAAAACA | 4EBP-1 Murine_14 | 7 |
| 5'p*UUUUGGCCACAGGUGAGUUCC* | | 8 |
| 5' AACTCACCTGTGACCAAAACA | 4EBP-1 Human_14 | 9 |
| 5'p*UUUUGGUCACAGUGAGUUCC* | | 10 |
| 5' AAGACTCCAAAGTAGAAGTAA | 4EBP-2 Mouse_4 or | 11 |
| 5'p*ACUUCUACUUUGGAGUCUUCA* | 4EBP-2 Human_14 | 12 |
| 5' AACUCACCTG*UGGCC*AAAACA | 4EBP1 Mouse_611 | 13 |
| 5'p*UUUUGGCCACAGGUGAGUUCC* | | 14 |
| 5' AACUCACCTGUGACCAAAACA | 4EBP1 Human_ 611 | 15 |
| 5'p*UUUUGGUCACAGGUGAGUUCC* | | 16 |
| 5' AAGACUCCAAAGTAGAAGTAA | 4EBP2 Mouse_611 or 4EBP2 Human_611 | 17 |
| 5'p*ACUUCUACUUUGGAGUCUUCA* | | 18 |

TABLE X-continued

Summary of siRNAs used in
the studies described herein

| Sequence | siRNA duplex ID | SEQ ID NO: |
|---|---|---|
| siRNAs of Table I | | |
| 5'-GCUUGAAGUCUUUAAUUAAtt-3'<br>5'-UUAAUUAAAGACUUCAAGCgg-3' | jg-1 | 19<br>20 |
| 5'-*GCTTGAAGTCTTTAATTAATT*-3'<br>5'-*TTAATTAAAGACTTCAAGCGG*-3' | jg-2 | 21<br>22 |
| 5'-*GCTTGAAGTCTTTAATTAATT*-3'<br>5'-*TTAATTAAAGACTTTAAGCGG*-3 | jg-3 | 23<br>24 |
| 5'-*GCTTGAAGTCTTTAATTAATT*-3'<br>5'-p*TTAATTAAAGACTTCAAGCGG*-3' | jg-4 | 25<br>26 |
| 5'-*GCTTGAAGTCTTTAATTAATT*-3'<br>5'-p*TTAATTAAAGACTTCAAGCGG*-3' | jg-5 | 27<br>28 |
| 5'-*GCTTGAAGTCTTTAATTAATT*-3'<br>5'-UUAAUUAAAGACUUCAAGCgg-3' | jg-6 | 21<br>20 |
| 5'-GCUUGAAGUCUUUAAUUAAtt-3'<br>5'-*TTAATTAAAGACTTCAAGCGG*-3' | jg-7 | 19<br>22 |
| 5'-*GCTTGAAGTCTTTAATTAATT*-3'<br>5'-UUAAUUAAAGACUUCAAGCgg-3' | jg-8 | 23<br>20 |
| 5'-GCUUGAAGUCUUUAAUUAAtt-3'<br>5'-*TTAATTAAAGACTTCAAGCGG*-3 | jg-9 | 19<br>24 |
| 5'-*GCTTGAAGTCTTTAATTAATT*-3'<br>5'-UUAAUUAAAGACUUCAAGCgg-3' | jg-10 | 25<br>20 |
| 5'-GCUUGAAGUCUUUAAUUAAtt-3'<br>5'-p*TTAATTAAAGACTTCAAGCGG*-3' | jg-11 | 19<br>26 |
| 5'-*GCTTGAAGTCTTTAATTAATT*-3'<br>5'-UUAAUUAAAGACUUCAAGCgg-3' | jg-12 | 27<br>20 |
| 5'-GCUUGAAGUCUUUAAUUAAtt-3'<br>5'-p*TTAATTAAAGACTTCAAGCGG*-3' | jg-13 | 19<br>28 |
| 5'-*GCTTGAAGTCTTTAATTAATT*-3'<br>5'-p*TTAATTAAAGACTTCAAGCGG*-3' | jg-14 | 27<br>26 |
| 5'-*GCTTGAAGTCTTTAATTAATT*-3'<br>5'-p*TTAATTAAAGACTTCAAGCGG*-3' | jg-15 | 25<br>28 |
| siRNAs of Table II | | |
| 5'-CGUACGCGGAAUACUUCGAtt-3'<br>5'-UCGAAGUAUUCCGCGUACGtt-3' | kl-ctl | 29<br>30 |
| 5'-*CGUACGCGGAAUACUUCGAUU*-3'<br>5'-UCGAAGUAUUCCGCGUACGtt-3' | kl-1 | 31<br>30 |
| 5'-*CGTACGCGGAATACTTCGATT*-3'<br>5'-UCGAAGUAUUCCGCGUACGtt-3' | kl-2 | 32<br>30 |
| 5'-*CGTACGCGGAATAC*UUCGA*TT*-3'<br>5'-UCGAAGUAUUCCGCGUACGtt-3' | kl-3 | 33<br>30 |
| 5'-*CGTACGCGGAAU*A*CT*CG*ATT*-3'<br>5'-UCGAAGUAUUCCGCGUACGtt-3' | kl-4 | 34<br>30 |
| 5'-*CGTA*CG*CGGAAU*A*CTU*C*GATT*-3'<br>5'-UCGAAGUAUUCCGCGUACGtt-3' | kl-5 | 35<br>30 |
| 5'-*CGTACGCGGAAU*A*CTU*C*GATT*-3'<br>5'-UCGAAGUAUUCCGCGUACGtt-3' | kl-6 | 36<br>30 |
| 5'-*CGUACGCGGAAUACUUCGAUU*-3'<br>5'-p*UCGAAGUAUUCCGCGUACGUU*-3' | kl-7 | 31<br>37 |

TABLE X-continued

Summary of siRNAs used in the studies described herein

| Sequence | siRNA duplex ID | SEQ ID NO: |
|---|---|---|
| 5'-CGTACGCGGAATACTTCGATT-3'<br>5'-p*UCGAAGUAUUC*CGCGUACGUU-3' | k1-8 | 32<br>37 |
| 5'-CGTACGCGGAATAC*UU*CGATT-3'<br>5'-p*UCGAAGUAUUC*CGCGUACGUU-3' | k1-9 | 33<br>37 |
| 5'-CGTACGCGGAAU*A*C*U*UCGATT-3'<br>5'-p*UCGAAGUAUUC*GCGUACGUU-3' | k1-10 | 34<br>37 |
| 5'-CGTACGCGGAAU*A*C*UU*CGATT-3'<br>5'-p*UCGAAGUAUUC*GCGUACGUU-3' | k1-11 | 35<br>37 |
| 5'-CGTACGCGGA*AU*A*C*U*U*CGATT-3'<br>5'-p*UCGAAGUAUUC*GCGUACGUU-3' | k1-12 | 36<br>37 |
| siRNAs of Table IV | | |
| 5'-GCTTGAAGTCTTTAATTAATT-3'<br>5'-pUUAAUUAAAGACUUCAAGcGG-3' | L-FL1 | 27<br>38 |
| 5'-GCTTGAAGTCTTTAATTAATT-3'<br>5'-pUUAAUUAAAGACUUCAaGcGG-3' | L-FL2 | 27<br>39 |
| 5'-GCTTGAAGTCTTTAATTAATT-3'<br>5'-pUUAAUUaaAAGACUUCAAGcGG-3' | L-FL3 | 27<br>40 |
| 5'-GCTTGAAGTCTTTAAUUAATT-3'<br>5'-pUUAAUUAAAGACUUCAAGcGG-3' | L-FL6 | 41<br>38 |
| 5'-GCTTGAAGTCTTTAAUUAATT-3'<br>5'-pUUAAUUAAAGACUUCAaGcGG-3' | L-FL7 | 41<br>39 |
| 5'-GCTTGAAGTCTTTAAUUAATT-3'<br>5'-pUUAAUUaaAAGACUUCAAGcGG-3' | L-FL8 | 41<br>40 |
| 5'-GCUUGAAGUCUUUAAUUAAtt-3'<br>5'-pUUAAUUAAAGACUUCAAGcGG-3' | L-FL13 | 19<br>38 |
| 5'-GCUUGAAGUCUUUAAUUAAtt-3'<br>5'-pUUAAUUAAAGACUUCAaGcGG-3' | L-FL14 | 19<br>39 |
| 5'-GCUUGAAGUCUUUAAUUAAtt-3'<br>5'-pUUAAUUaaAAGACUUCAAGcGG-3' | L-FL15 | 19<br>40 |
| 5'-GCUUGAAGUCUUUAAUUAAtt-3'<br>5'-pUUAAUUAAAGACUUCAAGcGG-3' | L-FL12 | 19<br>42 |
| 5'-GCUUGAAGUCUUUAAUUAAtt-3'<br>5'-UUAAUUAAAGACUUCAAGCgg-3' | Control | 19<br>20 |
| 5'-GCUUGAUUUCUGAAAUUAAtt-3'<br>5'-UUAAUUUCAGAAAUCAAGCgg-3' | Sc control | 54<br>55 |
| siRNAs of Table V | | |
| 5'-GCTTGAAGTCTTTAATTAATT-3'<br>5'-pUUAAUUAAAGACUUCAAGcGG-3' | L-FL1 | 27<br>38 |
| 5'-GCTTGAAGTCTTTAATTAATT-3'<br>5'-pUUAAUUAAAGACUUCAaGcGG-3' | L-FL2 | 27<br>39 |
| 5'-GCTTGAAGTCTTTAATTAATT-3'<br>5'-pUUAAUUaaAAGACUUCAAGcGG-3' | L-FL3 | 27<br>40 |
| 5'-GCTTGAAGTCTTTAATTAATT-3'<br>5'-pUUAAUUAAAGACUUCAAGcgg-3' | L-FL4 | 27<br>56 |
| 5'-GCTTGAAGTCTTTAATTAATT-3'<br>5'-pUUAAUUAAAGACUUCAAGcGG-3' | L-FL5 | 27<br>42 |
| 5'-GCTTGAAGTCTTTAAUUAATT-3'<br>5'-pUUAAUUAAAGACUUCAAGcGG-3' | L-FL6 | 41<br>38 |

TABLE X-continued

Summary of siRNAs used in
the studies described herein

| Sequence | siRNA duplex ID | SEQ ID NO: |
|---|---|---|
| 5'-GCTTGAAGTCTTTAAUUAATT-3'<br>5'-pUUAAUUAAAGACUUCAaGcGG-3' | L-FL7 | 41<br>39 |
| 5'-GCTTGAAGTCTTTAAUUAATT-3'<br>5'-pUUAAUUaaAAGACUUCAAGcGG-3' | L-FL8 | 41<br>40 |
| 5'-GCTTGAAGTCTTTAAUUAATT-3'<br>5'-pUUAAUUAAAGACUUCAAGCgg-3' | L-FL9 | 41<br>56 |
| 5'-GCTTGAAGTCTTTAAUUAATT-3'<br>5'-pUUAAUUAAAGACUUCAAGCGG-3' | L-FL10 | 41<br>42 |
| 5'-GCUUGAAGUCUUUAAUUAAtt-3'<br>5'-pUUAAUUAAAGACUUCAAGCgg-3' | L-FL11 | 19<br>56 |
| 5'-GCUUGAAGUCUUUAAUUAAtt-3'<br>5'-pUUAAUUAAAGACUUCAAGCGG-3' | L-FL12 | 19<br>42 |
| 5'-GCUUGAAGUCUUUAAUUAAtt-3'<br>5'-pUUAAUUaaAAGACUUCAAGcGG-3' | L-FL13 | 19<br>40 |
| 5'-GCUUGAAGUCUUUAAUUAAtt-3'<br>5'-UUAAUUAAAGACUUCAAGCgg-3' | L-FL18 | 19<br>20 |
| 5'-GCUUGAUUUCUGAAAUUAAtt-3'<br>5'-UUAAUUUCAGAAAUCAAGCgg-3' | Sc Control | 54<br>55 |

Table V

| 5'-GCuUGAAGUCuUUAAuAATT-3'<br>5'-p*TTAATTAAAGACTTCAAGCGG***-3' | L-FL3-1 | 43<br>26 |
|---|---|---|
| 5'-GCuUGAAGUCuUUAATuAATT-3'<br>5'-p*TTAATTAAAGACTTCAAGCGG*-3' | L-FL3-2 | 44<br>26 |
| 5'-GCuUGAAGUCuUUAAUuAATT-3'<br>5'-p*TTAATTAAAGACTTCAAGCGG*-3' | L-FL3-3 | 45<br>26 |
| 5'-GCuUGAAGUCuUUAATuAATT-3'<br>5'-p*TTAATTAAAGACTTCAAGCGG*-3' | L-FL3-4 | 46<br>26 |
| 5'-GCuUGAAGUCuUUAAUUAATT-3'<br>5'-p*TTAATTAAAGACTTCAAGCGG*-3' | L-FL3-5 | 47<br>26 | siRNAs of Table IX

| 5'-UGUUAUUGCCAAGCACUUAAA-3'<br>5'-UAAGUGCUUGGCAAUAACAGA-3' | Cmyb-1 | 48<br>49 |
|---|---|---|
| 5'-TGTUAUTGCCAAGCACTUAAA-3'<br>5'-p*UAAGUGCUUGGCAAUAACAGA*-3' | Cmyb-2 | 50<br>51 |
| 5'-TGuUATTGCCaAGCAcUTAAA-3'<br>5'-p*UAAGUGCUUGGCAAUAACAGA*-3' | Cmyb-3 | 52<br>51 |
| 5'-TGTUAUTGCCAAGCACTUAAA-3'<br>5'-UAAGUGCUUGGCAAUAACAGA-3' | Cmyb-4 | 50<br>49 |
| 5'-TGuUATTGCCaAGCAcUTAAA-3'<br>5'-UAAGUGCUUGGCAAUAACAGA-3' | Cmyb-5 | 52<br>49 |
| 5'-UGUUAUUGCCAAGCACUUAAA-3'<br>5'-p*UAAGUGCUUGGCAAUAACAGA*-3' | Cmyb-6 | 48<br>51 |
| 5'-GCUUGAAGUCUUUAAUUAAtt-3'<br>5'-UUAAUUAAAGACUUCAAGCgg-3' | Sc | 19<br>20 |
| 5'-CGTACGCGGAAUACUCGATT-3'<br>5'-p*UCGAAGUAUUCCGCGUACGUU*-3' | Sc Mod 1 | 35<br>37 |
| 5'-GCuUGAAGUCuUUAAuAATT-3'<br>5'-p*TTAATTAAAGACTTCAAGCGG***-3' | Sc Mod 2 | 43<br>26 |

TABLE X-continued

Summary of siRNAs used in
the studies described herein

Figure 4B:
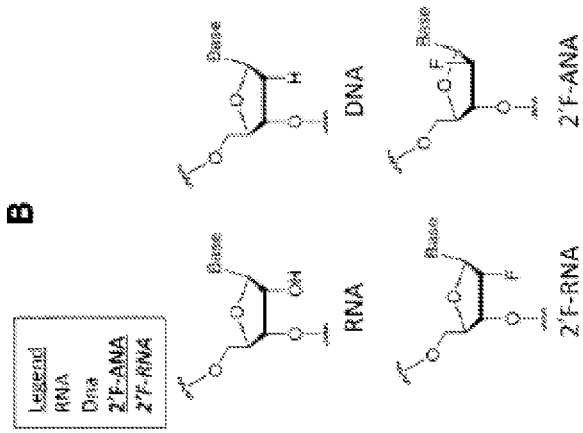
FIG. 4B shows the sequences of the siRNAs used in FIG. 4A which are also shown in Table X below.

| Sequence | siRNA duplex ID | SEQ ID NO: |
| --- | --- | --- |
| siRNAs of FIG. 4 | | |
| 5' AACUCACCUGUGACCAAAAca | Unmodified Control 4EBP-1 | 1 |
| 5' UUUUGGUCACAGGUGAGUUcc | Human (siRNA Control 1) | 2 |
| 5' AACTCACCTGTGACCAAAACA | 4EBP-1 | 9 |
| 5'p*UUUUGGUCACAGGUGAGUUCC* | Human_14 | 10 |
| 5' AA_C_U_CA_CC_T_GUGA_C_C_A_AAACA | 4EBP1 | 15 |
| 5'p*UUUUGGUCACAGGUGAGUUCC* | Human_611 | 16 |
| 5' AAGACUCCAAAGUAGAAGUaa | Unmodified Control 4EBP-2 | 3 |
| 5' ACUUCUAGUUUGGAGUCUUca | Human (siRNA Control 2) | 4 |
| 5' AAGACTCCAAAGTAGAAGTAA | 4EBP-2 | 11 |
| 5'p*ACUUCUACUUUGGAGUCUUCA* | Human_14 | 12 |
| 5' AA_GA_CU_CC_AAA_G_T_AG_AA_G_TAA | 4EBP2 | 17 |
| 5'p*ACUUCUACUUUGG*_A_*GUCUUCA* | Human_611 | 18 |
| 5'-GCUUGAAGUCUUUAAUUAAtt-3' | Scrambled (Sc) | 19 |
| 5'-UUAAUUAAAGACUUCAAGCgg-3' | Control | 20 |
| 5'-GCTTGAAGTCTTTAATTAATT-3' | Scrambled (Sc) | 27 |
| 5'-p*UUAAUUAAAGACUUCAAGCGG*-3' | Modified Control 1 | 53 |
| 5'-CGTACGCGG_AA_U_A_C_T_U C_G_ATT-3' | Scrambled (Sc) | 35 |
| 5'-p*UCGAAGUAUUCCGCGUACGUU*-3' | Modified Control 2 | 37 |

Uppercase = RNA
Lowercase = dna
Lowercase underline = <u>lna</u>
Uppercase bold underline = 2'F-ANA (FANA)
Uppercase bold italic = 2'F-RNA
p = 5'-Phosphate Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A chemically-modified siRNA comprising an oligonucleotide duplex comprising a sense strand and an antisense strand, each respectively comprising:
   (i) Sense: [(2'F-ANA)$_3$(2'F-RNA)$_3$]$_2$ [(2'F-ANA)(2'F-RNA)]$_3$ (2'F-ANA)
   Antisense: (RNA)$_{19}$,
   (ii) Sense: [(2'F-ANA)$_3$(2'F-RNA)$_3$]$_2$ [(2'F-ANA)(2'F-RNA)]$_3$ (2'F-ANA)
   Antisense: (2'F-RNA)$_{19}$,
   (iii) Sense: [(2'F-ANA)(2'F-RNA)]$_9$ (2'F-ANA)
   Antisense: (RNA)$_{19}$,
   (iv) Sense: [(2'F-ANA)(2'F-RNA)]$_9$ (2'F-ANA)
   Antisense: (2'F-RNA)$_{19}$,
   (v) Sense: [(2'F-ANA)$_3$(2'F-RNA)$_3$]$_3$ (2'F-ANA)
   Antisense: (RNA)$_{19}$,
   (vi) Sense: [(2'F-ANA)$_3$(2'F-RNA)$_3$]$_3$ (2'F-ANA)
   Antisense: (2'F-RNA)$_{19}$
   (vii) Sense: (2'F-ANA)$_{19}$,
   Antisense: (2'F-RNA)$_{19}$, or
   (viii) Sense: (2'F-ANA)$_{14}$ (RNA)$_5$
   Antisense: (2'F-RNA)$_{19}$.

2. The chemically modified siRNA of claim 1, which comprises:
   Sense: [(2'F-ANA)$_3$(2'F-RNA)$_3$]$_2$ [(2'F-ANA)(2'F-RNA)]$_3$ (2'F-ANA)
   Antisense: (RNA)$_{19}$.

3. The chemically modified siRNA of claim 1, which comprises:
   Sense: [(2'F-ANA)$_3$(2'F-RNA)$_3$]$_2$ [(2'F-ANA)(2'F-RNA)]$_3$ (2'F-ANA)
   Antisense: (2'F-RNA)$_{19}$.

4. The chemically modified siRNA of claim 1, which comprises:
   Sense: [(2'F-ANA)(2'F-RNA)]$_9$ (2'F-ANA)
   Antisense: (RNA)$_{19}$.

5. The chemically modified siRNA of claim 1, which comprises:
   Sense: [(2'F-ANA)(2'F-RNA)]$_9$ (2'F-ANA)
   Antisense: (2'F-RNA)$_{19}$.

6. The chemically modified siRNA of claim 1, which comprises:
   Sense: [(2'F-ANA)$_3$(2'F-RNA)$_3$]$_3$ (2'F-ANA)
   Antisense: (RNA)$_{19}$.

7. The chemically modified siRNA of claim 1, which comprises:
   Sense: [(2'F-ANA)$_3$(2'F-RNA)$_3$]$_3$ (2'F-ANA)
   Antisense: (2'F-RNA)$_{19}$.

8. The chemically modified siRNA of claim 1, which comprises:
   Sense: (2'F-ANA)$_{19}$,
   Antisense: (2'F-RNA)$_{19}$.

9. The chemically modified siRNA of claim 1, which comprises:
   Sense: (2'F-ANA)$_{14}$ (RNA)$_5$
   Antisense: (2'F-RNA)$_{19}$.

10. The chemically-modified siRNA of claim 1, wherein the oligonucleotide duplex is fully modified with one or more 2'F-RNA and 2'F-ANA residues.

11. The chemically-modified siRNA of claim 1, wherein the oligonucleotide duplex comprises an overhang.

12. The chemically-modified siRNA of claim 11, wherein the overhang is a 1 to 5 residue overhang.

13. The chemically-modified siRNA of claim 12, wherein the overhang is a 2 residue overhang.

14. The chemically-modified siRNA of claim 11, wherein the overhang comprises DNA, 2'F-ANA, and/or 2'F-RNA residues.

15. The chemically-modified siRNA of claim 14, wherein the overhang comprises two 2'F-ANA residues.

16. The chemically-modified siRNA of claim 15, wherein the two 2'F-ANA residues are on the sense strand.

17. The chemically-modified siRNA of claim 15, wherein the two 2'F-ANA residues are on the antisense strand.

18. The chemically-modified siRNA of claim 1, wherein the sense strand and the antisense strand have a length of 19 to 23 nucleotide residues.

19. A pharmaceutical composition comprising the chemically-modified siRNA according to claim 1, together with a pharmaceutically acceptable excipient or carrier.

20. A method of degrading or decreasing the level of a target nucleic acid, or for decreasing production of a polypeptide encoded by said target nucleic acid, in a cell, the method comprising contacting the cell with an oligonucleotide duplex of claim 1, wherein the sense strand of the oligonucleotide duplex comprises a nucleobase sequence substantially identical to a nucleobase sequence of the target nucleic acid.

* * * * *

SEQUENCE LISTING

<160> NUMBER OF SEQ ID NOS: 56

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 1
aacucaccug ugaccaaaac a        21

```
<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 2
uuuuggucac aggugaguuc c                                               21

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 3
aagacuccaa aguagaagua a                                               21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 4
acuucuacuu uggagucuuc a                                               21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 5
aacucaccug uggccaaaac a                                               21
```

```
<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 6
uuuuggccac aggugaguuc c                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-deoxy-2'-
      fluoroarabinose sugar moiety

<400> SEQUENCE: 7
aactcacctg tggccaaaac a                                              21

<210> SEQ ID NO 8
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-fluororibose sugar
      moiety
<220> FEATURE:
<221> NAME/KEY: misc_feature
<222> LOCATION: (1)..(1)
<223> OTHER INFORMATION: 5'-phosphate modification

<400> SEQUENCE: 8
uuuuggccac aggugaguuc c                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-deoxy-2'-
      fluoroarabinose sugar moiety

<400> SEQUENCE: 9
aactcacctg tgaccaaaac a                                              21

<210> SEQ ID NO 10
<211> LENGTH: 21
```

```
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-fluororibose sugar
      moiety
<220> FEATURE:
<221> NAME/KEY: misc_feature
<222> LOCATION: (1)..(1)
<223> OTHER INFORMATION: 5'-phosphate modification

<400> SEQUENCE: 10
uuuuggucac aggugaguuc c                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-deoxy-2'-
      fluoroarabinose sugar moiety

<400> SEQUENCE: 11
aagactccaa agtagaagta a                                              21

<210> SEQ ID NO 12
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-fluororibose sugar
      moiety
<220> FEATURE:
<221> NAME/KEY: misc_feature
<222> LOCATION: (1)..(1)
<223> OTHER INFORMATION: 5'-phosphate modification

<400> SEQUENCE: 12
acuucuacuu uggagucuuc a                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (4)..(6)
<223> OTHER INFORMATION: nucleoside contains a 2'-fluororibose sugar
      moiety
<220> FEATURE:
<221> NAME/KEY: misc_feature
<222> LOCATION: (7)..(9)
<223> OTHER INFORMATION: nucleoside contains a 2'-deoxy-2'-
      fluoroarabinose sugar moiety
<220> FEATURE:
```

-continued

```
<221> NAME/KEY: misc_feature
<222> LOCATION: (10)..(12)
<223> OTHER INFORMATION: nucleoside contains a 2'-fluororibose sugar
      moiety
<220> FEATURE:
<221> NAME/KEY: misc_feature
<222> LOCATION: (13)..(13)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (14)..(14)
<223> OTHER INFORMATION: nucleoside contains a 2'-fluororibose sugar
      moiety
<220> FEATURE:
<221> NAME/KEY: misc_feature
<222> LOCATION: (15)..(15)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (16)..(16)
<223> OTHER INFORMATION: nucleoside contains a 2'-fluororibose sugar
      moiety
<220> FEATURE:
<221> NAME/KEY: misc_feature
<222> LOCATION: (17)..(17)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (18)..(18)
<223> OTHER INFORMATION: nucleoside contains a 2'-fluororibose sugar
      moiety
<220> FEATURE:
<221> NAME/KEY: misc_feature
<222> LOCATION: (19)..(21)
<223> OTHER INFORMATION: nucleoside contains a 2'-deoxy-2'-
      fluoroarabinose sugar moiety

<400> SEQUENCE: 13
aacucaccug uggccaaaac a                                              21

<210> SEQ ID NO 14
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-fluororibose sugar
      moiety
<220> FEATURE:
<221> NAME/KEY: misc_feature
<222> LOCATION: (1)..(1)
<223> OTHER INFORMATION: 5'-phosphate modification

<400> SEQUENCE: 14
uuuuggccac aggugaguuc c                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nucleoside contains a 2'-deoxy-2'-
      fluoroarabinose sugar moiety
<220> FEATURE:
<221> NAME/KEY: misc_feature
```

```
<222> LOCATION: (4)..(6)
<223> OTHER INFORMATION: nucleoside contains a 2'-fluororibose sugar
      moiety
<220> FEATURE:
<221> NAME/KEY: misc_feature
<222> LOCATION: (7)..(9)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (10)..(12)
<223> OTHER INFORMATION: nucleoside contains a 2'-fluororibose sugar
      moiety
<220> FEATURE:
<221> NAME/KEY: misc_feature
<222> LOCATION: (13)..(13)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (14)..(14)
<223> OTHER INFORMATION: nucleoside contains a 2'-fluororibose sugar
      moiety
<220> FEATURE:
<221> NAME/KEY: misc_feature
<222> LOCATION: (15)..(15)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (16)..(16)
<223> OTHER INFORMATION: nucleoside contains a 2'-fluororibose sugar
      moiety
<220> FEATURE:
<221> NAME/KEY: misc_feature
<222> LOCATION: (17)..(17)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (18)..(18)
<223> OTHER INFORMATION: nucleoside contains a 2'-fluororibose sugar
      moiety
<220> FEATURE:
<221> NAME/KEY: misc_feature
<222> LOCATION: (19)..(21)
<223> OTHER INFORMATION: nucleoside contains a 2'-deoxy-2'-
      fluoroarabinose sugar moiety

<400> SEQUENCE: 15
aacucacctg ugaccaaaac a                                              21

<210> SEQ ID NO 16
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-fluororibose sugar
      moiety
<220> FEATURE:
<221> NAME/KEY: misc_feature
<222> LOCATION: (1)..(1)
<223> OTHER INFORMATION: 5'-phosphate modification

<400> SEQUENCE: 16
uuuuggucac aggugaguuc c                                              21

<210> SEQ ID NO 17
<211> LENGTH: 21
<212> TYPE: DNA
<213> ORGANISM: Artificial Sequence
```

```
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (4)..(6)
<223> OTHER INFORMATION: nucleoside contains a 2'-fluororibose sugar
      moiety
<220> FEATURE:
<221> NAME/KEY: misc_feature
<222> LOCATION: (7)..(9)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (10)..(12)
<223> OTHER INFORMATION: nucleoside contains a 2'-fluororibose sugar
      moiety
<220> FEATURE:
<221> NAME/KEY: misc_feature
<222> LOCATION: (13)..(13)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (14)..(14)
<223> OTHER INFORMATION: nucleoside contains a 2'-fluororibose sugar
      moiety
<220> FEATURE:
<221> NAME/KEY: misc_feature
<222> LOCATION: (15)..(15)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (16)..(16)
<223> OTHER INFORMATION: nucleoside contains a 2'-fluororibose sugar
      moiety
<220> FEATURE:
<221> NAME/KEY: misc_feature
<222> LOCATION: (17)..(17)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (18)..(18)
<223> OTHER INFORMATION: nucleoside contains a 2'-fluororibose sugar
      moiety
<220> FEATURE:
<221> NAME/KEY: misc_feature
<222> LOCATION: (19)..(21)
<223> OTHER INFORMATION: nucleoside contains a 2'-deoxy-2'-
      fluoroarabinose sugar moiety

<400> SEQUENCE: 17
aagacuccaa agtagaagta a                                                  21

<210> SEQ ID NO 18
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-fluororibose sugar
      moiety
<220> FEATURE:
<221> NAME/KEY: misc_feature
<222> LOCATION: (1)..(1)
<223> OTHER INFORMATION: 5'-phosphate modification
```

```
<400> SEQUENCE: 18
acuucuacuu uggagucuuc a                                        21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 19
gcuugaaguc uuuaauuaat t                                        21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 20
uuaauuaaag acuucaagcg g                                        21

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 2'-deoxy-2'-fluoroarabinose sugar moiety
<220> FEATURE:
<221> NAME/KEY: misc_feature
<222> LOCATION: (2)..(4)
<223> OTHER INFORMATION: nucleoside contains a 2'-fluororibose sugar
      moiety
<220> FEATURE:
<221> NAME/KEY: misc_feature
<222> LOCATION: (5)..(8)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (9)..(13)
<223> OTHER INFORMATION: nucleoside contains a 2'-fluororibose sugar
      moiety
<220> FEATURE:
<221> NAME/KEY: misc_feature
<222> LOCATION: (14)..(15)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (16)..(17)
<223> OTHER INFORMATION: nucleoside contains a 2'-fluororibose sugar
```

```
            moiety
<220> FEATURE:
<221> NAME/KEY: misc_feature
<222> LOCATION: (18)..(21)
<223> OTHER INFORMATION: nucleoside contains a 2'-deoxy-2'-
      fluoroarabinose sugar moiety

<400> SEQUENCE: 21
gcttgaagtc tttaattaat t                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: nucleoside contains a 2'-fluororibose sugar
      moiety
<220> FEATURE:
<221> NAME/KEY: misc_feature
<222> LOCATION: (3)..(4)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (5)..(6)
<223> OTHER INFORMATION: nucleoside contains a 2'-fluororibose sugar
      moiety
<220> FEATURE:
<221> NAME/KEY: misc_feature
<222> LOCATION: (7)..(11)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (12)..(15)
<223> OTHER INFORMATION: nucleoside contains a 2'-fluororibose sugar
      moiety
<220> FEATURE:
<221> NAME/KEY: misc_feature
<222> LOCATION: (16)..(18)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (19)..(19)
<223> OTHER INFORMATION: nucleoside contains a 2'-fluororibose sugar
      moiety
<220> FEATURE:
<221> NAME/KEY: misc_feature
<222> LOCATION: (20)..(21)
<223> OTHER INFORMATION: nucleoside contains a 2'-deoxy-2'-
      fluoroarabinose sugar moiety

<400> SEQUENCE: 22
ttaattaaag acttcaagcg g                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (2)..(2)
<223> OTHER INFORMATION: nucleoside contains a 2'-fluororibose sugar
```

```
          moiety
<220> FEATURE:
<221> NAME/KEY: misc_feature
<222> LOCATION: (3)..(3)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (4)..(4)
<223> OTHER INFORMATION: nucleoside contains a 2'-fluororibose sugar
      moiety
<220> FEATURE:
<221> NAME/KEY: misc_feature
<222> LOCATION: (5)..(5)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (6)..(6)
<223> OTHER INFORMATION: nucleoside contains a 2'-fluororibose sugar
      moiety
<220> FEATURE:
<221> NAME/KEY: misc_feature
<222> LOCATION: (7)..(7)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (8)..(8)
<223> OTHER INFORMATION: nucleoside contains a 2'-fluororibose sugar
      moiety
<220> FEATURE:
<221> NAME/KEY: misc_feature
<222> LOCATION: (9)..(9)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (10)..(10)
<223> OTHER INFORMATION: nucleoside contains a 2'-fluororibose sugar
      moiety
<220> FEATURE:
<221> NAME/KEY: misc_feature
<222> LOCATION: (11)..(11)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (12)..(12)
<223> OTHER INFORMATION: nucleoside contains a 2'-fluororibose sugar
      moiety
<220> FEATURE:
<221> NAME/KEY: misc_feature
<222> LOCATION: (13)..(13)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (14)..(14)
<223> OTHER INFORMATION: nucleoside contains a 2'-fluororibose sugar
      moiety
<220> FEATURE:
<221> NAME/KEY: misc_feature
<222> LOCATION: (15)..(15)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (16)..(16)
<223> OTHER INFORMATION: nucleoside contains a 2'-fluororibose sugar
      moiety
<220> FEATURE:
<221> NAME/KEY: misc_feature
<222> LOCATION: (17)..(17)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (18)..(18)
```

<223> OTHER INFORMATION: nucleoside contains a 2'-fluororibose sugar
      moiety
<220> FEATURE:
<221> NAME/KEY: misc_feature
<222> LOCATION: (19)..(21)
<223> OTHER INFORMATION: nucleoside contains a 2'-deoxy-2'-
      fluoroarabinose sugar moiety

<400> SEQUENCE: 23
gcttgaagtc tttaattaat t                                           21

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: nucleoside contains a 2'-fluororibose sugar
      moiety
<220> FEATURE:
<221> NAME/KEY: misc_feature
<222> LOCATION: (2)..(2)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (3)..(3)
<223> OTHER INFORMATION: nucleoside contains a 2'-fluororibose sugar
      moiety
<220> FEATURE:
<221> NAME/KEY: misc_feature
<222> LOCATION: (4)..(4)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (5)..(5)
<223> OTHER INFORMATION: nucleoside contains a 2'-fluororibose sugar
      moiety
<220> FEATURE:
<221> NAME/KEY: misc_feature
<222> LOCATION: (6)..(6)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (7)..(7)
<223> OTHER INFORMATION: nucleoside contains a 2'-fluororibose sugar
      moiety
<220> FEATURE:
<221> NAME/KEY: misc_feature
<222> LOCATION: (8)..(8)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (9)..(9)
<223> OTHER INFORMATION: nucleoside contains a 2'-fluororibose sugar
      moiety
<220> FEATURE:
<221> NAME/KEY: misc_feature
<222> LOCATION: (10)..(10)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (11)..(11)
<223> OTHER INFORMATION: nucleoside contains a 2'-fluororibose sugar
      moiety
<220> FEATURE:
<221> NAME/KEY: misc_feature
<222> LOCATION: (12)..(12)
<223> OTHER INFORMATION: nucleoside contains a 2'-deoxy-2'-
      fluoroarabinose sugar moiety

```
<220> FEATURE:
<221> NAME/KEY: misc_feature
<222> LOCATION: (13)..(13)
<223> OTHER INFORMATION: nucleoside contains a 2'-fluororibose sugar
      moiety
<220> FEATURE:
<221> NAME/KEY: misc_feature
<222> LOCATION: (14)..(14)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (15)..(15)
<223> OTHER INFORMATION: nucleoside contains a 2'-fluororibose sugar
      moiety
<220> FEATURE:
<221> NAME/KEY: misc_feature
<222> LOCATION: (16)..(16)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (17)..(17)
<223> OTHER INFORMATION: nucleoside contains a 2'-fluororibose sugar
      moiety
<220> FEATURE:
<221> NAME/KEY: misc_feature
<222> LOCATION: (18)..(18)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (19)..(19)
<223> OTHER INFORMATION: nucleoside contains a 2'-fluororibose sugar
      moiety
<220> FEATURE:
<221> NAME/KEY: misc_feature
<222> LOCATION: (20)..(21)
<223> OTHER INFORMATION: nucleoside contains a 2'-deoxy-2'-
      fluoroarabinose sugar moiety

<400> SEQUENCE: 24
ttaattaaag acttcaagcg g                                            21

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-fluororibose sugar
      moiety

<400> SEQUENCE: 25
gcttgaagtc tttaattaat t                                            21

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-fluororibose sugar
      moiety
<220> FEATURE:
<221> NAME/KEY: misc_feature
<222> LOCATION: (1)..(1)
<223> OTHER INFORMATION: 5'-phosphate modification
```

```
<400> SEQUENCE: 26
ttaattaaag acttcaagcg g                                              21

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-deoxy-2'-
      fluoroarabinose sugar moiety

<400> SEQUENCE: 27
gcttgaagtc tttaattaat t                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (1)..(1)
<223> OTHER INFORMATION: 5'-phosphate modification

<400> SEQUENCE: 28
ttaattaaag acttcaagcg g                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 29
cguacgcgga auacuucgat t                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 30
```
ucgaaguauu ccgcguacgt t                                              21

<210> SEQ ID NO 31
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-fluororibose sugar
      moiety

<400> SEQUENCE: 31
cguacgcgga auacuucgau u                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-deoxy-2'-
      fluoroarabinose sugar moiety

<400> SEQUENCE: 32
cgtacgcgga atacttcgat t                                              21

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (15)..(19)
<223> OTHER INFORMATION: RNA
<220> FEATURE:
<221> NAME/KEY: misc_feature
<222> LOCATION: (20)..(21)
<223> OTHER INFORMATION: nucleoside contains a 2'-deoxy-2'-
      fluoroarabinose sugar moiety

<400> SEQUENCE: 33
cgtacgcgga atacuucgat t                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (4)..(6)
<223> OTHER INFORMATION: nucleoside contains a 2'-fluororibose sugar -continued

```
     moiety
<220> FEATURE:
<221> NAME/KEY: misc_feature
<222> LOCATION: (7)..(9)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (10)..(12)
<223> OTHER INFORMATION: nucleoside contains a 2'-fluororibose sugar
      moiety
<220> FEATURE:
<221> NAME/KEY: misc_feature
<222> LOCATION: (13)..(15)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (16)..(18)
<223> OTHER INFORMATION: nucleoside contains a 2'-fluororibose sugar
      moiety
<220> FEATURE:
<221> NAME/KEY: misc_feature
<222> LOCATION: (19)..(21)
<223> OTHER INFORMATION: nucleoside contains a 2'-deoxy-2'-
      fluoroarabinose sugar moiety

<400> SEQUENCE: 34
cgtacgcgga auacucgat t                                                  21

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (4)..(6)
<223> OTHER INFORMATION: nucleoside contains a 2'-fluororibose sugar
      moiety
<220> FEATURE:
<221> NAME/KEY: misc_feature
<222> LOCATION: (7)..(9)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (10)..(12)
<223> OTHER INFORMATION: nucleoside contains a 2'-fluororibose sugar
      moiety
<220> FEATURE:
<221> NAME/KEY: misc_feature
<222> LOCATION: (13)..(13)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (14)..(14)
<223> OTHER INFORMATION: nucleoside contains a 2'-fluororibose sugar
      moiety
<220> FEATURE:
<221> NAME/KEY: misc_feature
<222> LOCATION: (15)..(15)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (16)..(16)
<223> OTHER INFORMATION: nucleoside contains a 2'-fluororibose sugar
      moiety
<220> FEATURE:
```

```
<221> NAME/KEY: misc_feature
<222> LOCATION: (17)..(17)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (18)..(18)
<223> OTHER INFORMATION: nucleoside contains a 2'-fluororibose sugar
      moiety
<220> FEATURE:
<221> NAME/KEY: misc_feature
<222> LOCATION: (19)..(21)
<223> OTHER INFORMATION: nucleoside contains a 2'-deoxy-2'-
      fluoroarabinose sugar moiety

<400> SEQUENCE: 35
cgtacgcgga auacucgat t                                                  21

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (2)..(2)
<223> OTHER INFORMATION: nucleoside contains a 2'-fluororibose sugar
      moiety
<220> FEATURE:
<221> NAME/KEY: misc_feature
<222> LOCATION: (3)..(3)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (4)..(4)
<223> OTHER INFORMATION: nucleoside contains a 2'-fluororibose sugar
      moiety
<220> FEATURE:
<221> NAME/KEY: misc_feature
<222> LOCATION: (5)..(5)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (6)..(6)
<223> OTHER INFORMATION: nucleoside contains a 2'-fluororibose sugar
      moiety
<220> FEATURE:
<221> NAME/KEY: misc_feature
<222> LOCATION: (7)..(7)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (8)..(8)
<223> OTHER INFORMATION: nucleoside contains a 2'-fluororibose sugar
      moiety
<220> FEATURE:
<221> NAME/KEY: misc_feature
<222> LOCATION: (9)..(9)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (10)..(10)
<223> OTHER INFORMATION: nucleoside contains a 2'-fluororibose sugar
      moiety
<220> FEATURE:
<221> NAME/KEY: misc_feature
<222> LOCATION: (11)..(11)
```

<223> OTHER INFORMATION: nucleoside contains a 2'-deoxy-2'-
      fluoroarabinose sugar moiety
<220> FEATURE:
<221> NAME/KEY: misc_feature
<222> LOCATION: (12)..(12)
<223> OTHER INFORMATION: nucleoside contains a 2'-fluororibose sugar
      moiety
<220> FEATURE:
<221> NAME/KEY: misc_feature
<222> LOCATION: (13)..(13)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (14)..(14)
<223> OTHER INFORMATION: nucleoside contains a 2'-fluororibose sugar
      moiety
<220> FEATURE:
<221> NAME/KEY: misc_feature
<222> LOCATION: (15)..(15)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (16)..(16)
<223> OTHER INFORMATION: nucleoside contains a 2'-fluororibose sugar
      moiety
<220> FEATURE:
<221> NAME/KEY: misc_feature
<222> LOCATION: (17)..(17)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (18)..(18)
<223> OTHER INFORMATION: nucleoside contains a 2'-fluororibose sugar
      moiety
<220> FEATURE:
<221> NAME/KEY: misc_feature
<222> LOCATION: (19)..(21)
<223> OTHER INFORMATION: nucleoside contains a 2'-deoxy-2'-
      fluoroarabinose sugar moiety

<400> SEQUENCE: 36
cgtacgcgga auacuucgat t                                              21

<210> SEQ ID NO 37
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-fluororibose sugar
      moiety
<220> FEATURE:
<221> NAME/KEY: misc_feature
<222> LOCATION: (1)..(1)
<223> OTHER INFORMATION: 5'-phosphate modification

<400> SEQUENCE: 37
ucgaaguauu ccgcguacgu u                                              21

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: RNA

```
<220> FEATURE:
<221> NAME/KEY: misc_feature
<222> LOCATION: (1)..(1)
<223> OTHER INFORMATION: 5'-phosphate modification
<220> FEATURE:
<221> NAME/KEY: misc_feature
<222> LOCATION: (19)..(19)
<223> OTHER INFORMATION: nucleoside contains a LNA-type sugar moiety
      comprising a 2' to 4' bridge
<220> FEATURE:
<221> NAME/KEY: misc_feature
<222> LOCATION: (20)..(21)
<223> OTHER INFORMATION: nucleoside contains a 2'-deoxy-2'-
      fluoroarabinose sugar moiety

<400> SEQUENCE: 38
uuaauuaaag acuucaagcg g                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: RNA
<220> FEATURE:
<221> NAME/KEY: misc_feature
<222> LOCATION: (1)..(1)
<223> OTHER INFORMATION: 5'-phosphate modification
<220> FEATURE:
<221> NAME/KEY: misc_feature
<222> LOCATION: (17)..(17)
<223> OTHER INFORMATION: nucleoside contains a LNA-type sugar moiety
      comprising a 2' to 4' bridge
<220> FEATURE:
<221> NAME/KEY: misc_feature
<222> LOCATION: (18)..(18)
<223> OTHER INFORMATION: RNA
<220> FEATURE:
<221> NAME/KEY: misc_feature
<222> LOCATION: (19)..(19)
<223> OTHER INFORMATION: nucleoside contains a LNA-type sugar moiety
      comprising a 2' to 4' bridge
<220> FEATURE:
<221> NAME/KEY: misc_feature
<222> LOCATION: (20)..(21)
<223> OTHER INFORMATION: nucleoside contains a 2'-deoxy-2'-
      fluoroarabinose sugar moiety

<400> SEQUENCE: 39
uuaauuaaag acuucaagcg g                                              21

<210> SEQ ID NO 40
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(6)
<223> OTHER INFORMATION: RNA
<220> FEATURE:
<221> NAME/KEY: misc_feature
<222> LOCATION: (7)..(8)
<223> OTHER INFORMATION: nucleoside contains a LNA-type sugar moiety
      comprising a 2' to 4' bridge
<220> FEATURE:
<221> NAME/KEY: misc_feature
<222> LOCATION: (9)..(18)
<223> OTHER INFORMATION: RNA
<220> FEATURE:
```

```
<221> NAME/KEY: misc_feature
<222> LOCATION: (19)..(19)
<223> OTHER INFORMATION: nucleoside contains a LNA-type sugar moiety
      comprising a 2' to 4' bridge
<220> FEATURE:
<221> NAME/KEY: misc_feature
<222> LOCATION: (20)..(21)
<223> OTHER INFORMATION: nucleoside contains a 2'-deoxy-2'-
      fluoroarabinose sugar moiety

<400> SEQUENCE: 40
uuaauuaaaa gacuucaagc gg                                                  22

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (15)..(19)
<223> OTHER INFORMATION: RNA
<220> FEATURE:
<221> NAME/KEY: misc_feature
<222> LOCATION: (20)..(21)
<223> OTHER INFORMATION: nucleoside contains a 2'-deoxy-2'-
      fluoroarabinose sugar moiety

<400> SEQUENCE: 41
gcttgaagtc tttaauuaat t                                                   21

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (1)..(1)
<223> OTHER INFORMATION: 5'-phosphate modification
<220> FEATURE:
<221> NAME/KEY: misc_feature
<222> LOCATION: (20)..(21)
<223> OTHER INFORMATION: nucleoside contains a 2'-deoxy-2'-
      fluoroarabinose sugar moiety

<400> SEQUENCE: 42
uuaauuaaag acuucaagcg g                                                   21

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: nucleoside contains a 2'-deoxy-2'-
      fluoroarabinose sugar moiety
<220> FEATURE:
<221> NAME/KEY: misc_feature
```

```
<222> LOCATION: (2)..(2)
<223> OTHER INFORMATION: RNA
<220> FEATURE:
<221> NAME/KEY: misc_feature
<222> LOCATION: (3)..(3)
<223> OTHER INFORMATION: nucleoside contains a LNA-type sugar moiety
      comprising a 2' to 4' bridge
<220> FEATURE:
<221> NAME/KEY: misc_feature
<222> LOCATION: (4)..(4)
<223> OTHER INFORMATION: RNA
<220> FEATURE:
<221> NAME/KEY: misc_feature
<222> LOCATION: (5)..(8)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (9)..(10)
<223> OTHER INFORMATION: RNA
<220> FEATURE:
<221> NAME/KEY: misc_feature
<222> LOCATION: (11)..(11)
<223> OTHER INFORMATION: nucleoside contains a LNA-type sugar moiety
      comprising a 2' to 4' bridge
<220> FEATURE:
<221> NAME/KEY: misc_feature
<222> LOCATION: (12)..(13)
<223> OTHER INFORMATION: RNA
<220> FEATURE:
<221> NAME/KEY: misc_feature
<222> LOCATION: (14)..(15)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (16)..(16)
<223> OTHER INFORMATION: nucleoside contains a LNA-type sugar moiety
      comprising a 2' to 4' bridge
<220> FEATURE:
<221> NAME/KEY: misc_feature
<222> LOCATION: (17)..(17)
<223> OTHER INFORMATION: RNA
<220> FEATURE:
<221> NAME/KEY: misc_feature
<222> LOCATION: (18)..(21)
<223> OTHER INFORMATION: nucleoside contains a 2'-deoxy-2'-
      fluoroarabinose sugar moiety

<400> SEQUENCE: 43
gcuugaaguc uuuaauuaat t                                              21

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (2)..(2)
<223> OTHER INFORMATION: RNA
<220> FEATURE:
<221> NAME/KEY: misc_feature
<222> LOCATION: (3)..(3)
<223> OTHER INFORMATION: nucleoside contains a LNA-type sugar moiety
      comprising a 2' to 4' bridge
<220> FEATURE:
<221> NAME/KEY: misc_feature
<222> LOCATION: (4)..(4)
<223> OTHER INFORMATION: RNA
<220> FEATURE:
```

```
<221> NAME/KEY: misc_feature
<222> LOCATION: (5)..(8)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (9)..(10)
<223> OTHER INFORMATION: RNA
<220> FEATURE:
<221> NAME/KEY: misc_feature
<222> LOCATION: (11)..(11)
<223> OTHER INFORMATION: nucleoside contains a LNA-type sugar moiety
      comprising a 2' to 4' bridge
<220> FEATURE:
<221> NAME/KEY: misc_feature
<222> LOCATION: (12)..(13)
<223> OTHER INFORMATION: RNA
<220> FEATURE:
<221> NAME/KEY: misc_feature
<222> LOCATION: (14)..(14)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (15)..(15)
<223> OTHER INFORMATION: RNA
<220> FEATURE:
<221> NAME/KEY: misc_feature
<222> LOCATION: (16)..(16)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (17)..(17)
<223> OTHER INFORMATION: nucleoside contains a LNA-type sugar moiety
      comprising a 2' to 4' bridge
<220> FEATURE:
<221> NAME/KEY: misc_feature
<222> LOCATION: (18)..(18)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (19)..(19)
<223> OTHER INFORMATION: RNA
<220> FEATURE:
<221> NAME/KEY: misc_feature
<222> LOCATION: (20)..(21)
<223> OTHER INFORMATION: nucleoside contains a 2'-deoxy-2'-
      fluoroarabinose sugar moiety

<400> SEQUENCE: 44
gcuugaaguc uuuaatuaat t                                            21

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (2)..(2)
<223> OTHER INFORMATION: RNA
<220> FEATURE:
<221> NAME/KEY: misc_feature
<222> LOCATION: (3)..(3)
<223> OTHER INFORMATION: nucleoside contains a LNA-type sugar moiety
      comprising a 2' to 4' bridge
<220> FEATURE:
<221> NAME/KEY: misc_feature
<222> LOCATION: (4)..(4)
```

```
<223> OTHER INFORMATION: RNA
<220> FEATURE:
<221> NAME/KEY: misc_feature
<222> LOCATION: (5)..(8)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (9)..(10)
<223> OTHER INFORMATION: RNA
<220> FEATURE:
<221> NAME/KEY: misc_feature
<222> LOCATION: (11)..(11)
<223> OTHER INFORMATION: nucleoside contains a LNA-type sugar moiety
      comprising a 2' to 4' bridge
<220> FEATURE:
<221> NAME/KEY: misc_feature
<222> LOCATION: (12)..(13)
<223> OTHER INFORMATION: RNA
<220> FEATURE:
<221> NAME/KEY: misc_feature
<222> LOCATION: (14)..(15)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (16)..(17)
<223> OTHER INFORMATION: RNA
<220> FEATURE:
<221> NAME/KEY: misc_feature
<222> LOCATION: (18)..(21)
<223> OTHER INFORMATION: nucleoside contains a 2'-deoxy-2'-
      fluoroarabinose sugar moiety

<400> SEQUENCE: 45
gcuugaaguc uuuaauuaat t                                                 21

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (2)..(2)
<223> OTHER INFORMATION: RNA
<220> FEATURE:
<221> NAME/KEY: misc_feature
<222> LOCATION: (4)..(4)
<223> OTHER INFORMATION: RNA
<220> FEATURE:
<221> NAME/KEY: misc_feature
<222> LOCATION: (5)..(8)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (9)..(10)
<223> OTHER INFORMATION: RNA
<220> FEATURE:
<221> NAME/KEY: misc_feature
<222> LOCATION: (11)..(11)
<223> OTHER INFORMATION: nucleoside contains a LNA-type sugar moiety
      comprising a 2' to 4' bridge
<220> FEATURE:
<221> NAME/KEY: misc_feature
<222> LOCATION: (12)..(13)
<223> OTHER INFORMATION: RNA
<220> FEATURE:
<221> NAME/KEY: misc_feature
<222> LOCATION: (14)..(14)
```

```
<223> OTHER INFORMATION: nucleoside contains a 2'-deoxy-2'-
      fluoroarabinose sugar moiety
<220> FEATURE:
<221> NAME/KEY: misc_feature
<222> LOCATION: (15)..(15)
<223> OTHER INFORMATION: RNA
<220> FEATURE:
<221> NAME/KEY: misc_feature
<222> LOCATION: (16)..(16)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (17)..(17)
<223> OTHER INFORMATION: RNA
<220> FEATURE:
<221> NAME/KEY: misc_feature
<222> LOCATION: (18)..(18)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (20)..(21)
<223> OTHER INFORMATION: nucleoside contains a 2'-deoxy-2'-
      fluoroarabinose sugar moiety

<400> SEQUENCE: 46
gcuugaaguc uuuaatuaat t                                                   21

<210> SEQ ID NO 47
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (2)..(2)
<223> OTHER INFORMATION: RNA
<220> FEATURE:
<221> NAME/KEY: misc_feature
<222> LOCATION: (3)..(3)
<223> OTHER INFORMATION: nucleoside contains a LNA-type sugar moiety
      comprising a 2' to 4' bridge
<220> FEATURE:
<221> NAME/KEY: misc_feature
<222> LOCATION: (4)..(4)
<223> OTHER INFORMATION: RNA
<220> FEATURE:
<221> NAME/KEY: misc_feature
<222> LOCATION: (5)..(8)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (9)..(10)
<223> OTHER INFORMATION: RNA
<220> FEATURE:
<221> NAME/KEY: misc_feature
<222> LOCATION: (11)..(11)
<223> OTHER INFORMATION: nucleoside contains a LNA-type sugar moiety
      comprising a 2' to 4' bridge
<220> FEATURE:
<221> NAME/KEY: misc_feature
<222> LOCATION: (12)..(13)
<223> OTHER INFORMATION: RNA
<220> FEATURE:
<221> NAME/KEY: misc_feature
<222> LOCATION: (14)..(14)
<223> OTHER INFORMATION: nucleoside contains a 2'-deoxy-2'-
      fluoroarabinose sugar moiety
<220> FEATURE:
```

```
<221> NAME/KEY: misc_feature
<222> LOCATION: (15)..(19)
<223> OTHER INFORMATION: RNA
<220> FEATURE:
<221> NAME/KEY: misc_feature
<222> LOCATION: (20)..(21)
<223> OTHER INFORMATION: nucleoside contains a 2'-deoxy-2'-
      fluoroarabinose sugar moiety

<400> SEQUENCE: 47
gcuugaaguc uuuaauuaat t                                              21

<210> SEQ ID NO 48
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 48
uguuauugcc aagcacuuaa a                                              21

<210> SEQ ID NO 49
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 49
uaagugcuug gcaauaacag a                                              21

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (4)..(6)
<223> OTHER INFORMATION: nucleoside contains a 2'-fluororibose sugar
      moiety
<220> FEATURE:
<221> NAME/KEY: misc_feature
<222> LOCATION: (7)..(9)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (10)..(12)
<223> OTHER INFORMATION: nucleoside contains a 2'-fluororibose sugar
      moiety
<220> FEATURE:
<221> NAME/KEY: misc_feature
<222> LOCATION: (13)..(13)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (14)..(14)
<223> OTHER INFORMATION: nucleoside contains a 2'-fluororibose sugar
      moiety
<220> FEATURE:
<221> NAME/KEY: misc_feature
<222> LOCATION: (15)..(15)
<223> OTHER INFORMATION: nucleoside contains a 2'-deoxy-2'-
      fluoroarabinose sugar moiety
```

```
<220> FEATURE:
<221> NAME/KEY: misc_feature
<222> LOCATION: (16)..(16)
<223> OTHER INFORMATION: nucleoside contains a 2'-fluororibose sugar
      moiety
<220> FEATURE:
<221> NAME/KEY: misc_feature
<222> LOCATION: (17)..(17)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (18)..(18)
<223> OTHER INFORMATION: nucleoside contains a 2'-fluororibose sugar
      moiety
<220> FEATURE:
<221> NAME/KEY: misc_feature
<222> LOCATION: (19)..(21)
<223> OTHER INFORMATION: nucleoside contains a 2'-deoxy-2'-
      fluoroarabinose sugar moiety

<400> SEQUENCE: 50
tgtuautgcc aagcactuaa a                                              21

<210> SEQ ID NO 51
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-fluororibose sugar
      moiety
<220> FEATURE:
<221> NAME/KEY: misc_feature
<222> LOCATION: (1)..(1)
<223> OTHER INFORMATION: 5'-phosphate modification

<400> SEQUENCE: 51
uaagugcuug gcaauaacag a                                              21

<210> SEQ ID NO 52
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (2)..(2)
<223> OTHER INFORMATION: RNA
<220> FEATURE:
<221> NAME/KEY: misc_feature
<222> LOCATION: (3)..(3)
<223> OTHER INFORMATION: nucleoside contains a LNA-type sugar moiety
      comprising a 2' to 4' bridge
<220> FEATURE:
<221> NAME/KEY: misc_feature
<222> LOCATION: (4)..(4)
<223> OTHER INFORMATION: RNA
<220> FEATURE:
<221> NAME/KEY: misc_feature
<222> LOCATION: (5)..(8)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (9)..(10)
```

```
<223> OTHER INFORMATION: RNA
<220> FEATURE:
<221> NAME/KEY: misc_feature
<222> LOCATION: (11)..(11)
<223> OTHER INFORMATION: nucleoside contains a LNA-type sugar moiety
      comprising a 2' to 4' bridge
<220> FEATURE:
<221> NAME/KEY: misc_feature
<222> LOCATION: (12)..(13)
<223> OTHER INFORMATION: RNA
<220> FEATURE:
<221> NAME/KEY: misc_feature
<222> LOCATION: (14)..(15)
<223> OTHER INFORMATION: nucleoside contains a 2'-deoxy-2'-
      fluoroarabinose sugar moiety
<220> FEATURE:
<221> NAME/KEY: misc_feature
<222> LOCATION: (16)..(16)
<223> OTHER INFORMATION: nucleoside contains a LNA-type sugar moiety
      comprising a 2' to 4' bridge
<220> FEATURE:
<221> NAME/KEY: misc_feature
<222> LOCATION: (17)..(17)
<223> OTHER INFORMATION: RNA
<220> FEATURE:
<221> NAME/KEY: misc_feature
<222> LOCATION: (18)..(21)
<223> OTHER INFORMATION: nucleoside contains a 2'-deoxy-2'-
      fluoroarabinose sugar moiety

<400> SEQUENCE: 52
tguuattgcc aagcacutaa a                                            21

<210> SEQ ID NO 53
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: nucleoside contains a 2'-fluororibose sugar
      moiety

<400> SEQUENCE: 53
uuaauuaaag acuucaagcg g                                            21

<210> SEQ ID NO 54
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 54
gcuugauuuc ugaaauuaat t                                            21

<210> SEQ ID NO 55
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 55
uuaauuucag aaaucaagcg g                                              21

<210> SEQ ID NO 56
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (1)..(1)
<223> OTHER INFORMATION: 5'-phosphate modification
<220> FEATURE:
<221> NAME/KEY: misc_feature
<222> LOCATION: (20)..(21)
<223> OTHER INFORMATION: DNA

<400> SEQUENCE: 56
uuaauuaaag acuucaagcg g                                              21
```